United States Patent [19]

Ong et al.

[11] Patent Number: 4,672,138
[45] Date of Patent: Jun. 9, 1987

[54] PHENYL SUBSTITUTED CARBAMOTHIOIC ACID ESTERS

[75] Inventors: Helen H. Ong, Whippany, N.J.; James A. Profitt, Goshen, Ind.

[73] Assignee: Hoechst Roussel Pharmaceuticals Inc., Somerville, N.J.

[21] Appl. No.: 825,725

[22] Filed: Feb. 3, 1986

Related U.S. Application Data

[60] Continuation of Ser. No. 558,079, Dec. 5, 1983, which is a division of Ser. No. 256,470, Apr. 4, 1981, which is a continuation-in-part of Ser. No. 198,736, Oct. 20, 1980.

[51] Int. Cl.$^4$ ............................................. C07C 155/02
[52] U.S. Cl. ..................................... 558/234; 558/241
[58] Field of Search ................................ 558/234, 241

[56] References Cited

U.S. PATENT DOCUMENTS

| | | | |
|---|---|---|---|
| 3,352,815 | 11/1967 | Bencze | 558/241 |
| 3,952,013 | 4/1976 | Hazard et al. | 558/241 |
| 3,952,064 | 4/1976 | Whalley | 558/241 |
| 4,024,272 | 5/1977 | Rogalski et al. | 558/241 |

FOREIGN PATENT DOCUMENTS 2411826  3/1974  Fed. Rep. of Germany ...... 558/241

Primary Examiner—Alan L. Rotman
Assistant Examiner—Robert C. Whittenbaugh
Attorney, Agent, or Firm—Raymond R. Wittekind

[57] ABSTRACT

Novel benzo[b]thiophenes, compositions containing same, process for the preparation thereof and methods of reducing blood pressure and producing diuresis by administration of the compounds and compositions are disclosed.

4 Claims, No Drawings

PHENYL SUBSTITUTED CARBAMOTHIOIC ACID ESTERS

This is a continuation of application Ser. No. 558,079 filed Dec. 5, 1983, which is a divisional application of U.S. patent application Ser. No. **256,470, filed Apr. 4, 1981, which is a continuation-in-part of U.S. patent application Ser. No. 198,736, filed Oct. 20, 1980.

DESCRIPTION OF THE INVENTION

The present invention relates to novel benzo[b]thiophenes.

More particularly, the present invention relates to benzo[b]thiophenes of the formula

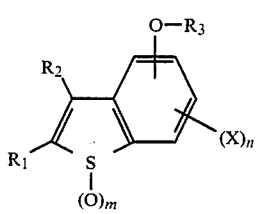

wherein $R_1$ is lower alkanoyl, formyl, hydroxymethyl or a group of the formula

wherein $R_{19}$ and $R_{20}$ are each independently hydrogen or lower alkyl; $R_1$ and $R_2$ each independently are hydrogen, lower alkyl, lower cycloalkyl, or a group of the formula

wherein Y is hydrogen, halogen, lower alkyl, lower alkoxy or hydroxy and p is 1 or 2; $R_1$ and $R_2$ taken together form a group of the formula $$-(CH_2)_q-$$

wherein q is 3, 4, or 5; $R_3$ is hydrogen or Z wherein Z is lower alkyl or a group of the formula

wherein $R_4$ and $R_5$ are hydrogen or lower alkyl; $R_6$ is carboxy, hydroxymethyl, lower alkoxycarbonyl, or hydroxyaminocarbonyl; X is hydrogen, halogen or lower alkyl; n is 1 or 2 and m is 0, 1 or 2 or a pharmaceutically acceptable basic addition salt thereof when $R_6$ is carboxy, which are useful as blood pressure reducing or diuresis producing agents alone or in combination with inert blood pressure reducing or diuresis producing adjuvants.

Preferred anti-hypertensive and diuretic benzo[b]thiophenes of the present invention are those where Z is a group of the formula

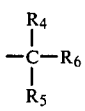

wherein $R_4$ and $R_5$ are hydrogen; $R_6$ is carboxy or lower alkoxycarbonyl; X is halogen; m is 0 or 2; n is 2 and the O-$R_3$ substituent is attached to the 5-position of the benzo[b]thiophene nucleus.

The present invention also relates, more particularly, to 2,3-dihydrobenzo[b]thiophenes of the formula

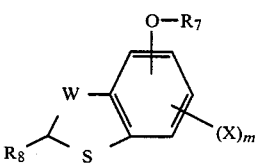

wherein $R_7$ is lower alkyl; $R_8$ is hydrogen, lower alkyl, lower cycloalkyl or a group of the formula

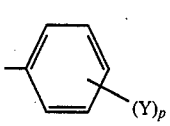

wherein Y is hydrogen, halogen, lower alkyl, lower alkoxy or hydroxy and p is 1 or 2; W is carbonyl or a group of the formula

wherein $R_9$ is hydrogen, lower alkyl, lower cycloalkyl or a group of the formula

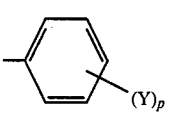

wherein Y and p are as above; X is hydrogen, halogen or lower alkyl; and n is 1 or 2, and to sulfides of the formula

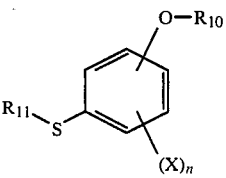

wherein $R_{10}$ is lower alkyl; $R_{11}$ is hydrogen or a group of the formula

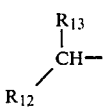

wherein $R_{12}$ is hydrogen, lower alkyl, lower cycloalkyl or a group of the formula

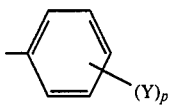

wherein Y is hydrogen, halogen, lower alkyl, lower alkoxy or hydroxy and p is 1 or 2; $R_{13}$ is carboxy, lower alkoxycarbonyl or a group of the formula

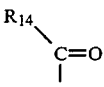

wherein $R_{14}$ is hydrogen, lower alkyl, lower cycloalkyl or a group of the formula

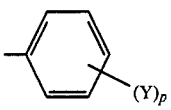

wherein Y and p are as above; $R_{12}$ and $R_{14}$ taken together form a group of the formula

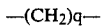

wherein q is 3, 4, or 5; X is hydrogen, halogen or lower alkyl; and n is 1 or 2, which are useful as intermediates for the synthesis of the herein aforementioned benzo[b]-thiophenes.

As used throughout the specification and appended claims, the term "alkyl" refers to a straight or branched chain hydrocarbon radical containing no unsaturation and having 1 to 10 carbon atoms such as methyl, ethyl, n-propyl, i-propyl, tert-butyl, hexyl, octyl, decyl and the like; the term "cycloalkyl" refers to a saturated hydrocarbon group possessing at least one carbocyclic ring, the ring containing from 3 to 10 carbon atoms such as cyclopropyl, cyclobutyl, cyclopentyl, cyclohexyl, cyclooctyl, 1-adamantyl and the like, the term "alkoxy" refers to a monovalent substituent which consists of an alkyl group linked through an ether oxygen and having its free valence bond from the ether oxygen such as methoxy, ethoxy, isopropoxy, tert-butoxy, hexoxy, octoxy, decoxy and the like; the term "alkanol" refers to a compound found by combination of an alkyl group and hydroxy radical. Examples of alkanols are methanol, ethanol, n- and 2-propanol, 2,2-dimethylethanol, hexanol, octanol, decanol and the like. The term "alkanoic acid" refers to a compound formed by combination of a carboxyl group with a hydrogen atom or alkyl group. Examples of alkanoic acids are formic acid, acetic acid, propanoic acid, 2,2-dimethylacetic acid, hexanoic acid, octanoic acid, decanoic acid and the like; the term "alkanoyl" refers to a radical form by removal of the hydroxyl group of an alkanoic acid. Examples of alkanoyl radicals are acetyl, propionyl, 2,2-dimethylacetyl, hexanoyl, octanoyl, decanoyl and the like; the terms "alkanoyloxy" refers to a radical formed by removal of hydrogen atom of the hydroxyl group of an alkanoic acid. Examples of alkanoyloxy radicals are acetoxy, propionyloxy, 2,2-dimethylacetoxy, hexanoyloxy, octanoyloxy, deconoyloxy and the like; the term "halogen" refers to a member of the family fluorine, chlorine, bromine or iodine. The term "lower" as applied to any of the aforementioned groups refers to a group having a carbon skeleton containing up to and including 6 carbon atoms.

In the formulas presented herein to depict the structures of the 2,3-dihydrobenzo[b]thiophenes, substituents attached to the heterocyclic ring system may be situated in either the geometrical cis- or trans-configurations, i.e., the substiuents may be situated on the same side or on opposite sides of the average plane of the ring system, respectively. For example, the substituent designated $R_8$ may be in either the cis- or trans-configuration with respect to the spatial configuration of the substituent designated $R_9$ or the hydroxy group.

The compounds of the present invention which lack an element of symmetry exist as optical antipodes and as the racemic forms thereof. The optical antipode may be prepared from the corresponding racemic forms by standard optical resolution techniques, involving, for example, the separation of disastereameric salts of those instant compounds characterized by the presence of a carboxy group and an optically active base, or by the synthesis from optically active precursors.

The present invention comprehends all geometric isomers, optical isomers and racemic forms thereof of the compounds disclosed and claimed herein and the formulas of the compounds shown herein are intended to encompass all possible geometric and optical isomers of the compounds so depicted.

The novel compounds of the present invention may be prepared from readily available anisoles of formula 1 by the sequence of reactions illustrated in Reaction Schemes I and II.

In the initial steps, the anisole 1 is converted to the benzenesulfonyl halide 2 which is reduced to the thiophenol 3. The halosulfonation is conveniently performed using excess fluoro- or chlorosulfonic acid, preferably chlorosulfonic acid, either neat or in the presence of a halocarbon solvent such as, for example, methylene chloride, chloroform or carbon tetrachloride. Various reducing systems may be employed to convert 2 to 3. Among those, there may be mentioned metals such as, for example, zinc or tin, mineral acids such as, for example, sulfuric acid or hydrochloric acid, alkali metal aluminum hydrides such as, for example, lithium aluminum hydride and sodium aluminum hydride and phosphorus, potassium iodide-phosphoric acid reagent. Zinc and sulfuric acid is the preferred reducing system.

The thiophenol 3 may also be prepared by an alternative process involving conversion of phenol 1 to thiocarbonate 2A, the thermal rearrangement of 2A to carbamate 2B and the hydrolysis of 2B to 3. The formation of thiocarbamate 2A is performed by generating the phenoxide of 1 with a strong base such as, for example, sodium or potassium hydride, in an appropriate ethereal solvent such as diethylether, dimethoxyethane, dimethoxyethoxyethane, tetrahydrofuran or dioxane and treating the anion so formed with a diloweralkylthiocarbamoyl halide of the formula

wherein R is lower alkyl and X' is chloro or bromo. Sodium hydride and dimethoxyethoxyethane is the preferred anion generating system and dimethylthiocarbamyl chloride is the preferred carbomoyl halide.

The rearrangement of 2A or 2B is conveniently carried out in the molten state by heating thiocarbamate 2A is a temperature within the range of about 225° C. to about 275° C., a temperature of about 250° C. being preferred. To prevent undesirable side reactions, the thermolysis is preferably performed under an inert atmosphere of, for example, nitrogen, helium or argon.

The hydrolysis of carbamate 2B to thiophenol 3 is performed under basic conditions employing an alkali metal hydroxide such as lithium, sodium or potassium hydroxide in an alcoholic solvent such as methanol, ethanol, i-propanol and the like, or a glycol such as ethylene glycol, propylene glycol and the like. Sodium or potassium hydroxide in ethylene glycol is the preferred hydrolysis medium. The hydrolysis is preferably performed at the reflux temperature of the solvent, at which it proceeds at a reasonable rate.

In the intermediate steps of the process for the preparation of the compounds of the present invention, the thiophenol 3 is converted to the benzo[b]thiophene 9 via the oxothioether 5 or through the intermediacy of the carboxy- or alkoxycarbonylthioethers 6 and dihydrobenzo[b]thiophenes 7 and 8. The synthesis of 5 is effected by treating the thiophenol 3 with an alkylating agent of the formula

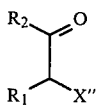

wherein $R_1$ and $R_2$ are as hereinbefore described and X" is a chloro, bromo or iodo in the presence of an alkali metal hydride and a polar aprotic solvent. Suitable alkali metal hydrides include sodium hydride, potassium hydride and the like, sodium hydride being preferred. Suitable polar aprotic solvent include dimethylsulfoxide, dimethylacetamide, dimethylformamide, hexamethylphosphoramide and the like, dimethylformamide being preferred.

In an alternative process for the preparation of oxothioether 5 wherein $R_1$ is a group of the formula

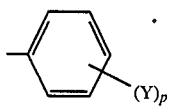

wherein Y is hydrogen, halogen, lower alkyl or alkoxy and p is 1 or 2, thiophenol 3 is alkylated to thioether 4 which is acylated to 5. The alkylation is accomplished by treating 3 with a compound of the formula

wherein $R_1$ is a group of the formula

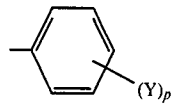

and X", Y and p are as defined above under those conditions employed for the transformation of 3 to 5. The acylation is carried out by first treating 4 with a strong base such as, for example, methyl- or n-butyllithium in an ethereal solvent such as, for example, diethylether, dimethoxyethane, dioxane or tetrahydrofuran, to form the carbanion thereof and then contacting the carbanion with a compound of the formula

wherein $R_2$ is as defined hereinbefore and $R_{16}$ is lower alkyl to introduce the acyl function. n-Butyllithium and tetrahydrofuran are, respectively, the preferred strong base and etheral solvent. While the reaction temperature is not narrowly critical, it is preferred to perform the acylation at a reduced temperature of about $-50°$ C. to $-70°$ C.

The cyclodehydration of oxothioether 5 to benzo[b]thiophene 9 is accomplished directly by employing a strong acid such as for example, "super" polyphosphoric acid, i.e., a mixture of phosphorus pentoxide and polyphosphoric acid in the ratio of 1 part by weight (g) of the former to about 4 to 7 parts by volume (ml) of the latter, at an elevated temperature within the range of from about 130° C. to about 170° C. The proportion of oxothioether 5 to "super" polyphosphoric acid is not narrowly critical. It is desirable, however, to use about 6 to about 10 parts by volume (ml) of polyphosphoric acid to 1 part by weight (g) of 5.

To prepare the carboxy- and alkoxycarbonylthioethers 6, the thiophenol 3 is alkylated with a compound of the formula

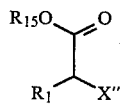

16 wherein $R_{15}$ is hydrogen or lower alkyl and $R_1$ and X" are hereinbefore described. The alkylation is performed under reaction conditions substantially similar to those employed for the conversion of 3 to 5, i.e., in the presence of an alkali metal hydride suspended in a polar aprotic solvent. Acidification is required in the case where $R_{15}$ is hydrogen to neutralize the resulting salt formed by use of excess hydride. The alkoxycarbonylthioethers 6 formed when $R_{15}$ of the alkylating agent 16 is loweralkyl are hydrolyzed to the corresponding carboxylic acids by methods well known in the art such as, for example, by means of potassium hydroxide in ethanol.

In the next step of the intermediate sequence, the carboxythioether 6 is converted into the corresponding acyl halide (bromide or chloride) and cyclized by means of a Friedel-Crafts reagent to the benzo[b]thiophenone 7. The acyl halide is formed by treating 6 (wherein $R_{15}$ is hydrogen) with a thionyl halide (bromide or chloride) in an inert halocarbon solvent such as, for example, methylene chloride or chloroform. While the acyl halide may be isolated from the reaction mixture prior to cyclization, it is preferred to perform the conversion of 6 to 7 without isolation. The cyclization is conveniently performed in the aforementioned halocarbon solvent with a conventional Friedel-Crafts catalyst such as, for example, aluminum chloride, zinc bromide or stannic chloride. Aluminum chloride and methylene chloride are preferred.

The benzo[b]thiophenones 7 exist in tautomeric equilibrium with the 3-hydroxybenzo[b]thiophenes 7A. The carbonyl tautomer 7 is directly convertible to dihydrohydroxybenzo[b]thiophene 8, the dynamic equilibrium being continually displaced in the direction of carbonyl tautomer as the subsequent reaction proceeds.

To prepare dihydrohydroxybenzo[b]thiophenes 8 wherein $R_2$ is hydrogen, the tautomeric compound (7⇌7A) is reduced with an alkali metal borohydride such as, for example, sodium or potassium borohydride in a lower alkanol such as, for example, ethanol or i-propanol. Sodium borohydride in ethanol is the preferred reducing system. To prepare dihydrohydroxybenz[b]thiophenes 8 wherein $R_2$ is a group as hereinbefore defined other than hydrogen, the tautomeric compound (7⇌7A) is treated with Grignard reagent of the formula

wherein $R_2$ is a group as hereinbefore defined other than hydrogen by procedures described in the art. See M.S. Kharasch, "Grignard Reactions of Nonmetallic Substances, Prentice Hall, New York, N.Y., 1954, Chapter 6.

The last step in the intermediate sequence involves the dehydration of alcohol 8 to benzo[b]thiophene 9. This transformation is appropriately performed by treating 8 with a Lewis acid such as, for example, boron trifluoride etherate, in a suitable solvent such as, for example, glacial acetic acid, at a temperature from about 25° C. to about 100° C.

The final steps of the process for the synthesis of the compounds of the present invention include the elaboration of the phenolic side-chain of benzo[b]thiophene 10, prepared by cleavage of the alkoxy moiety of 9, and the oxidation of the thio function of 11 to the sulfone 12 and sulfoxide 13. The alkoxy cleavage is effected by heating 9 with a pyridine hydrohalide such as, pyridine hydrochloride or picoline hydrobromide at an elevated temperature within the range of about 160° to 210° C. The construction of the side-chain is achieved by alkylating the phenol 10 with a compound of the formula

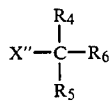

wherein $R_4$, $R_5$ and $X''$ are as hereinbefore defined and $R_6$ is lower alkoxycarbonyl utilizing an alkali metal carbonate or bicarbonate such as potassium carbonate or sodium bicarbonate in a suitable solvent. Included among suitable solvents are acetone, 2-propanone, 2-butanone and the like, and combinations thereof. The combination of potassium carbonate and 2-butanone-dimethylformamide is particularly effective in this process. The alkylation temperature is not critical. However, to promte a reasonable reaction rate, it is preferred to perform the reaction at a temperature from about 50° C. to 100° C. The carboxylic acid esters 11 (wherein $R_6$ is loweralkycarbonyl), so obtained, are hydrolyzed to the corresponding acids 11 (wherein $R_6$ is carboxy) by conventional methods, such as sodium hydroxide or potassium hydroxide in aqueous ethanol. The hydroxamic acid 11 (wherein $R_6$ is hydroamino) may also be prepared by conventional methods from the carboxylic esters 11 by utilizing hydroxylamine or its hydrohalide salt in a suitable alcoholic solvent such as methanol or ethanol. See, for example, "Rodd's Chemistry of Carbon Compounds," 2nd Ed. S. Coffey, Ed., Vol. I, part C, American Elsevier Publishing Co., Inc., New York, N.Y. 1965, p. 189.

To prepare the benzo[b]thiophene 11 having the hydroxymethyl side-chain, i.e., compound 11 wherein $R_6$ is hydroxymethyl, the carboxylic acid ester group of 11 may be reduced with a complex metal hydride such as, for example, lithium aluminum hydride or diisobutyl aluminum hydride in a suitable solvent. Suitable solvents include ethers such as diethylether, dimethoxyethane, tetrahydrofuran and dioxane. The carboxylic acid group of 11, i.e., the copound wherein $R_6$ is carboxyl, may also be reduced with diborane in a aromatic solvent such as, for example, benzene or toluene, or by one of the borane complexes such as, for example, borane-pyridine or borane-tetrahydrofuran.

The oxidation of benzo[b]thiophene 11 to the 1,1-dioxide 12 is accomplished by contacting 11 with hydrogen peroxide or a peracid such as, for example, peracetic acid, perbenzoic acid, meta-chloropherbenzoic acid or perphthalic acid in suitable organic solvent. Among suitable organic solvents for peracids, there may be mentioned halocarbons, for example, methylene chloride, chloroform and the like, and esters of aliphatic carboxylic acid, for example, methyl formate, ethyl acetate and the like. Among suitable organic solvents for hydrogen peroxide, there may be mentioned carboxylic acid such as, for example, acetic acid, and alkanoles, for example, acetone, 2-butanone and the like. The oxidation proceeds readily at room temperature. The oxidation of 11 to 12 may also be accomplished step-wise, i.e., by first oxidizing 11 to the 1-oxide 13 followed by further oxidation of 13 to the 1,1-dioxide 12. The initial oxidation is effected by means of an alkali metal periodate such as sodium or potassium periodate in an appropriate solvent system. Such systems include aqueous alkanols such as aqueous ethanol and i-propanol and aqueous ketones such as acetone and 2-butanone. The 1-oxides, so obtained, may be oxidized to the corresponding 1,1-dioxide by the hereinbefore described peracid method.

In those cases where the benzo[b]thiophene 11 bears a hydroxyalkoxy side-chain, i.e., in those cases where $R_6$ is hydroxymethyl, it is desirable to mask the hydroxy function with a conventional hydroxy protecting group, such as ester of a lower alkanoic acid selected form the group consisting of formates, acetates, propionates and the like, or ethers of dihydrofuran, dihydropyran and the like, prior to oxidation of the thio group. The esters and ethers may be formed by known methods and may be cleaved under mild acidic conditions.

The process incorporating steps 3 to 5 and 5 to 9 is preferred for the preparation of those compounds of the present invention wherein $R_1$ is lower alky or a group of the formula

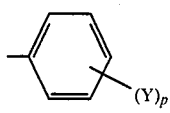

wherein Y and p are as described hereinabefore and $R_2$ is hydrogen; wherein $R_1$ is lower alkyl and $R_2$ is the above phenyl moiety; and wherein $R_1$ and $R_2$ taken together form a group of the formula

—(CH$_2$)$_q$— wherein q is 3,4 or 5, whereas the process incorporating step 4 to 5 and 5 to 9 is preferred for the preparation of these compounds of the instant invention wherein $R_1$ is a group of the formula

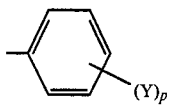

wherein Y and p are as above and $R_2$ is hydrogen, the process for the preparation of the instand benzo[b]thiophenes, incorporating step 3 to 6 is preferred.

The novel compounds of the present invention wherein $R_1$ is lower alkanoyl, formyl, hydroxymethyl or a group of the formula

wherein $R_{19}$ and $R_{20}$ are each independently hydrogen or lower alkyl are prepared from thiophenes 14 and 15 by processes illustrated in Reaction Scheme III.

In the initial step of this sequence, benzo[b]thiophene 15 is converted to the lithio derivative which is condensed with a carbonyl compound of the formula

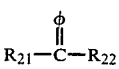
16 wherein $R_{21}$ is hydrogen or lower alkyl and $R_{22}$ is lower alkyl, lower alkoxy, dilower alkylamino or loweralkanoyloxy to benzo[b]thiophene 10 wherein $R_1$ is lower alkanoyl, formyl or a group of the formula

wherein $R_{19}$ and $R_{20}$ are as hereinbefore described. The lithiation is conveniently performed using an alkyllithium such as n-butyllithium in hexane or t-butyllithium in pentane or an aryllithium such as phenyllithium in benzene at a reduced temperature of about −40° to 0° C. n-Butyllithium in hexane is the preferred lithiating agent. The condensation is generally accomplished by contacting the lithio derivative, so formed, with the carbonyl compound in an ethereal cosolvent at a reduced temperature within the aforementioned range. Among ethereal cosolvents, there may be mentioned diethyl ether, dioxane and tetrahydrofuran, tetrahydrofuran being preferred. Among carbonyl compounds, there may be mentioned aldehydes such as formaldehyde, acetaldehyde, propionaldehyde and the like, ketones such as acetone, 2-butanone and the like, esters such as ethyl acetate, methyl propionate and the like, amides such as dimethylacetamide, dimethylformamide and the like, and anhydrides such as acetic anhydride, propionic anhydride and the like.

Alternatively benzo[b]thiophene 14 is lithiated and the lithio derivative is condensed with a carbonyl compound 16 by processes hereinbefore described to provide benzo[b]thiophene 9 which is dealkylated to 10 by procedures disclosed hereinbefore.

When an aldehyde or ketone, i.e., a carbonyl compound of formula 16 wherein $R_{21}$ is hydrogen or lower alkyl and $R_{22}$ is lower alkyl, is employed as the condensing agent benzo[b]thiophenes 9 and 10 wherein $R_1$ is a hydroxymethyl group of the formula

wherein $R_{19}$ and $R_{20}$ are each independently hydrogen or lower alkyl are formed. When an ester, amide or anhydride, i.e., a carbonyl compound of formula 16 wherein $R_{21}$ is hydrogen or lower alkyl and $R_{22}$ is lower alkoxy, dilower alkylamino or lower alkanoyloxy, is utilized as the condensing agent benzo[b]thiophenes 9 and 10 wherein $R_1$ is lower alkanoyl is obtained.

Benzo[b]thiophenes 9 and 10 wherein $R_1$ is lower alkanoyl are reduced to benzo[b]thiophenes 9 and 10 wherein $R_1$ is hydroxymethyl or a group of the formula

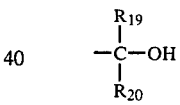

wherein $R_{19}$ and $R_{20}$ are each independently hydrogen or lower alkyl by alkali metal borohydrides such as sodium borohydride or potassium borohydride in an alkanol such as aqueous ethanol or 2-propanol. Sodium borohydride and aqueous ethanol are preferred.

The final step, the elaboration of the phenolic sidechain of benzo[b]thiophene 10, is effected by techniques described hereinbefore, particularly on pages 11 and 12 of the specification.

Benzo[b]thiophene 11 wherein $R_1$ is a group of the formula

wherein $R_{19}$ is hydrogen and $R_{20}$ is lower alkyl are oxidized to benzo[b]thiophene 11 wherein $R_1$ is lower alkanoyl. The oxidation is generally performed by means of a chromium compound such as chromic acid or sodium or potassium dichromate in a suitable organic solvent such as pyridine or glacial acetic acid. Potassium dichromate in glacial acetic acid is the preferred oxidizing agent. The temperatures at which the oxidation is performed is not narrowly critical. However, reduced temperatures within the range of about 0° to about 40° C. are usually preferred to minimize side reactions.

The Benzo[b]thiophene of the present invention are useful as anti-hypertensives and diuretics due to their ability o reduce blood pressure and to produce diuresis, respectively, in mammals. Antihypertensive activity is measured in the spontaneous hypertensive rat by the indirect tall cuff method described by A. Schwartz, Ed., "Methods in Pharmacology," Vol. 1, Appleton-Centry-Crofts, New York, N.y., 1971, page 135. According to this procedure, the test compound is administered orally to a group of 5 rats for 3 days in relation to a control group of the same number. The decrease in blood pressure is measured on the third day of administration. The antihypertensive activity expressed as the decrease in mean arterial blood pressure (mm of mercury) in this procedure of some of the compounds of the present invention is presented in Table I.

TABLE I

| COMPOUND | DOSE (mg/kg of body weight) | BLOOD PRESSURE DECREASE (mm/mercury) |
| --- | --- | --- |
| [(6,7-dichloro-2-methylbenzo[b]thien-5-yl)oxy]acetic acid | 50 | 51 |
| [(6,7-dichloro-2-ethylbenzo[b]thien-5-yl)oxy]acetic acid | 50 | 41 |
| [(6,7-dichloro-2-isopropylbenzo[b]thien-5-yl)oxy]acetic acid | 50 | 41 |
| ethyl [(6,7-dichloro-2-isopropylbenzo[b]thien-5-yl)oxy]acetate | 50 | 35 |
| [(6,7-dichloro-2-cyclopentyl-5-methoxybenzo[b]thiophene | 50 | 43 |
| [(6,7-dichloro-2-isopropylbenzo[b]thien-5-yl)oxy]acetic acid, 1, 1-dioxide | 50 | 33 |
| {[6-chloro-3-(2-fluorophenyl)benzo[b]thien-6-yl]oxy}acetic acid | 50 | 32 |
| [(6,7-dichloro-2-cyclopentylbenzo[b]thien-5-yl)oxy]acetic acid | 50 | 31 |
| 6,7-dichloro-2-cyclopentyl-5-methoxy[b]thiophene | 50 | 43 |
| L-3-(3,4-dihydroxyphenyl)-2-methylalanine | 50 | 40 |

Blood pressure reduction is achieved when the present benzo[b]thiophenes are administered to a subject requiring such treatment as an effective oral, parenteral or intravenous dose of from 0.01 to 100 mg/kg of body weight per day. A preferred effective dose within this range is from about 10 to about 50 mg/kg of body weight per day. A particularly preferred effective amount is about 25 mg/kg of body weight per day. It is to be understood, however, that for any particular subject, specific dosage regimens should be adjusted according to the individual need and the professional judgment of the person administering or supervising the administration of the aforesaid compounds. It is to be further understood that the dosages set forth herein are exemplary only and that they do not, to any extent, limit the scope or practice of the invention.

Diuretic activity is determined in rats by a method similar to that described by C. M. Kazawa and M. J. Kalm, Arch. Intern. Pharmacodyn., 137, 241 (1962). The test compound is administered orally to a group of rats and the average volume of urine excreted is measured. One gram per kilogram of body weight of urea, a known diuretic agent, is administered orally to a positive control group of rats and the average volume of urine excreted is measured. Diuretic activity expressed as the ratio of the average volume of urine excreted in the test group to the average volume of urine excreted in the control group (a ratio greater than 1 indicates diuretic activity) of some of the instant benzo[b]thiophenes as well as standard diuretics is presented in Table II.

TABLE II

| COMPOUND | DOSE (mg/kg of body weight) | DIURESIS PRODUCTION (test compound volume/urea volume) |
| --- | --- | --- |
| [(6,7-dichloro-2-methylbenzo[b]thien-5-yl)oxy]acetic acid | 64 | 0.8 |
| [(6,7-dichloro-2-ethylbenzo[b]thien-5-yl)oxy]acetic acid | 64 | 2.1 |
| [(6,7-dichloro-2-isopropylbenzo[b]thien-5-yl)oxy]acetic acid | 64 | 2.0 |
| [(6,7-dichloro-3-methyl-2-phenylbenzo[b]thien-5-yl)oxy]acetic acid | 64 | 2.5 |
| [(6,7-dichloro-3-phenylbenzo[b]thien-5-yl)oxy]acetic acid | 64 | 1.4 |
| [(6,7-dichloro-3-(4-chlorophenyl)benzo[b]thien-5-yl)oxy]acetic acid | 64 | 1.1 |
| ethyl [(6,7-dichloro-2-isopropylbenzo[b]thien-5-yl)oxy]acetate | 64 | 1.7 |
| [(6,7-dichloro-2-isopropylbenzo[b]thien-5-yl)oxy]acetic acid | 64 | 2.5 |
| [(6,7-dichloro-2-isopropylbenzo[b]thien-5-yl)oxy]acetic acid 1, 1-dioxide | 64 | 2.3 |
| {[6-chloro-3-(2-fluorophenyl)benzo[b]thien-6-yl]oxy}acetic acid | 64 | 1.5 |
| [(6,7-dichloro-3-methyl-2-phenylbenzo[b]thien-5-yl)oxy]acetic acid 1, 1-dioxide | 64 | 1.1 |
| {[6,7-dichloro-2-(2'-fluorophenyl)benzo[b]thien-5-6l]oxy}acetic acid | 64 | 3.8 |
| {[6,7-dichloro-2-(2'-fluorophenyl)benzo[b]thien-5-yl]oxy}acetic acid | 64 | 2.4 |
| 6,7-dichloro-2-cyclopentyl-5-methoxybenzo[b]thiophene | 64 | 2.6 |
| 4-benzylthio-2,3-dichloroanisole | 64 | 2.7 |
| 2-chloro-3-O—N,N—dimethylthiocarbamylanisole | 64 | 1.3 |
| 2-chloro-3-S—N,N—dimethylthiocarbamylanisole | 64 | 1.0 |
| 1-benzylthio-2,3-dichlorophenoxyacetic acid | 64 | 1.0 |
| α-[(2,3-dichloro-4-methoxy)phenylthio]-2-fluoroacetophenone | 64 | 1.2 |
| ethacrynic acid | 64 | 2.5 |
| tienilic acid | 64 | 1.8 |

Diuresis production is achieved when the present benzo[b]thiophenes are administered to a subject requiring such treatment as an effective oral, parenteral or intravenous dose of from 0.01 to 100 mg/kg of body weight per day. A preferred effective dose within this range is from about 10 to 50 mg/kg of body weight per day. A particularly preferred effective amount is about 25 mg/kg of body weight per day. It is to be understood, however, that for any particular subject, specific dosage regimens should be adjusted according to the individual need and the professional judgment of the person administering or supervising the administration of the aforesaid compound. It is to be further understood that the dosages set forth herein are exemplary only and that they do not, to any extent, limit the scope or practice of the invention. Other examples of compounds of the invention include:

6,7-dichloro-3-cyclopentyl-5-methoxybenzo[b]thiophene
ethyl[6,7-dichloro-3-cyclohexylbenzo[b]thien-5-yl)oxy]acetate
[(6,7-dichloro-2-(4-methoxyphenyl)benzo[b]thien-5-yl)oxy]acetic acid
6,7-dichloro-5-methoxy-3-(4-tolyl)benzo[b]thiophene
[(6,7-dichloro-2-(4-hydroxyphenyl)benzo[b]thien-5-yl)oxy]acetic acid
[6,7-dichloro-3-(2-tolyl)benzo[b]thien-5-yl)oxy]acetic acid
6,7-dichloro-5-methoxy-2-(2-tolyl)benzo[b]thiophene
[(6,7-dichloro-3-(4-tolyl)benzo[b]thien-5-yl)oxy]acetic acid
6,7-dichloro-5-methoxy-2-(4-tolyl)benzo[b]thiophene
[(6,7-dichloro-3-(4-tolyl)benzo[b]thien-5-yl)oxy]acetic acid
[6,7-dichloro-2-(2-fluoro-4-hydroxyphenyl)benzo[b]thien-5-yl)oxy]acetic acid
{[6-chloro-3-(2,4-difluorophenyl)benzo[b]thien-6-yl]oxy}acetic acid
ethyl[(6,7-dichloro-2-(2,4-difluorophenyl)benzo[b]thien-5-yl)oxy]acetate
5,6-dichloro-2,3-dihydro-7-methoxy-1H-benzo[b]cyclopental[d]thiophene
ethyl[(3,4-dichloro-7,8,9,10-tetrahydro-6H-benzo[b]cyclohepta[d]thien-2-yl)oxy]acetate
[6,7-dichloro-3-phenylbenzo[b]thien-5-yl)oxy]-2-methylacetic acid
[6,7-dichloro-3-phenylbenzo[b]thien-5-yl)oxy]ethanol
[6,7-dichloro-3-phenylbenzo[b]thien-5-yl)oxy]acetone
5-methoxy-3-phenylbenzo[b]thiophene
[(7-methyl-3-phenylbenzo[b]thien-5-yl)oxy]acetic acid
[6,7-dichloro-3-phenylbenzo[b]thien-5-yl)oxy]-N-hydroxyacetamide
6,7-dichloro-5-methoxy-2-(2-tolyl)benzo[b]thiophene-3(2H)-one
2-(2-chlorophenyl)-6,7-dichloro-5-methoxy-benzo[b]thiophene-3(2H)-one
6,7-dichloro-2-(2,4-dichlorophenyl)-5-methoxybenzo[b]thiophene-3(2H)-one
2,3-dihydro-3-hydroxy-5-methoxybenzo[b]thiophene
2,3-dihydro-3-hydroxy-7-methyl-5-methoxybenzo[b]thiophene
α-[2,3-dichloro-4-methoxyphenylthio)-4-methylacetophenone
3,4-dichloro-2-[(2,3-dichloro-4-methoxy)phenylthio]acetophenone
α-cyclohexyl-2-[2,3-dichloro-4-methoxy)phenylthioacetone
α-cycloheptyl-α-[2,3-dichloro-4-methoxy)phenylthioacetone]
ethylα-(4-methoxyphenylthio)-α-phenylacetate
α-(4-methoxy-2-methylphenylthio)-4-fluoroacetophenone
2,3-dihydro-3-hydroxy-2-(4-methoxyphenyl)benzo[b]thiophene
2,3-dihydro-3-hydroxy-2-(4-hydroxyphenyl)benzo[b]thiophene
2-(4-methoxyphenyl)benzo[b]thiophene-3(2H)-one
2-(4-hydroxyphenyl)benzo[b]thiophene-3(2H)-one
4-methoxy-α-[(2,3-dichloro)phenylthio]acetophenone
α-(2,3-dichlorophenyl)thio-4-hydroxyacetophenone Effective amounts of the benzo[b]thiophenes of the present invention may be administered to a subject by any one of various methods, for example, orally as in capsules or tablets, parenterally in the form of sterile solutions or suspensions, and in some cases intravenously in the form of sterile solutions. Those benzo[b]thiophenes bearing a carboxyl group, while effective themselves, may be formulated and administered in the form of their pharmaceutically acceptable addition salts for purposes of stability, convenience of crystallization, increased solubility and the like.

Preferred pharmaceutically acceptable acid addition salts include alkali metal salts, for example, sodium or potassium salts, alkaline earth metal salts, for example, calcium salts, and complex salts such as, for example, ammonium and substituted ammonium salts. Among the substituted ammonium salts there may be mentioned mono-, di-, or trialkylammonium salts and mono, di, or trihydroxyalkylammonium salts.

The benzo[b]thiophenes of the prsent invention may be administered orally, for example, with an inert diluent or with an edible carrier. They may be enclosed in gelatin capsules or compressed into tablets. For the purpose of oral therapeutic administration, the aforesaid compounds may be incorporated with excipients and used in the form of tablets, troches, capsules, elixirs, suspensions, syrups, wafers, chewing gums and the like. These preparations should contain at least 0.5% of the benzo[b]thiophenes of the present invention, but may be varied depending upon the particular form and may conveniently be between 4% to about 70% of the weight of the unit. The amount of present compound in such compositions is such that a suitable dosage will be obtained. Preferred compositions and preparations according to the present invention are prepared so that an oral dosage unit form contains between 1.0–300 milligrams of the benzo[b]thiophene.

The tablets, pills, capsules, troches and the like may also contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate o Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present benzo[b]thiophene, sucrose as a sweetening agent and certain preservatives, dyes and colorings and flavors. Materials used in preparing these various compositions should be pharmaceutically pure and non-toxic in the amounts used.

For the purposes of parenteral therapeutic administration, the benzo[b]thiophenes of the present invention may be incorporated into a solution or suspension. These preparations should contain at least 0.1% of the aforesaid compound, but may be varied to be between 0.5 and about 30% of the weight thereof. The amount of the present compound in such compositions is such that a suitable dosage will be obtained. Preferred compositions and preparations according to the present invention are prepared so that a parenteral dosage unit contains between 0.5 to 100 milligrams of the benzo[b]thiophene.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic.

The dihydrobenzo[b]thiophenes and thiophenols of the present invention are useful as intermediates for the preparation of anti-hypertensive and diuretic benzo[b]-thiophenes.

The present invention is illustrated by the following examples, which illustration is not to be construed as limiting the invention described herein. All temperatures are given in degree centigrade.

EXAMPLE 1

A suspension of 2.0 g of α-[(2,3-dichloro-4-methoxy)-phenylthio]acetophenone, 3 g of phosphorus pentoxide and 20 ml of polyphosphoric acid is stirred at 130° for 1 hour. After cooling, the mixture is quenched with ice-water and the product is extracted into ether. Washing, followed by drying and concentration, gave a tan-colored oil which was purified by column chromatography over silica gel (solvent of elution: ether-hexane 1:1). The purified product solidified to give 1.33 g of 6,7-dichloro-5-methoxy-3-phenylbenzo[b]thiophene as colorless crystals, mp 117°–119°.

ANALYSIS: Calculated for $C_{15}H_{10}Cl_2OS$: 58.26%C, 3.26%H, 10.37%S. Found: 58.06%C, 3.25%H, 10.36%S.

EXAMPLE 2

A mixture of 1.6 mmoles of 6,7-dichloro-5-methoxy-3-phenylbenzo[b]thiophene and 5 g of pyridine hydrochloride is heated at 195° for 30 min. with stirring. The mixture is cooled and triturated with 50 ml of water. The solid material is collected on a filter, air dried and recrystallized from acetone-hexane to give 0.4 g of 6,7-dichloro-5-hydroxy-3-phenylbenzo[b]thiophene as white prisms, mp 157°–159°.

ANALYSIS: Calculated for $C_{14}H_8Cl_2OS$: 58.26%C, 3.26%H, 10.37%S. Found: 58.06%C, 3.25%H, 10.36%S.

EXAMPLE 3

A mixture of 2.7 g of 6,7-dichloro-5-hydroxy-3-phenylbenzo[b]thiophene, 1.6 g of ethyl bromoacetate, 1.3 g of potassium carbonate and 30 ml of dimethylformamide is stirred at 60°–70° for 30 min. The mixture is filtered to remove inorganic salts and the filtrate is concentrated in vacuo to an oily residue. To the residue is added 10 mil of 40% sodium hydroxide and 30 ml of water and the mixture was heated on a steam bath for 30 min. After acidification of the mixture to pH 2, the solid product was extracted into ether, washed and dried. Concentration in vacuo gives 2.6 g of [(6,7-dichloro-3-phenylbenzo[b]thien-5-yl)oxy]acetic acid as crystals which have mp 152°–154° after recrystallization from acetone-hexane.

ANALYSIS: Calculated for $C_{16}H_{10}Cl_2O_3S_2$: 54.40%C, 2.85%H, 20.08%Cl, 9.08%S. Found: 54.58%C, 3.04%H, 19.70%Cl, 8.89%S.

EXAMPLE 4

A mixture of 0.7 g of 6,7-dichloro-2,3-dihydro-3-hydroxy-5-methoxybenzo[b]thiophene, 1 ml of boron trifluoride etherate and 4 ml of glacial acetic acid is heated at 100° for 5 min. Ice is added and the mixture is basified with dilute sodium hydroxide solution. The off-white solid is collected on a filter, air-dried and recrystallized from ether-hexane to give 0.65 g of 6,7-dichloro-5-methoxybenzo[b]thiophene as prisms, mp 103°–104.5°.

ANALYSIS: Calculated for $C_9H_6Cl_2OS$: 46.36%C, 2.59%H, 30.42%Cl. Found: 46.32%C, 2.50%H, 30.20%Cl.

EXAMPLE 5

A mixture of 45 g of 6,7-dichloro-5-methoxybenzo[b]thiophene and 5 g of pyridine hydrochloride is stirred at 180° for 1 hour. The mixture is cooled, triturated with water and extracted thrice with ether. The ether solution is washed with water, dried and concentrated to give 0.42 g of 6,7-dichloro-5-hydroxybenzo[b]thiophene as a tan-colored solid. Recrystallization from acetone-hexane gives prisms, mp 97°–98°.

ANALYSIS: Calculated for $C_8H_4Cl_2OS$: 43.85%C, 1.84%H. Found: 43.67%C, 1.76%H.

EXAMPLE 6

A solution of 3.0 g of 4-chloro-α-[(2,3-dichloro-4-methoxy)phenylthio]acetophenone, 27.1 ml of polyphosphoric acid and 5.4 g of phosphorous pentoxide is stirred and heated at 130° C. for eleven hours. The solution is cooled with an ice-water bath and 30 ml of ice-water is added to the reaction solution. The resulting slurry is extracted with dichloromethane and the fractions combined. The dichloromethane solution is washed with water, dilute sodium bicarbonate solution, water and dried over anhydrous magnesium sulfate. The mixture is filtered and evaporated to a brown solid. The solid is column chromatographed on a silica gel/-hexane column (eluting with 1:1 ether/hexane). The desired fractions are evaporated and the solid recrystallized from acetone to give 1.11 g of 3-(4-chlorophenyl)-6,7-dichlor-5-methoxybenzo[b]thiophene as a white solid, mp 190°–191°.

ANALYSIS: Calculated for $C_{15}H_9Cl_3OS$: 52.42%C, 2.64%H, 30. 5%Cl. Found: 52.49%C, 2.54%H, 30.74%Cl.

EXAMPLE 7

A mixture of 3.6 g of 6,7-dichloro-5-hydroxybenzo[b]thiophene, 3.0 g of ethyl bromoacetate, 1.5 g of potassium carbonate and 40 ml of anhydrous dimethylformamide is stirred at 70°–80° for 16 hours. The cooled mixture is diluted with ice-water (200 g) and the solid collected by filtration. Recrystallization of the crude product from acetone-hexane gives 3.2 g of ethyl [(6,7-dichlorobenzo[b]thien-5-yl)oxy]acetate as yellowish needles, mp 92°–93°.

ANALYSIS: Calculated for $C_{12}H_{10}Cl_2O_3S$: 47.23%C, 3.30%H, 23.24%Cl. Found: 47.25%C, 3.29%H, 23.10%Cl.

EXAMPLE 8

A mixture of 2.7 g of 6,7-dichloro-2-ethyl-2,3-dihydro-3-hydroxy-5-methoxy-benzo[b]thiophene in 10 ml of glacial acetic acid containing 3 ml of boron trifluoride etherate is warmed on a steam bath until a clear solution is formed. The mixture is allowed to stand at room temperature for 1 hour and poured into a chilled solution of dilute sodium hydroxide. Extraction with ether, followed by drying over anhydrous magnesium hydroxide and concentrating in vacuo, gives 2.4 g 6,7-dichloro-2-ethyl-5-methoxybenzo[b]thiophene as yellow needles, mp 73°–74.5°.

ANALYSIS: Calculated for $C_{11}H_{10}Cl_2OS$: 50.58%C, 3.86%H, 27.15%Cl. Found: 50.83%C, 3.83%H, 26.90%Cl.

EXAMPLE 9

A mixture of 2.15 g of 6,7-dichloro-2-ethyl-5-methoxybenzo[b]thiophene and 15 g of pyridine hydrochloride is stirred at 170°–180° C. for 90 min. The mixture is cooled, triturated with water and extracted three times with dichloromethane. The combined organic extracts are washed with water, dried over anhydrous magnesium sulfate and concentrated in vacuo to an oily residue. Purification by column chromatography (silica gel-ether-pentane 50:50) affords 1.5 g of 6,7-dichloro-2-ethyl-5-hydroxybenzo[b]thiophene as off-white crystals, mp 69°–70°.

ANALYSIS: Calculated for $C_{10}H_8Cl_2OS$: 48.60%C, 3.26%H, 12.97%S. Found: 48.50%C, 3.16%H, 12.95%S.

EXAMPLE 10

A mixture of 1.15 g of 6,7-dichloro-2-ethyl-5-hydroxybenzo[b]thiophene, 0.87 g of ethyl bromoacetate, 0.4 g of potassium carbonate and 12 ml of dimethylformamide is stirred at 90° for 20 min. The cooled mixture is diluted with 100 g of ice water and the solid collected by filtration. Recrystallization of the crude product from pentane gives 1.3 g of ethyl [(6,7-dichloro-2-ethyl-benzo[b]thien-5-yl)oxy]acetate as colorless prisms, mp 67°–68°.

ANALYSIS: Calculated for $C_{14}H_{14}Cl_2O_3S$: 50.46%C, 4.23%H, 21.28%Cl. Found: 50.70%C, 4.21%H, 21.40%Cl.

EXAMPLE 11

A mixture of 7.5 g of ethyl [(6,7-dichlorobenzo[b]thien-5-yl oxy]acetate, 15 g of potassium hydroxide pellets, 125 ml of ethanol and 125 ml of water is refluxed for 1 hour. Ethanol is removed under reduced pressure at 60° and the aqueous suspension is acidified with conc hydrochloric acid. The slurry is stirred at room temperature for 30 min. and extracted with ether (3×250 ml-portions). The combined ether extracts are washed with water, dried over anhydrous magnesium sulfate and concentrated in vacuo to give an off-white crystalline mass. Recrystallization of the crude product from acetone-cyclohexane gives 6.5 g of [(6,7-dichlorobenzo[b]thien-5-yl)oxy]acetic acid as an off-white powder, mp 166°–167°.

ANALYSIS: Calculated for $C_{10}H_6Cl_2O_3S$: 43.34%C, 2.18%H, 25.59%Cl, 11.57%S. Found: 43.15%C, 2.06%H, 25.25%Cl, 11.59%.

EXAMPLE 12

A mixture of 200 mg of 3-(4-chlorophenyl)-6,7-dichloro-5-methoxybenzo[b]thiophene and 1.77 g of pyridine hydrochloride is stirred and heated at 195°–205° for two and one half hours. The reaction is cooled and 20 ml of water is added. The resulting solid is collected on a filter and washed with 1N hydrochloric acid. The product is chromatographed on a silica gel-hexane column using 3:1 hexane/ether as elutent. The product is isolated and recrystallized from acetone-hexane to give 150 mg of 6,7-dichloro-3-(4-chlorophenyl)-5-hydroxybenzo[b]thiophene as a white powder, mp 174°–176°.

ANALYSIS: Calculated for $C_{14}H_7Cl_3OS$: 51.01%C, 2.14% H. Found: 51.10%C, 2.18%H.

EXAMPLE 13

A mixture of 1.17 g of ethyl [(6,7-dichlorobenzo[b]thien-5-yl)oxy]acetate, 2.03 g of m-chloropenbenzoic acid and 50 ml of dichloromethane is stirred at room temperature for 7 hours. The mixture is quenched with ice-water, extracted with ether and the organic extracts are washed consecutively with sodium bisulfite solution, sodium bicarbonate solution and water. Drying over anhydrous magnesium sulfate followed by concentration in vacuo, gives a colorless oil which crystallizes on cooling. Recrystallization of the crude product from acetone-hexane give 950 mg of ethyl [(6,7-dichloro-benzo[b]thien-5-yl)oxy]acetate 1,1-dioxide as white prisms, mp 149°–151°.

ANALYSIS: Calculated for: $C_{12}H_{10}Cl_2O_5S$: 42.74%C, 2.99%H, 21.03%Cl, 9.51%S. Found: 43.03%C, 2.94%H, 20.85%Cl, 9.54%S.

EXAMPLE 14

A mixture of 5.0 g of 6,7-dichloro-2,3-dihydro-3-hydroxy-5-methoxy-2-phenylbenzo[b]thiophene, 10 ml of boron trifluoride etherate and 20 ml of glacial acid is refluxed for 1 hour. The mixture is cooled, diluted with water and basified with dil sodium hydroxide solution. Extraction with dichloromethane followed by column chromatography over silica (50% dichloromethane in hexane) gives 1.45 g of 6,7-dichloro-5-methoxy-2-phenylbenzo[b]thiophene, mp 144°–145°.

ANALYSIS:

Calculated for: $C_{15}H_{10}Cl_2OS$: 58.26%C, 3.26%H, 10.37%S. Found: 58.20%C, 3.33%H, 10.27%S.

EXAMPLE 15

A mixture of 1.2 g of ethyl [(6,7-dichloro-2-ethylbenzo[b]thien-5-yl)oxy]acetate, 2.0 g of 85% potassium hydroxide pellets and 15 ml of ethanol is refluxed for 1 hour. The mixture is concentrated under reduced pressure to a solid residue. Acidification with conc hydrochloric acid, followed by ether extraction and drying, affords 0.95 g of an amorphous solid. Recrystallization from acetone-hexane gives [(6,7-dichloro-2-ethylbenzo[b]thien-5-yl]acetic acid as long needles, mp 179°–181°.

ANALYSIS: Calculated for $C_{12}H_{10}Cl_2O_3S$: 47.22%C, 3.30%H, 23.24%Cl, 10.51%S. Found: 47.21%C, 3.24%H, 23.39%Cl, 10.64%S.

EXAMPLE 16

A solution of 5.0 g of 3-(4-chlorophenyl)-6,7-dichloro-5-hydroxybenzo[b]thiophene, 2.89 g, of ethyl bromoacetate, 2.1 g of potassium carbonate and 64 ml of dimethylformamide is stirred at 80°–90° for thirty minutes. The reaction mixture is worked up adding ice and 125 ml of water to the solution. A tan precipitate is obtained. The precipitate is washed with water, dissolved in dichloromethane and dried over anhydrous magnesium sulfate. The solution is filtered and evaporated. The solid is dissolved in chloroform and chromatographed on an aluminum column eluted with diethyl ether. The isolated product is washed with pentane and the white solid dried to give 3.86 g of ethyl [(6,7-dichloro-3-(4-chlorophenyl benzo[b]thien-5-yl)oxy]acetate, mp 120°–122°. An analytical sample is prepared by recrystallization from absolute ethanol.

ANALYSIS: Calculated for $C_{18}H_{13}Cl_3O_3S$: 52.00%C, 3.15%H, 25.59%Cl. Found: 51.77%C, 3.17%H, 25.34%Cl.

EXAMPLE 17

A solution of 3.65 g of ethyl [6,7-dichloro-3-(4-chlorophenyl)benzo[b]thien-5-yl)oxy]acetate, 76 ml of water, 25 ml of 10N sodium hydroxide solution and 150 ml of 95% ethanol is heated on a steam bath for thirty minutes. The solution is evaporated to a wet solid which is diluted with 250 ml of water and acidified with conc hydrochloric acid. The acidic solution is evaporated and extracted with ether. The ether fractions are combined, washed with water, dried over anhydrous magnesium sulfate, filtered and evaporated to a white solid. The white solid is triturated with 5% acetone-hexane solution and dried to give 3.2 g of [(6,7-dichloro3-(4-chlorophenyl)benzo[b]thien-5-yl)oxy]acetic acid, mp 206°–208°. An analytical sample is recrystallized from acetone-hexane.

ANALYSIS: Calculated for $C_{16}H_9Cl_3O_5$: 49.57%C, 2.34%H, 27.44%Cl. Found: 49.47%C, 2.29%H, 27.14Cl.

EXAMPLE 18

A mixture of 5.5 g of [(6,7-dichlorobenzo[b]thien-5-yl)oxy]acetic acid and 10.1 g of 85% m-chloroperbenzoic acid in 500 ml of chloroform is warmed briefly on a steam bath and stirred at room temperature overnight. The mixture is evaporated to dryness and to the residue is added 100 ml of dichloromethane. After standing in the cold for a few hours, the crystalline material is collected on a filter and recrystallized from ethyl acetate to give 4.9 g of [(6,7-dichlorobenzo[b]thien-5-yl)oxy]acetic acid 1,1-dioxide as rhombic crystals, mp 227°–228°.

ANALYSIS: Calculated for $C_{10}H_6Cl_2O_5S$: 38.85%C, 1.96%H, 22.94%Cl, 10.37%S. Found: 38.93%C, 1.90%H, 22.75%Cl, 10.57%S.

EXAMPLE 19

A 300 mg sample of ethyl [(6,7-dichloro-3-(4-chlorophenyl)benzo[b]thien-5-yl)oxy]acetate is dissolved in 20 ml of dichloromethane and 0.42 g of m-chloroper benzoic acid is added in portions. The reaction is stirred at 25° for 72 hours. The reaction is worked up by quenching it with water, separating the dichloromethane layer from the water layer washing the dichloromethane extract with dilute sodium bicarbonate solution and drying it over anhydrous magnesium sulfate. The solution is filtered, evaporated and column chromatographed on a silica gel/hexane column with a 10–50% methanol/1:1 ether-hexane solution used as eluant. The product is isolated by evaporation and recrystallized from acetone-hexane to give 0.22 g of ethyl [(6,7-dichloro-3-(4-chlorophenyl)benzo[b]thien-5-yl)oxy]acetate 1,1-dioxide as white needles, mp 170°–172°.

ANALYSIS: Calculated for $C_{18}H_{13}Cl_3O_5S$: 48.28%C, 2.93%H, 23.76%Cl. Found: 48.17%C, 2.95%H, 23.57%Cl.

EXAMPLE 20

A solution of 3.7 g of 6,7-dichloro-2,3-dihydro-3-hydroxy-5-methoxy-2-methylbenzo[b]thiophene in 20 ml of glacial acetic acid containing 5 ml of boron trifluoride etherate is warmed on a steam bath for 5 min. to form a clear solution. After stirring at room temperature for 1 hour, the solution is poured into an ice-cold solution of 10% sodium hydroxide. The organic materials are extracted 3 times with ether, dried and concentrated under vacuum. The reddish brown residue is purified by dissolving it in ether and passing it through an alumina column packed with ether. Elution with ether gives 2.1 g of 6,7-dichloro-5-methoxy-2-methylbenzo[b]thiophene as off-white crystals, mp 113°–114°.

ANALYSIS: Calculated for $C_{10}H_8Cl_2OS$: 48.59%, 3.26%H, 12.97%S. Found: 48.63%C, 3.26%H, 12.81%S.

EXAMPLE 21

A dehydrating mixture of "super" polyphosphoric acid is prepared by mixing 45 g of polyphosphoric acid with 10 g of phosphorus pentoxide. To this rapidly stirred mixture, at 170°, is added 7.5 g of α-[(2,3-dichloro-4-methoxy)phenylthio]acetone in small portions. Following the addition, the reaction mixture is stirred at 170°–180° for an additional 30 min. The mixtures is cooled, quenched with water and extracted 3 times with ether. The ether solution is washed, dried over anhydrous magnesium sulfate and concentrated in vacuo to give a tan-colored residue. Recrystallization of the crude product from boiling hexane affords 6.0 g of 6,7-dichloro-5-methoxy-3-methylbenzo[b]thiophene as yellowish prisms, mp 122°–124°.

ANALYSIS: Calculated for $C_{10}H_8Cl_2OS$: 48.59%C, 3.26%H, 12.97%S. Found: 48.43%C, 3.29%H, 12.04%S.

EXAMPLE 22

A mixture of 5.6 g of 6,7-dichloro-5-methoxy-3-methylbenzo[b]thiophene and 50 g of pyridine hydrochloride is stirred at 190°–195° for 2 hours. The cooled reaction mixture is diluted with water and extracted with three 300 ml-portions of ether. The combined ether extracts are washed, dried and concentrated to give a tan-colored solid, mp 137°–139°. Recrystallization from hexane gives 3.8 g of 6,7-dichloro-5-hydroxy-3-methylbenzo[b]thiophene as silky needles.

ANALYSIS: Calculated for $C_9H_6Cl_2OS$: 46.37%C, 2.59%H. Found: 46.50%C, 2.60%H.

EXAMPLE 23

A mixture of 3.7 g of 6,7-dichloro-5-hydroxy-3-methylbenzo[b]thiophene, 4.3 g of ethyl bromoacetate and 20 ml of 2-butanone containing 5 ml of dimethylformamide is stirred at 60°–70° for 2 hours. The cooled mixture is diluted with ice-water and extracted 3 times with ether. The combined ether extract is dried over anhydrous magnesium sulfate and concentrated under vacuum to a brownish oil. Purification of the crude product is effected by column chromatography (alumina/ether). The purified ester is recrystallized from ether-pentane to give 4.3 g of ethyl [(6,7-dichloro-3-methylbenzo[b]thien-5-yl)oxy]acetate as fluffy needles, mp 115°–117°.

ANALYSIS: Calculated for $C_{13}H_{12}Cl_2O_3S$: 48.91%C, 3.79%H, 10.05%S. Found: 48.95%C, 3.67%H, 10.06%S.

EXAMPLE 24

A mixture of 4.0 g of ethyl [(6,7-dichloro-3-methylbenzo[b]thien-5-yl)oxy]acetate, 6.8 g of potassium hydroxide in 25 ml of ethanol and 25 ml of water is heated on a steam bath for a few minutes until a clear solution is formed. The mixture is cooled (solid forms), acidified with conc hydrochloric acid and extracted with ether, followed by washing and drying to give 3.2 of [6,7-dichloro-3-methylbenzo[b]thien-5-yl)oxy]acetic acid as fluffy needles, mp 205°-206°.

ANALYSIS: Calculated for $C_{11}H_8Cl_2O_3S$: 45.37%C, 2.77%H, 24.36%Cl, 11.01%S. Found: 45.30%C, 2.70%H, 23.99%Cl, 11.11%S.

EXAMPLE 25

To a well-stirred mixture of "super" polyphosphoric acid prepared by mixing 5 g of phosphorus pentoxide and 25 g of polyphosphoric acid at 160° is added 4.0 g of α[(2,3-dichloro-4-methoxy)phenylthio]-α-phenylacetone in small portions. Following the addition, the mixture is stirred at 160° for 30 min and allowed to cool. Trituration with water followed by ether extraction and drying affords a brownish solid which is purified by column chromatography over silica gel. Elution with a 50:50 mixture of dichloromethane-hexane gives 2.8 g of 6,7-dichloro-5-methoxy-3-methyl-2-phenylbenzo[b]thiophene as tan-colored crystals, mp 137.5–138°. For analysis, a sample is recrystallized twice from ether-hexane and dried at 100°.

ANALYSIS: Calculated for $C_{16}H_{12}Cl_2OS$: 59.44%C, 3.74%H, 9.92%S. Found: 59.06C, 3.68%H, 9.88%S.

EXAMPLE 26

A mixture of 2.5 g of 6,7-dichloro-5-methoxy-3-methyl-2-phenylbenzo[b]thiophene and 20 g of pyridine hydrochloride is stirred at 185°-190° for 3 hours. The cooled mixture is triturated with water and extracted 3 times with ether. The combined ether extracts is washed with dilute hydrochloric acid, water and dried. Removal of solvent leaves a brownish solid which is purified by passing it through a silica gel column packed in hexane. Elution with 50:50 ether-hexane gave 1.8 g of 6,7-dichloro-5-hydroxy-3-methyl-2-phenylbenzo[b]thiophene as colorless crystals, mp 146°-147°. For analysis, a sample is recrystallized twice from ether-hexane (10% of ether) and dried at 100°.

ANALYSIS: Calculated for $C_{15}H_{10}Cl_2OS$: 58.26%C, 3.26%H, 10.37%S. Found: 58.21%C, 3.25%H, 10.40%S.

EXAMPLE 27

A mixture of 1.5 g of 6,7-dichloro-5-hydroxy-3-methyl-2-phenylbenzo[b]thiophene and 1.1 g of ethyl bromoacetate, 1.0 g of potassium carbonate in 15 ml of 2-butanone containing 2 ml of dimethylformamide is refluxed for 16 hours. The cooled mixture is diluted with water, extracted 3 times with ether and dried. Removal of solvent under reduced pressure leaves 1.8 g of off-white solid which is recrystallized from ether-hexane to give 1.6 g of ethyl[6,7-dichloro-3-methyl-2-phenylbenzo[b]thien-5-yl)oxy]acetate as needles, mp 137°-138°.

ANALYSIS: Calculated for $C_{19}H_{16}Cl_2O_3S$: 57.73%C, 4.08%H, 17.94%Cl. Found: 57.85%C, 4.06%H, 17.80%Cl.

EXAMPLE 28

A mixture of 1.5 g ethyl[(6,7-dichloro-3-methyl-2-phenylbenzo[b]thien-5-yl)oxy]acetate in 50 ml of 95% ethanol and 50 ml of 15% aqueous sodium hydroxide is stirred under reflux for 1 hour. The mixture is concentrated under vacuum to dryness. The residue is triturated with water, cooled to 0° and acidified with conc hydrochloric acid. The solid product is extracted exhaustively with a mixture of ethyl ether-ethyl acetate (1:1) and the ether extracts are washed and dried over anhydrous magnesium sulfate. Removal of the solvents under reduced pressure leaves a tan-colored residue which is recrystallized from acetone to give 1.24 g of [(6,7-dichloro-3-methyl-2-phenylbenzo[b]thien-5-yl)oxy]acetic acid as shiny platelets, mp 232°-233° C.

ANALYSIS: Calculated for $C_{17}H_{12}Cl_2O_3S$: 55.59%C, 3.29%H, 19.31%Cl. Found: 55.61%C, 3.34%H, 18.93%Cl.

EXAMPLE 29

A mixture of 52 ml of polyphosphoric acid and 10.3 g of phosphorous pentoxide is heated to 155°. α-[2,3-Dichloro-4-methoxyphenylthien]-4-fluoroacetophenone, (5.47 g) is sprinkled on the solution and the resulting solution is stirred at 145°-155° for two hours. The reaction is worked up by stirring it with 150 ml of ice-water and extracting the aqueous solution with dichloromethane. The dichloromethane fractions are combined, washed with water, dil sodium bicarbonate solution and water and dried over anhydrous magnesium sulfate. The solution is filtered, evaporated and the remaining solid is chromatographed on an alumina/diethylether column with ether being used as the eluant to give 2.72 g 6,7-dichloro-3-(4-fluorophenyl)-5-methoxybenzo[b]thiophene. An analytical sample is recrystallized from acetone to give product with a mp 141°-143°.

ANALYSIS: Calculated for $C_{15}H_9Cl_2FOS$: 55.06%C, 2.77%H, 21.67%Cl. Found: 54.88%C, 2.81%H, 21.43%Cl.

EXAMPLE 30

A mixture of "super" polyphosphoric acid is freshly prepared by mixing 7.0 g of phosphorous pentoxide and 40 g of polyphosphoric acid. The mixture is heated to 135°-140° and, with efficient stirring, is added 5.5 g of finely pulverized 2-[2,3-dichloro-4-methoxyphenylthio]cyclohexanone. Stirring is continued at 140° for 2 hours and the mixture is cooled, diluted with water and filtered. The crude product is filtered, air-dried and purified by passing it through a silica column. Elution with ether-hexane (50:50) yields 4.3 g of 3,4-dichloro-6,7,8,9-tetrahydro-2-methoxydibenzothiophene as off-white crystals, mp 123°-125°.

ANALYSIS: Calculated for $C_{13}H_{12}Cl_2OS$: 54.36%C, 4.21%H, 24.69%Cl. Found: 54.22%C, 4.24%H, 24.88%Cl.

EXAMPLE 31

A mixture of 4.2 g of 3,4-dichloro-6,7,8,9-tetrahydro-2-methoxydibenzothiophene and 40 g of pyridine hydrochloride is stirred at 190°-195° under nitrogen for 2 hours. The cooled mixture is triturated with water and the solid product is collected. Recrystallization from ether-pentane after decolorization with charcoal gave 3.6 g of 3,4-dichloro-6,7,8,9-tetrahydro-2-hydroxydibenzothiophene as off-white crystals, mp 103°-105°.

ANALYSIS: Calculated for $C_{12}H_{10}Cl_2OS$: 52.76%C, 3.69%H, 11.74%S. Found: 52.63%C, 3.67%H, 11.85%S.

EXAMPLE 32

A mixture of 3.5 g of 3,4-dichloro-6,7,8,9-tetrahydro-2-hydroxydibenzothiophene, 2.6 g of ethyl bromoacetate and 2.2 g of potassium carbonate in 20 ml of 2-butanone containing 2 ml of dimethyl formamide is refluxed overnight. The mixture is diluted with 200 ml of chloroform, washed with water, dried and concentrated to give 3.8 g of solid residue. Recrystallization of the crude product from acetone gave 3.2 g of ethyl[(3,4-dichloro-6,7,8,9-tetrahydrodibenzothien-2-yl)oxy]acetate as colorless prisms, mp 157°–159°.

ANALYSIS: Calculated for $C_{16}H_{16}Cl_2O_3S$: 53.49%C, 4.49%H, 8.93%S. Found: 53.45%C, 4.51%H, 8.98%S.

EXAMPLE 33

A suspension of 3.2 g of ethyl[(3,4-dichloro-6,7,8,9-tetrahydrodibenzothien-2-yl)oxy]acetate in 30 ml of 95% ethanol and 300 ml of 20% sodium hydroxide solution is stirred at reflux for 2 hours. The mixture is cooled, acidified with conc. hydrochloric acid and the resultant suspension is stirred in the cold for 30 minutes before filtration. The air dried product is recrystallized from 70 or 95% ethanol to give 2.41 g of [(3,4-dichloro-6,7,8,9-tetrahydrobenzothien-2-yl)oxy]acetic acid as fine needles, mp 257°–259°.

ANALYSIS: Calculated for $C_{14}H_{12}Cl_2O_3S$: 50.76%C, 3.65%H, 21.41%Cl, 9.68%S. Found: 50.80%C, 3.76%H, 21.03%Cl, 9.54%S.

EXAMPLE 34

A suspension of 3.6 g of [(3,4-dichloro-6,7,8,9-tetrahydrodibenzothien-2-yl)oxy]acetic acid, 5.74 g of 85% m-chloropenbenzoic acid and 120 ml of ethyl acetate is stirred under reflux for 16 hours. The cooled mixture is concentrated to dryness and the residue is triturated with 20 ml of dichloromethane and filtered. The crude product is recrystallized twice from ethanol and heated at 100° in vacuo to give 2.5 g of [(3,4-dichloro-6,7,8,9-tetrahydrodibenzothien-2-yl)oxy]acetic acid 5,5-dioxide as which crystals, mp 264–265.

ANALYSIS: Calculated for $C_{14}H_{12}Cl_2O_5S$: 46.29%C, 3.33%H. Found: 46.21%C, 3.38%H.

EXAMPLE 35

To 28.4 g of 6,7-dichloro-2,3-dihydro-3-hydroxy-2-isopropyl-5-methoxybenzo[b]thiophene in 139 ml of glacial acetic acid is added 35 ml of boron trifluoride etherate. The reaction is heated on a steam bath for 10 minutes and allowed to stir at room temperature for 90 min. The reaction is poured into a mixture of 250 ml of 10% sodium hydroxide solution and 150 ml of ice. The mixture is basified with 50% sodium hydroxide solution, diluted with 600 ml of water and extracted with four 300 ml-portions of ether. The combined ether extracts are washed with one 350 ml-portion of water, one 150 ml-portion of saturated sodium chloride solution and dried over magnesium sulfate to give 26.4 g of a clear, brown oil of high purity by thin-layer chromatography. A 10 g-portion of the oil is chromatographed on 500 ml of silica gel with ether:hexane (1:2) to give 9.55 g of 6,7-dichloro-2-isopropyl-5-methoxybenzo[b]thiophene as a clear, colorless oil which solidified to a low melting solid, mp <37°, pure by thin-layer chromatography (silica gel, 1:1, ether-hexane or carbon tetrachloride).

ANALYSIS: Calculated for $C_{12}H_{12}Cl_2OS$: 52.39%C, 4.40%H. Found: 52.03%C, 4.31%H.

EXAMPLE 36

A mixture of 6.00 g of 6,7-dichloro-2-isopropyl-5-methoxybenzo[b]thiophene and 50 g of pyridine hydrochloride, is heated under nitrogen with stirring in a 185° bath for 4.5 hours and at 200° for one hour. The reaction is cooled, triturated with 500 ml of water and extracted with three 150 ml-portions of ether. The combined ether extracts are washed with one 150 ml-portion of 2N hydrochloric acid, two 150 ml-portions of water and one 50 ml-portion of saturated sodium chloride solution and dried over magnesium sulfate to give 5.61 g of 6,7-dichloro-5-hydroxy-2-isopropylbenzo[b]thiophene as an amber oil which crystallized on standing to a product having mp 44.5–46.5. A sample recrystallized twice from hexane melts at 44.5°–46.5°.

ANALYSIS: Calculated for $C_{11}H_{10}Cl_2OS$: 50.60%C, 3.86%H. Found: 50.56%C, 3.91%H.

EXAMPLE 37

To 16.3 g of 6,7-dichloro-5-hydroxy-2-isopropylbenzo[b]thiophene and 12.53 g of ethyl bromoacetate in 150 ml of 2-butanone in 15 ml of dimethylformamide is added 11 g of potassium carbonate. The reaction is heated in an 80°–90° bath for 18 hours. The reaction is filtered and the volume reduced to 75 ml. The solution is diluted with 750 ml of water and extracted with 200 ml of ether. The aqueous layer is extracted additionally with two 200 ml portions of ether and the combined ethereal extracts are washed with two 300 ml portions of water, one 50 ml portion of saturated sodium chloride solution and dried over magnesium sulfate to give 22.54 g of yellow-tan needles. The crystals are mixed with 50 ml of boiling pentane, cooled to 0°, filtered and washed to give 20.48 g of ethyl[(6,7-dichloro-2-isopropylbenzo[b]thien-5-yl)oxy]acetate as tan needles, mp 74°–77°. A sample recrystallized twice from ether-pentane at 76°–77.5°.

ANALYSIS: Calculated for $C_{15}H_{16}Cl_2O_3S$: 51.89%C, 4.65%H. Found: 51.74%C, 4.62%N.

EXAMPLE 38

A mixture of 4.8 g of 6,7-dichloro-5-methoxy-2-methylbenzo[b]thiophene and 40 g of pyridine hydrochloride is stirred at 190° for 3 hours. The cooled mixture is diluted with 500 ml of water. The solid is collected and air-dried. Recrystallization from ether-hexane mixture gives 6,7-dichloro-5-hydroxy 2-methylbenzo[b]thiophene as off-white crystals, mp 93°–95° C.

ANALYSIS: Calculated for $C_9H_6Cl_2OS$: 46.37%C, 2.59%H. Found: 46.54%C, 2.52%H.

EXAMPLE 39

A mixture of 2.1 g of 6,7-dichloro-5-hydroxy-2-methylbenzo[b]thiophene, 1.88 g of ethyl bromoacetate, 2-butanone, 2 ml of dimethylformamide and 4.0 g of sodium bicarbonate is refluxed for 16 hours. The cooled mixture is diluted with ice, extracted 3 times with ether and the ether solution is washed, dried and concentrated. The crude oil after removal of solvent is purified by passing it through an alumina column. Elution with ether gives 2.7 g of ethyl[(6,7-dichloro-2-methylbenzo[b]thien-5-yl)oxy]acetate as off-white crystals, mp 91°–92°. An analytical sample is recrystallized twice from hexane and dried at 80°.

ANALYSIS: Calculated for $C_{13}H_{12}Cl_2O_3S$: 48.91%C, 3.79%H. Found: 49.03%C, 3.79%H.

EXAMPLE 40

A mixture of 2.6 g of ethyl[(6,7-dichloro-2-methylbenzo[b]thien-5-yl)oxy]acetate in 20 ml of 20% sodium hydroxide solution and 20 ml of ethanol is warmed on a steam bath for 1 hour. The cooled mixture is concentrated in vacuo to remove the ethanol and the aqueous mixture is acidified with conc. hydrochloric acid to pH 2. After stirring at room temperature for 2 hours, the solid collected on a filter, dried and recrystallized from acetone-hexane to give 2.0 g of [(6,7-dichloro-2-methylbenzo[b]thien-5-yl)oxy]acetic acid as white needles, mp 215°–216°.

ANALYSIS: Calculated for $C_{11}H_8Cl_2O_3S$: 45.38%C, 2.77%H. Found: 45.38%C, 2.70%H.

EXAMPLE 41

To 6.94 g of ethyl[(6,7-dichloro-2-isopropylbenzo[b]thien-5-yl)oxy]acetate in 102 ml of hot ethanol is slowly added 102 ml of water, followed by 12.2 g of 85% potassium hydroxide pellets. The suspension is refluxed for one hour. The solvents are evaporated and the residue is diluted with 175 ml of water. Approximately 35 ml of 6N hydrochloric acid is added to give a pH of 1. The mixture is diluted further with 100 ml of water. Extractions with ether and toluene at this stage gives only 1.14 g of the desired acid: the major portion of material (apparently the potassium salt of the product) remains in the extraction interface as a layer of crystals. The crystals are filtered, washed with water and ether and dried to give 5.71 g of salt mp 316°–317°, with decomposition. The salt is converted into the desired product by stirring in a mixture of 200 ml of 2N hydrochloric acid and 150 ml of ethyl acetate for 30 minutes. The layers are separated and the aqueous layer is extracted with an additional 75 ml of ethyl acetate. The combined ethyl acetate extracts are washed with two 75 ml-portions and one 50 ml-portion of water, one 30 ml-portion of brine and dried over anhydrous magnesium sulfate to give 4.95 g of a white solid. The 4.95 g sample and the 1.14 g sample isolated in the initial extraction were recrystallized from acetone-pentane to give 4.5 g of [(6,7-dichloro-2-isopropylbenzo[b]thien-5-yl)oxy]acetic acid as white powder, mp 168°–170°. Recovery from the supernatant gives an additional 1.01 g, mp 167–169, for a total yield of 5.51 g.

ANALYSIS: Calculated for $C_{13}H_{12}Cl_2O_3S$: 48.92%C, 3.79%H, 22.06%Cl. Found: 48.79%C, 3.72%H, 22.07%Cl.

EXAMPLE 42

A mixture of 2.5 g of 6,7-dichloro-2-cyclopentyl-2,3-dihydro-3-hydroxy-5-methoxybenzo[b]thiophene and 10 ml of glacial acetic acid containing 5 ml of boron trifluoride etherate is warmed on a steam bath for 15 minutes and allowed to stand overnight. The mixture is poured into a chilled solution of dilute sodium hydroxide and the organic material is extracted into ether. Washing with water, followed by drying over anhydrous magnesium sulfate and evaporation in vacuo, gives 2.0 g of wax-like crystals. Recrystallization from ether-hexane gives 1.8 g of 6,7-dichloro-2-cyclopentyl-5-methoxybenzo-[b]thiophene as fine needles, mp 59.5°–60°.

ANALYSIS: Calculated for $C_{14}H_{14}Cl_2OS$: 55.80%C, 4.68%H. Found: 55.70%C, 4.68%H.

EXAMPLE 43

A mixture of 6.0 g of 6,7-dichloro-5-methoxy-2-phenylbenzo[b]thiophene and 42 g of pyridine hydrochloride is stirred at 190°–195° for 4 hours. The slightly cooled reaction mixture is poured into a mixture of 800 g of ice and 10 ml of conc. hydrochloric acid. Extraction with ether, followed by washing and drying, yields 5.23 g of 6,7-dichloro-5-hydroxy-2-phenylbenzo[b]thiophene as an off-white solid, mp 122°–124°. Recrystallization from ether-hexane yields prisms, mp 124°–126°.

ANALYSIS: Calculated for $C_{18}H_8Cl_2OS$: 56.96%C, 2.73%H. Found: 56.90%C, 2.64%H.

EXAMPLE 44

A mixture of 5.1 g of 6,7-dichloro-5-hydroxy-2-phenylbenzo[b]thiophene. 3.5 g of ethyl bromoacetate and 5 g of sodium bicarbonate in 100 ml of 2-butanone containing 10 ml of dimethylformamide is stirred at 85°–90° for 16 hours. The mixture is concentrated at reduced pressure to remove the sovents and the residue is triturated with 50 g of ice-water. After 30 minutes the solid is filtered and air dried. Recrystallization from ether-hexane gives 4.7 g of ethyl[(6,7-dichloro-2-phenylbenzo[b]thien-5-yl)oxy]acetate as fine needles, mp 116.5°–117°.

ANALYSIS: Calculated for $C_{18}H_{14}Cl_2O_3S$: 56.70%C, 3.70%H. Found: 56.76%C, 2.65%H.

EXAMPLE 45

A mixture of 4.47 g of ethyl[(6,7-dichloro-2-phenylbenzo[b]thien-5-yl)oxy]acetate and 150 ml of 95% ethanol was treated with 150 ml of 20% sodium hydroxide solution. The mixture is refluxed for 3 hours and concentrated in vacuo to remove ethanol. Acidification at 0°–10°, followed by ether extraction, yields 3.9 g of [(6,7-dichloro-2-phenylbenzo[b]thien-5-yl)oxy]acetic acid as white needles, mp 209°–211°.

ANALYSIS: Calculated for $C_{16}H_{10}Cl_2O_3S$: 54.40%C, 2.85%H. Found: 54.28%C, 2.79%H.

EXAMPLE 46

A mixture of 1.0 g of 6,7-dichloro-5-methoxybenzo[b]thiophien-3(2H)-one and 0.5 g of sodium borohydride in 15 ml of absolute ethanol is stirred at room temperature for 1 hour. The mixture is poured into ice, extracted with ether and dried. Evaporation of the solvent in vacuo gives 0.91 g of 6,7-dichloro-2,3-dihydro-3-hydroxy-5-methoxybenzo[b]thiophene as a greyish solid which is recrystallized from acetone-hexane to give rhombic crystals, mp 122°–124°.

ANALYSIS: Calculated for $C_9H_8Cl_2O_2S$: 43.04%C, 3.21%H, 12.77%S. Found: 43.07%C, 3.17%H, 12.75%S.

EXAMPLE 47

Sodium borohydride (2.5 g) is added, in small portions, to a stirred solution of 5.0 g of 6,7-dichloro-5-methoxy-2-methylbenzo[b]thiophen-3(2H)-one one (5.0 g), in 120 ml of ethanol. Stirring is continued at room temperature for 1 hour and excess solvent is removed under reduced pressure. The residue is triturated with dilute sodium hydroxide solution and extracted 3 times with ether. The combined ether solution is washed thoroughly with water, dried and concentrated. Removal of ether leaves an oily residue which crystallized upon cooling. For analysis, a small sample was washed with pentane and dried at 60° to give 6,7-dichloro-2,3- dihydro-3-hydroxy-5-methoxy-2-methylbenzo[b]thiophene.

ANALYSIS: Calculated for $C_{10}H_{10}Cl_2O_2S$: 45.29%C, 3.80%H, 12.09%S. Found: 45.48%C, 3.81%H, 12.20%S.

EXAMPLE 48

To 6.0 g of α-(2,3-dichloro-4-methoxyphenylthio)isovaleric acid in 27 ml of dry dichloromethane is added 5.5 ml of thionyl chloride. The reaction is heated under reflux for 1 hour and excess reagent is removed under aspirator pressure. The residue is diluted with 70 ml of dichloromethane and the resulting slurry is added over less than one minute to a slurry of 2.79 g of aluminum chloride in 8 ml of dichloromethane at −60°. The cooling bath is removed and the reaction allowed to warm to room temperature over one hour. Stirring is continued for an additional hour and reaction is quenched with 250 ml of water. The mixture is extracted with three 125 ml portions of ether and the combined ether extracts are washed with two 150 ml portions and one 60 ml portion of saturated sodium bicarbonate solution, water and brine and dried over anhydrous magnesium sulfate to give 2.54 g of oily 6,7-dichloro-5-methoxy-2-isopropylbenzo[b]thiophen-3(2H)-one.

A mixture of 2.00 g of the above ketone and 0.9 g of 98% sodium borohydride in 44 ml of absolute ethanol is stirred at room temperature for one hour. The mixture is evaporated to remove solvent, cooled and treated with 150 ml of ice water. The aqueous solution is extracted with three 50 ml of ether. The combined ether extracts are washed with one 100 ml-portion of water and dried over anhydrous magnesium sulfate to give 1.34 g of a yellow oil. The oil crystallized when dissolved in ether and triturated with pentane to give 0.68 g of 6,7-dichloro-2,3-dihydro-3-hydroxy-2-isopropyl-5-methoxybenzo-[b]thiophene as rhombic crystals, mp 119°–123°. The supernatant was evaporated and chromatographed on 50 ml of alumina with ether and 10% methanol-ether to give 0.34 g additional product. A sample of the thrice recrystallized material melted at 125.5°–127°.

ANALYSIS: Calculated for $C_{12}H_{14}Cl_2O_2S$: 49.17%C, 4.81%H. Found: 49.16%C, 4.70%H.

EXAMPLE 49

A mixture of α-(2,3-dichloro-4-methoxy)phenylthio-α-cyclopentyl acetic acid (4.3 g), 10 ml of thionyl chloride and 50 ml of dichloromethane is refluxed for 30 minutes until a homogeneous solution is formed. The cooled solution is concentrated to dryness at 50°, leaving a crystalline acid chloride. The residue is dissolved in 100 ml of dichloromethane, cooled to −50° (with a dry-ice acetone bath) and treated with 1.90 g of aluminum chloride in small portions. The cooling bath is removed after the additional is complete and the reaction mixture is allowed to rise gradually to room temperature. After stirring for 2 hours, the mixture is decomposed with water and the aqueous solution is extracted 3 times with additional portions of dichloromethane. The combined organic solution, after brief drying over anhydrous magnesium sulfate is concentrated under reduced pressure to a dark crystalline residue. To the crude ketone is added 200 ml of absolute ethanol and, with good stirring, 2.5 g of sodium borohydride is added in small portions over 5–10 minutes. The mixture became homogeneous after a few minutes and stirring is continued at ambient temperature for an additional hour. Decomposition with ice, followed by the usual work-up, gives 2.41 g of 6,7-dichloro-2-cyclopentyl-2,3-dihydro-3-hyroxy-5-methoxybenzo[b]thiophene as an epimeric mixture of the desired alcohols. Recrystallization from ether-hexane gives the major isomer which melted at 129°–132° C.

ANALYSIS: Calculated for $C_{14}H_{16}Cl_2O_2S$: 52.62%C, 5.05%H. Found: 52.77%C, 4.99%H.

EXAMPLE 50

To a suspension of 1.35 g of α-[(2,3-dichloro-4-methoxy)phenylthio]acetic acid (1.35 g) in 20 ml of dichloroethane is added 0.8 ml of thionyl chloride and the solution is refluxed for 1 hour whereupon it becomes clear. To the cooled solution is added, portionwise, 800 mg of aluminum chloride and the darkened mixture is stirred at room temperature for 2 additional hours. The mixture is decomposed with water and the organic material is extracted into ether and dried over anhydrous magnesium sulfate. Removal of solvent under reduced pressure leaves a yellowish solid which is recrystallized from ether to give 0.8 g of 6,7-dichloro-5-methoxybenzo[b]thiophen-3(2H)-one, mp 178°–180°.

ANALYSIS: Calculated for $C_9H_6Cl_2O_2S$: 43.39%C, 2.43%H, 28.46%Cl, 12.97%S. Found: 43.59%C, 2.27%H, 28.09%Cl, 13.19%S.

EXAMPLE 51

A solution of 1.17 g of α-(2,3-dichloro-4-methoxyphenylthio)-α-phenylacetic acid in 25 ml of carbon disulfide is refluxed with 0.5 g of thionyl chloride until the solution becomes clear. The solution is cooled to 5° and to it is added, in small portions, 340 mg of aluminum chloride. The mixture is stirred at reflux for 3 additional hours. Ice-water (20 g) is added to quench the reaction mixture and the product is extracted into dichloromethane. The dichloromethane extract is washed with sodium bicarbonate solution, water, dried and concentrated to give a syrup. The oily residue is triturated with 2 ml of acetone and allowed to stand at room temperature. Crystals slowly deposit and are collected after 2 days. Recrystallization from chloroform gives 6,7-dichloro-5-methoxy-2-phenylbenzo[b]thiophen-3(2H)-one as a yellowish solid, mp 228°–229° C.

ANALYSIS: Calculated for $C_{15}H_{10}Cl_2O_2S$: 55.40%C, 3.10%H, 9.86%N, 21.80%Cl. Found: 54.97%C, 2.98%H, 9.68%N, 22.01%Cl.

EXAMPLE 52

A mixture of 9.37 g of 2,3 dichloro-4-methoxybenzenesulfonyl chloride, 72 g of crushed ice, 24 g of conc. sulfuric acid and 12 g of zinc dust is stirred under reflux for 16 hours. The mixture is diluted with dichloromethane, cooled and stirred at room temperature for 2 hours. Filtration removes the unreacted zinc and the organic extracts are washed with water, sodium bicarbonate solution and dried over anhydrous magnesium sulfate. Removal of solvent in vacuo leaves a white solid which is recrystallized from ether-pentane to give 5.5 g of 2,3-dichloro-4-methoxy-thiophenol as colorless needles, mp 81.5°–83°.

ANALYSIS: Calculated for $C_7H_6Cl_2OS$: C 40.21, H 2.89, S 15.34. Found: C 40.20, H 2.86, S 15.44.

EXAMPLE 53

A solution of 6.23 g of 2,3-dichloro-4-methoxythiophenol in 60 ml of sieved-dried dimethylformamide is added to 0.75 g of sodium hydride over a period of 2–3 minutes. After stirring at room temperature for 20 minutes, the yellowish solution is treated with 5.10 g of benzyl bromide at a rate so that the temperature does not rise above 40°. Stirring is continued for an additional 30 minutes. The cloudy mixture is poured onto 200 g of crushed ice with caution and the white precipitate is collected on a filter after 1 hour at 10° C. The air-dried product is recrystallized from acetone-hexane to give 7.8 g of 4-benzylthio-2,3-dichloroanisole as white needles, mp 116°–117° C.

ANALYSIS: Calculated for $C_{14}H_{12}Cl_2OS$: 56.19%C, 4.04%H. Found: 56.10%C, 4.11%H.

EXAMPLE 54

A solution of 2.2 g of 2,3-dichloro-4-methoxythiophenol in 25 ml of dimethylformamide is added to 250 mg of sodium hydride with stirring. After gas evolution subsides a solution of 1.99 g of phenacyl bromide in 5 ml of dimethylformamide is added dropwise and stirring is continued at room temperature for 1 hour. Water (150 ml) is added. The mixture is extracted 3 times with ether and the ether solution is washed with water. After drying the organic solution is concentrated in vacuo to a solid residue. Recrystallization from acetone-hexane gives 3.0 g of α-[(2,3-dichloro-4-methoxy)phenylthio]acetophenone as fine needles, mp 109°–111°.

ANALYSIS: Calculated for $C_{15}H_{12}Cl_2O_2S$: 55.05%C, 3.70%H, 21.67%Cl. Found: 55.20%C, 3.71%H, 21.53%Cl.

EXAMPLE 55

A 0.55 g charge of sodium hydride (1.1 g of 50% sodium hydride in oil) is placed in a flask and 5.0 g of 2,3-dichloro-4-methoxythiophenol in 55 ml of dimethylformamide is added. The solution is stirred until frothing subsides and 5.4 g of p-chlorophenacyl bromide in 11 ml of dimethylformamide is added rapidly. The reaction is quenched after 40 minutes with 100 ml of ice water and the solid is collected on a filter and washed with water two times. The product is dissolved in dichloromethane and dried over anhydrous magnesium sulfate. The solution is filtered and the filtrate is evaporated. The solid is recrystallized from acetone to give 5.9 g of 4-chloro-α-[(2,3-dichloro-4-methoxy)phenylthio]acetophenone as a white solid, mp 165°–167°.

ANALYSIS: Calculated for $C_{15}H_{11}Cl_3O_2S$: 49.81%C, 3.07%H, 29.41%Cl. Found: 49.82%C, 2.80%H, 29.37%Cl.

EXAMPLE 56

A solution of 11.25 g of 2,3-dichloro-4-methoxythiophenol in 100 ml of dimethylformamide is added over 5 minutes to 1.25 g of sodium hydride (99%) with stirring. Stirring is continued for 20 minutes after the addition is complete and to the clear solution is added 4.6 g (85%; practical grade) of chloroacetone at a rate such that the reaction temperature does not rise above 50°. The mixture is stirred at ambient temperature for 1 hour and quenched with water. Extraction with dichloromethane, followed by washing and drying, yields a tan-colored oil. The crude product is purified by column chromatography over alumina. Elution with ether gives 9.8 g of 60 -[(2,3-dichloro-4-methoxy)phenylthio]acetone as a colorless solid, mp 64°–66° C.

ANALYSIS: Calculated for $C_{10}H_{10}Cl_2O_2S$: 45.29%C, 3.80%H, 12.09%S. Found: 45.34%C, 3.74%H, 11.90%S.

EXAMPLE 57

To a 0.58 g sample of sodium hydride, which had been washed twice with pentane, is added a solution of 5.0 g of 2,3-dichloro-4-methoxythiophenol dissolved in 55 ml of dimethylformamide and the resulting solution is stirred until the foaming subsides. p-Fluorophenacyl bromide (5.21 g) in 11 ml of dimethylformamide is added to the solution and the mixture is stirred at 25° for three hours. To the reaction is added 150 ml of ice water and the yellow solid is collected on a filter, washed with water, dissolved in dichloromethane and dried over anhydrous magnesium sulfate, filtered and evaporated. The residue is recrystallized from acetone to give 6.7, g of α-[2,3-dichloro-4-methoxyphenylthio]-4-fluoroacetophenone as a white solid. An analytical sample is recrystallized two times from acetone to give a product, mp 145°–147°.

ANALYSIS: Calculated for $C_{15}H_{11}Cl_2FO_2S$: 52.18%C, 3.21%H, 20.54%Cl. Found: 52.15%C, 3.19%H, 20.44%Cl.

EXAMPLE 58

α-Bromo-α-phenylacetone is prepared by adding 3.5 g of bromine to a solution of 27 g of α-phenylacetone in 100 ml of dichloromethane. Following completion of the addition, the dark brown solution is stirred at room temperature for 3 hours and concentrated to dryness.

A solution of 1.7 g of 2,3-dichloro-4-methoxythiophenol in 200 ml of anhydrous dimethylformamide is added to 2.7 g of sodium hydride. After stirring at room temperature for 10 minutes, a solution of 17.5 g of freshly prepared α-bromo-α-phenylacetone is added over 5 minutes and the mixture is stirred at room temperature for 1 hour. Ice is added. The mixture is extracted 3 times with dichloromethane and the combined organic extracts are dried over anhydrous magnesium sulfate and concentrated to an oily residue. Trituration with ether precipitates a crystalline by-product which is removed by filtration. The filtrate is concentrated and chromatographed on silica. Elution with ether-hexane (50:50) gives 10.5 g of α-[(2,3-dichloro-4-methoxy)-phenylthio]-α-phenylacetone as a wax-like semi-solid.

ANALYSIS: Calculated for $C_{16}H_{14}Cl_2O_2S$: 56.31%C, 4.13%H, 9.40%S. Found: 56.44%C, 4.12%H, 9.31%S.

EXAMPLE 59

A solution of 6.27 g 2,3-dichloro-4-methoxythiophenol in 35 ml dimethylformamide (4 Å sieve-dried) is added to sodium hydride, prepared from 1.7 g of 50% oil dispersion by washing with pentane, with mechanical stirring. Stirring is continued at room temperature for 30 minutes after completion of the addition. A solution of 3.58 g α-chlorocyclopentanone in 15 ml of dimethylformamide is added with ice bath cooling to maintain the temperature below 5°. After the addition is complete, the mixture is stirred in an ice bath for 1 hour and quenched with 5 ml water. The mixture is poured into 400 ml water and extracted with ether (3×300 ml). The organics are washed with water (2×150 ml) and dried over anhydrous magnesium sulfate. Filtration and evaporation gives 8 g of a yellow solid which is recrystallized from acetone-hexane to give 5.8 g of 2-[(2,3-dichloro-4-methoxy)phenylthio]cyclopentanone as a light yellow solid, mp 91°–93°.

ANALYSIS: Calculated for $C_{12}H_{12}Cl_2O_2S$: 49.49%C, 4.16%H. Found: 49.45%C, 4.20%H.

EXAMPLE 60

A solution of 6.27 g of 2,3-dichloro-4-methoxythiophenol in 35 ml of dimethylformamide is added rapidly to 0.85 g of 99% sodium hydride with stirring. After 10 minutes, the solution is cooled to room temperature and is added a solution of 4.0 g of 2-chlorocyclohexanone in 15 ml of dimethylformamide. Following completion of the addition, the mixture is stirred at room temperature for 30 minutes. Ice-water (200 g) is added. The precipitate is collected on a filter, washed and air dried. Recrystallization from acetone-hexane gives 6.2 g of 2-[(2,3-dichloro-4-methoxylphenythio]cyclohexanone as white prisms, mp 132°–134°.

ANALYSIS: Calculated for $C_{13}H_{14}Cl_2O_2S$: 51.15%C, 4.62%H, 10.51%S. Found: 51.03%C, 4.60%H, 10.42%S.

EXAMPLE 61

To a solution of 2.09 g of 2.3 dichlorothiophenol and 2.2 g of ethylbromophenylacetate in 30 ml of dimethylformamide is added 300 mg of sodium hydride in small portions. The reaction is mildly exothermic and after stirring at ambient temperature for 1 hour, the mixture is quenched with water. The organic materials are extracted into ether, washed and dried over anhydrous magnesium sulfate. Removal of the solvent under reduced pressure afforded 3.2 g of crude product which is recrystallized from ether-pentane to give 2.6 g of ethyl α-[(2,3-dichloro-4-methoxy)phenylthio]phenylacetate as colorless prisms, mp 82°–83°.

ANALYSIS: Calculated for $C_{17}H_{16}Cl_2O_3S$: 54.99%C, 4.34%H, 19.10%Cl. Found: 54.55%C, 4.39%H, 18.99%Cl.

EXAMPLE 62

A solution of 2.25 g of ethyl α-[(2,3-dichloro-4-methoxy)phenylthio]phenylacetate in 25 ml of ethanol containing 5.0 g of potassium hydroxide is stirred at reflux overnight. The clear solution is concentrated in vacuo to dryness and the residue is dissolved in water. Acidification with cold, conc hydrochloric acid liberates an oil which solidifies on standing. The crude product is air-dried and recrystallized from ether-hexane to give 1.7 g of α-(2,3-dichloro-4-methoxyphenylthio)phenylacetic acid as prisms, mp 180°–182°.

ANALYSIS: Calculated for $C_{15}H_{12}Cl_2O_3S$: 52.49%C, 3.53%H, 9.34%S. Found: 52.76%C, 3.56%H, 9.33%S.

EXAMPLE 63

To a solution of 4.4 g of 2,3-dichloro-4-methoxythiophenol in 30 ml of anhydrous dimethylformamide is added 1.2 g of sodium hydride in small portions. The mixture is stirred at room temperature until gas evolution subsides (20–30 minutes) and 3.34 g of α-bromobutyric acid in 10 ml of dimethylformamide is added. After stirring at room temperature for 1 hour, the mixture is diluted with water and acidified with conc. hydrochloric acid. The white crystalline solid is filtered, air dried and recrystallized from acetone-hexane to give 5.32 g of α-(2,3-dichloro-4-methoxyphenylthio)butyric acid as granular crystals, mp 143°–145°.

ANALYSIS: Calculated for $C_{11}H_{12}Cl_2O_3S$: 44.75%C, 4.10%H, 10.86%S. Found: 44.60%C, 4.15%H, 10.65%S.

EXAMPLE 64

A solution of 6.5 g of 2,3-dichloro-4-methoxythiophenol in 50 ml of dimethylformamide is added to 1.7 g of sodium hydride (99%) with stirring. After 10 minutes, the almost clear solution is treated with 5.20 g of α-bromopropionic acid in 10 ml of dimethylformamide. The slightly exothermic mixture is stirred at ambient temperature for 30 minutes, diluted with 200 ml of water and filtered. Acidification with conc hydrochloric acid precipitates a white solid which is filtered and air-dried. Recrystallization from acetone-hexane gives 6.8 g α-[(2,3-dichloro-4-methoxy)phenylthio]propionic acid as of colorless prisms, mp 119°–120°.

ANALYSIS: Calculated for $C_{10}H_{10}Cl_2O_3S$: 42.72%C, 3.59%H, 11.40%S. Found: 42.71%C, 3.53%H, 11.36%S.

EXAMPLE 65

A solution of 7.0 g of 2,3-dichloro-4-methoxythiophenol in 85 ml of dimethylformamide is added to 2.0 g of sodium hydride with stirring. After 15 minutes, the almost clear yellowish solution is treated with freshly prepared α-bromocyclopentylacetic acid in 60 ml of anhydrous dimethylformamide. The slightly exothermic mixture is stirred at ambient temperature for 90 minutes, diluted with 600 g of ice-water and filtered. Acidification with conc hydrochloric acid precipitates a white crystalline solid which is filtered and air-dried. Recrystallization of the crude product from acetone-hexane gives 7.5 g of α-(2,3-dichloro-4-methoxy)phenylthio-α-cyclopentylacetic acid as white prisms, mp 177°–180°.

ANALYSIS: Calculated for $C_{14}H_{15}Cl_2O_3S$: 50.30%C, 4.52%H. Found: 50.20%C, 4.80%H.

EXAMPLE 66

To 3.13 g of 99% sodium hydride under nitrogen at room temperature is added a solution of 12.26 g of 2,3-dichloro-4-methoxythiophenol in 100 ml of sieve-dried dimethylformamide over 2 minutes. The reaction is stirred for 12 minutes. A solution of 9.56 g of α-bromoisovaleric acid in 85 ml of dimethylformamide is added over 4 minutes. The reaction is stirred at room temperature for 3 hours, cooled in ice, diluted with 500 ml of water and filtered. The solution is cooled and acidified with 3N hydrochloric acid to give the product. The precipitate is filtered, washed with a small amount of water, dried and recrystallized from acetone-pentane to give 13.14 g of α-(2,3-dichloro-4-methoxyphenylthio)isovaleric acid as a white crystalline powder mp 176.5°–178.5°.

ANALYSIS: Calculated for $C_{12}H_{14}Cl_2O_3S$: 46.62%C, 4.57%H. Found: 46.80%C, 4.59%H.

EXAMPLE 67

To 0.82 g of 99% sodium hydride is added a solution of 2.00 g of 2,3-dichloro-4-methoxythiophenol and 0.81 g of chloroacetic acid in 30 ml of sieve-dried dimethylformamide over five minutes. The reaction is stirred 30 minutes and 50 ml of water followed by 20 ml of 20% sodium hydroxide solution is added. A solid forms. Water (250 ml) is added. The mixture is filtered and 60–70 ml of 4N hydrochloric acid is added to pH 1. The product is filtered, washed with small amount of water and dried to give 2.29 g of (2,3-dichloro-4-methoxy)-phenylthioacetic acid as a white powder, mp 155°–157°.

ANALYSIS: Calculated for $C_9H_8Cl_2O_3S$: 40.47%C, 3.02% H, 26.55%Cl. Found: 40.36%C, 3.01%H 3.01%H, 26.45%Cl.

EXAMPLE 68

To 5.31 g of 2,3-dichloroanisole is slowly added 10 ml of chlorosulfonic acid over a period of 30 minutes. The reaction is mildly exothermic and at the end of the addition, a clear solution is formed. The yellowish solution is stirred at room temperature for 1 additional hour and quenched with 200 g of crushed ice. The solid is filtered, air-dried and recrystallized from ether-pentane to give 6.9 g of 2,3-dichloro-4-methoxybenzenesulfonyl chloride as off-white prisms, mp 93°–95°.

ANALYSIS: Calculated for $C_7H_5Cl_3O_3S$: 30.51%C, 1.83%H. Found: 30.74%C, 1.78%H.

EXAMPLE 69

To a mixture of 40 g of polyphosphoric acid and 2.0 g of phosphorous pentoxide is added, in small portions over 5 to 10 minutes, 2.9 g of finely pulverized α-[(2-chloro-3-methoxy)phenylthio]-2-fluoroacetophenone at 130° C. with stirring. The reaction mixture is stirred at 130° C. for 1 hour, allowed to cool, and triturated with 200 ml of water and extracted with 3 150 ml-portions of methylene chloride. The combined organic extracts are washed, dried over anhydrous magnesium sulfate and filtered. Evaporation of the filtrate under reduced pressure affords an oily residue which deposits 2.5 g of crystalline material upon cooling. Recrystallization from ether-hexane gives 2,2 g of 7-chloro-3-(2-fluorophenyl)-6-methoxybenzo[b]thiophene as needles, mp 136°–137° C.

ANALYSIS: Calculated for: $C_{15}H_{15}ClFOS$: 61.54%C, 3.44%H. Found: 61.69%C, 3.22%H.

EXAMPLE 70

A mixture of 7.2 g of ethyl{[7-chloro-3-(2-fluorophenyl)benzo[b]thien-6-yl]oxy}acetate, 150 ml of 20% sodium hydroxide solution and 150 ml of 95% ethanol is stirred under reflux for 90 minutes. The reaction mixture is evaporated under reduced pressure, 200 ml of water is added and the solution is acidified with concentrated hydrocloric acid. The mixture is extracted with four 200 ml portions of ether. The combined organic extracts are dried over anhydrous magnesium sulfate, filtered and concentrated to give a crystalline material. Recrystallization from acetone-hexane provides {[7-chloro-3-(2-fluorophenyl)benzo[b]thien-6-yl]oxy}acetic acid as needles, mp 163°–164° C.

ANALYSIS: Calculated for $C_{16}H_{10}ClFO_3S$: 57.07%C, 2.99%H. Found: 57.18%C, 2.87%H.

EXAMPLE 71

A mixture of 9.5 g of 7-chloro-3-(2-fluorophenyl)-6-methoxybenzo[b]thiophene and 80 g of pyridine hydrochloride is heated at 190° C. for 7 hours, with stirring. Water (500 ml) is added to the cooled reaction mixture and the resulting suspension is extracted with ether (3 times). The combined ethereal extracts are cooled with dilute hydrochloric acid, dried over anhydrous magnesium sulfate and evaporated to afford 8.9 g of 7-chloro-6-hydroxy-3-(2-fluorophenyl)benzo[b]thiophene.

A mixture of 8.3 g of 7-chloro-6-hydroxy-3-(2-fluorophenyl)benzo[b]thiophene, 6.0 g of ethyl bromoacetate, 60 ml of 2-butanone, 5 ml of dimethylformamide and 4 g of potassium carbonate is heated under reflux until the standing material completely dissovles. Methylene chloride is added to the cooled reaction mixture and the resultant precipitate is collected. Evaporation of the filtrate gives 8.5 g of ethyl{[7-chloro-3-(2-fluorophenyl)benzo[b]thien-6-yl]oxy}acetate.

EXAMPLE 72

To a solution of 2.76 g of 2-fluoroacetophenone in 50 ml of ether is added dropwise over 30 minutes a solution of 3.2 g of bromine in 10 ml of chloroform. Evaporation of the reaction mixture under reduced pressure affords α-bromo-2-fluoroacetophenone.

To a solution of 3.5 g of 2-chloro-3-methoxythiophenol in 50 ml of dimethylformamide is added slowly 0.7 g of sodium hydride with efficient stirring. After 20 minutes, a solution of α-bromo-2-fluoroacetophenone in 10 ml anhydrous dimethylformamide is added over a period of 2–3 minutes. The reaction mixture is stirred for 60 minutes. The reaction mixture is diluted with 800 ml of ice-water and the resulting precipitate is collected on a filter, washed and air-dried. Recrystallization of the filter cake from acetone-hexane gives 4.1 g of α-[(2-chloro-3-methoxy)phenylthio]-2-fluoroacetophenone as prisms, mp 116°–117° C.

ANALYSIS: Calculated for $C_{15}H_{12}ClFO_2S$: 57.97%C, 3.87%H. Found: 58.06%C, 3.86%H.

EXAMPLE 73

To a suspension of 1.2 g of sodium hydride (50% in mineral oil stirred with hexane before use) in 50 ml of dimethylformamide is added a solution of 3.18 g of 2-chloro-3-methoxyphenol in 50 ml of dimethylformamide followed by 3.5 g of dimethylthiocarbamyl chloride. The reaction mixture is stirred at room temperature for 1 hour, heated gradually to 75° C. and maintained at 75° C. for 3 hours. The mixture is cooled, diluted with water and extracted thrice with methylene chloride. The organic extracts are dried, filtered and evaporated under reduced pressure to afford a semicrystalline material. Recrystallization from ether-hexane gives 3.4 g of dimethylcarbamothioic acid 0-[2-chloro-3-methoxyphenyl]ester, mp 96.5°–97.5° C.

ANALYSIS: Calculated for $C_{10}H_{12}ClNO_2S$: 48.87%C, 4.92%H, 5.75%N. Found: 49.10%C, 4.80%H, 5.67%N.

EXAMPLE 74

Three grams of dimethylcarbamothioic acid S-[2-chloro-3-methoxyphenyl]ester is heated at 240°–250° C. under an atmosphere of nitrogen for 5 hours. The melt is cooled, diluted with ether and the solution is decolarized with charcoal, filtered and evaporated. Recrystallization of the residue from ether-hexane provides 2.4 g of dimethylcarbamothioic acid 0-[2-chloro-3-methoxyphenyl]ester as prisms, mp 91°–93° C.

ANALYSIS: Calculated for $C_{10}H_{12}ClNO_2S$: 48.87%C, 4.92%H, 5.70%N. Found: 49.07%C, 4.82%H, 5.73%N.

EXAMPLE 75

A mixture of 2.45 g of 2-chloro-3-S-N,N-dimethylthiocarbamylanisole, 10 ml of methanol and 20 ml of 20% sodium hydroxide solution is heated under reflux under an atmosphere of nitrogen for 3 hours. The reaction mixture is concentrated to about one-half of its original volume and the resulting solution is acidified with conc hydrochloric acid and extracted with ether. The ethereal extracts are dried over anhydrous magnesium sulfate, filtered and evaporated under reduced pressure.

The residue is chromatographed on a column of silica gel packed with hexane and eluted with hexane-methylene chloride (50:50) to provide 2-chloro-3-methoxythiophenol as an oil.

The reaction product is homogeneous by thin-layer chromatography on silica gel.

EXAMPLE 76

A mixture of 3.5 g of [(6,7-dichloro-2-methylbenzo[b]thien-5-yl)oxy]acetic acid in 20 ml of glacial acetic acid containing 5 ml of 30% hydrogen peroxide is refluxed for 2 hours. The cooled mixture is diluted with water and extracted 3 times with ethyl acetate. The combined ethyl acetate solution is washed with water, dried and concentrated to a crystalline residue. Recrystallizaton from acetone-hexane gives 3.1 g of [(6,7-dichloro-2-methylbenzo[b]thien-5-yl)oxy]acetic acid 1,1-dioxide as yellow prisms, mp 232°–234° C.

ANALYSIS: Calculated For $C_{11}H_8Cl_2O_5S$: 40.88%C, 2.50%H. Found: 40.84%C, 2.53%H.

EXAMPLE 77

To a refluxing solution of 2.4 g of [(6,7-dichloro-3-methyl-2-phenylbenzo[b]thien-5-yl)oxy]acetic acid in 20 ml of glacial acetic acid is added dropwise 4 ml of 30% hydrogen peroxide and the mixture is heated under reflux for 2 additional hours. The cooled mixture is diluted with 150 ml of water, extracted 3 times with 100 ml portions of ethyl acetate and the combined organic solution is dried over anhydrous magnesium sulfate. Removal of solvent in vacuo at 50° leaves a crystalline residue which is recrystallized from acetone-hexane to give 2.2 g of [(6,7-Dichloro-3-methyl-2-phenylbenzo[b]-thien-5-yl)oxy] acetic acid 1, 1-dioxide as yellow prisms, mp 263°–265° C.

ANALYSIS: Calculated for $C_{17}H_{12}Cl_2O_5S$: 51.14%C, 3.03%H. Found: 51.17%C, 3.00%H.

EXAMPLE 78

A mixture of 2.7 g of 6,7-dichloro-5-methoxy-3-methyl-2-phenylbenzo[b]thiophene in 20 ml of glacial acetic acid containing 5 ml of 30% hydrogen peroxide is refluxed for 2 hrs. The cooled mixture is diluted with ice, extracted 3 times with ethyl acetate. The combined ethyl acetate solution is washed with sodium bicarbonate solution, water and dried. Removal of solvent under reduced pressure leaves a crystalline solid which is recrystallized from acetone-hexane to give 2.5 g of 6,7-Dichloro-5-methoxy-3-methyl-2-phenylbenzo[b]thiophene 1,1-dioxide yellow needles, mp 197°–199° C.

ANALYSIS: Calculated for $C_{16}H_{12}Cl_2O_3S$: 54.09%C, 3.41%H. Found: 54.35% C, 3.25%H.

EXAMPLE 79

A mixture of 4.5 g of {[6,7-dichloro-2-(2'fluorophenyl)benzo[b]thien-5-yl]oxy}acetic acid in 40 ml of glacial acetic acid containing 8 ml of hydrogen peroxide is heated under reflux for 1 hour. The cooled mixture is diluted with 100 ml of water and extracted 3 times with ethyl acetate. The combined organic extracts are washed with water, dried over anhydrous magnesium sulfate and concentrated. Recrystallization of the residue from acetone-hexane gives 3.2 g of {[6,7-dichloro-2-(2'-fluorophenyl)benzo[b]thien-5-yl]oxy}acetic acid 1,1-dioxide as yellow prisms, mp 220°–221° C.

ANALYSIS: Calculated for $C_{16}H_9Cl_2FO_5S$: 47.66%C, 2.25%H, Found: 47.72%C, 2.24%H.

EXAMPLE 80

To 1.00 g of [(6,7-dichloro-2-isopropylbenzo[b]thien-5-yl)oxy]acetic acid in 35 ml of ethyl acetate is added 1.65 g of 85% m-chloroperbenzoic acid. The reaction is stirred at reflux for 16 hours and concentrated to dryness. Tituration with dichloromethane give 1.33 g of a white solid. An additional 0.09 g is obtained by reducing the volume of the supernatant and collecting the precipitate. Recrystallization from carbon tetrachloride followed by carbontetrachloride-pentane gives 0.46 g of [(6,7-Dichloro-2-isopropylbenzo[b]thien-5-yl)oxy]acetic acid 1,1-dioxide of a pure white powder, mp 203.5°–204.5° C.

ANALYSIS: Calculated for $C_{13}H_{12}Cl_2SO_5$: 44.47%C, 3.44%H. Found: 44.34%C, 3.43%H.

EXAMPLE 81

A mixture of 12.0 g of 6,7-dichloro-2-(2-fluorophenyl)-5-hydroxybenzo[b]thiophene, 7.4 g of ethyl bromoacetate, and 7 g of potassium carbonate in 300 ml of anhydrous 2-butanone is stirred under reflux for 16 hours. The cooled mixture is filtered and the filtrate is concentrated in vacuo to give a semicrystalline mass. Recrystallization from acetone-hexane affords 13.6 g of ethyl[(6,7-Dichloro-2-(2'-fluorophenyl)benzo[b]thien-5-yl)oxy]acetate as off-white crystals, mp 118°–119°.

ANALYSIS: Calculated for $C_{18}H_{13}Cl_2FO_3S$: 54.14%C, 3.28%H. Found: 54.21%C, 3.25%H.

EXAMPLE 82

A mixture of 10 g of ethyl [(6,7-dichloro-2-(2'-fluorophenyl)benzo[b]thien-5-yl)oxy]acetate in 300 ml of 20% sodium hydroxide and 300 ml of ethanol 95%) is stirred at reflux for 2 hours. The solvent is removed under reduced pressure and the cooled mixture is diluted with 500 ml of water. The solution is acidified with conc hydrochloric acid and extracted with three 300 ml portions of ethyl acetate and ether (1:1). The combined organic extracts are washed with water, dried over anhydrous magnesium sulfate and concentrated. Recrystallization of the residue from acetone-hexane gives 8.2 g of [(6,7-Dichloro-2-(2'-fluorophenyl)benzo[b]thien-5-yl)oxy]acetic acid or off-white prims, mp 210°–212° C.

Analysis: Calculated for $C_{16}H_9Cl_2FO_3S$: 51.70%C, 2.44%H. Found: 51.93%C, 2.46%H.

EXAMPLE 83

A solution of 14 g of 2,3-dichloro-4-methoxythiophenol in 100 ml of dimethylformamide is added to 2.5 g of 95% sodium hydride with stirring. The mixture is stirred at room temperature for 10 minutes and treated cautiously with 9.0 g of o-fluorobenzyl chloride in 50 ml of dimethylformamide. Stirring is continued for one additional hour after total addition and the mixture is poured onto 500 g of ice water. The crystalline precipitate is filtered, air-dried and recrystallized from ether to give 15.1 g of 2,3-dichloro-4-methoxyphenyl 2'-fluorobenzyl sulfide as rhombic crystals, mp 92°–94° C.

Analysis: Calculated for $C_{14}H_{11}Cl_2FOS$: 53.01%C, 3.50%H. Found: 52.77%C, 3.45%H.

EXAMPLE 84

To a solution of 5 ml of 2.4M n-butyllithium in tetrahydrofuran, under an atmosphere of nitrogen, is added a solution of 3.17 g of 2,3-dichloro-4-methoxyphenyl-2'-fluorobenzyl sulfide in 30 ml of sieve-dried tetrahydrofuran over 5 minutes while the reaction temperature is maintained below −45°. The solution mixture is stirred at −50° to −60° for 1 hour and then 2 ml of sieve-dried methyl formate is added. After stirring for 5 minutes at −50° to −60°, the reaction mixture is poured onto 100 ml of 10% hydrochloric acid and extruded with ether. The combined ether extracts are dried over anhydrous magnesium sulfate, filtered and concentrated to an oil. To the oil is added 50 g of polyphosphoric acid and the mixture is heated under nitrogen at 150° to 160° for 30 minutes. The reaction mixture is allowed to cool and is poured onto ice-water and extracted with dichloromethane. The organic extracts are dried, filtered and evaporated under reduced pressure. Trituration of the residue with hexane gives 1.8 g of 6,7-dichloro-5-methoxy-2-(2-fluorophenyl)benzo[b]thiophene or white crystals, mp 143°–144° C.

A sample is recrystallized from ether-hexane for analysis.

ANALYSIS: Calculated for $C_{15}H_9Cl_2FOS$: 54.89%C, 2.76%H. Found: 54.68%C, 2.77%H.

EXAMPLE 85

A mixture of 16.0 g of 6,7-dichloro-5-methoxy-2-(2′-fluorophenyl)benzo[b]thiophene and 150 g of pyridine hydrochloride is heated at 200°–250° for 1 hour with stirring under an atmosphere of nitrogen. The mixture is allowed to cool, diluted with water and the precipitate is collected. The precipitate is dissloved in dichloromethane and the solution is washed with water, dried and filtered. Evaporation of the solvent followed by treatment of the mixture with ether-hexane gives 13.2 g of 6,7-dichloro-2-(2′-fluorophenyl)-5-hydroxybenzo[b]thiophene as an amorphous solid.

ANALYSIS: Calculated for $C_{14}H_7Cl_2FOS$: 53.69%C, 2.25%H. Found: 53.80%C, 2.18%H.

EXAMPLE 86

A mixture of 13.5 g of 6,7-dichloro-2-cyclopentyl-5-methoxybenzo[b]thiophene and 100 g of pyridine hydrochloride is heated at 190°–195° for 3 hours. The cooled mixture is triturated with water (500 ml) and extracted with 300 ml-portions of dichloromethane. The combined extracts are dried, concentrated and purified by column chromatography over silica gel. Elution with 50% dichloromethane in hexane gave 10.0 g of a colorless oil which solidified on cooling. Recrystallization from ether-hexane gives 6,7-dichloro-2-cyclopentyl-5-hydroxybenzo[b]thiophene or fine needles, mp 62.0°–63.5° C.

ANALYSIS: Calculated for $C_{13}H_{13}Cl_2OS$: 54.36%C, 4.21%H. Found: 54.20%c, 4.20%H.

EXAMPLE 87

A mixture of 9.0 g of 6,7-dichloro-2-cyclopentyl-5-hydroxybenzo[b]thiophene, 6.35 g of ethyl bromoacetate, 4.0 g of potassium carbonate and 10 ml of dimethylformamide in 200 ml of 2-butanone is refluxed for 16 hours. The cooled mixture is diluted with water (200 ml), extracted with 3×300 ml-portions of dichloromethane, and the combined organic solution is dried over anhydrous magnesium sulfate. Removal of solvents leave a colorless oil which crystallizes on cooling to give 8.9 g of ethyl [(6,7-dichloro-2-cyclopentylbenzo[b]thien-5-yl)oxy]acetate or prisms, mp 65°–67°.

ANALYSIS: Calculated for $C_{17}H_{18}Cl_2O_3S$: 54.69%C, 4.86%H. Found: 54.84%C, 4.86%H.

EXAMPLE 88

A mixture of 6.2 g of ethyl [6,7-dichloro-2-cyclopentylbenzo[b]thien-5-yl)oxy]acetate in 150 ml of 95% ethanol and 150 ml of 20% sodium hydroxide is refluxed for two hours. The cooled mixture is concentrated in vacuo to half of its volume, chilled, and acidified with conc hydrochloric acid. The curdy precipitate is extracted into a large quantity of ether (500 ml), washed with water with water and dried over anhydrous magnesium sulfate. Removal of solvent under reduced pressure leaves a solid residue which is recrystallized from acetone-hexane to give 5.31 of [(6,7-dichloro-2-cyclopentylbenzo[b]thien-5-yl)oxy]acetic acid or prisms, mp 173°–174°.

ANALYSIS: Calculated for $C_{15}H_{14}Cl_2O_3S$: 52.18%C, 4.09%H. Found: 52.15%C, 4.04%H.

EXAMPLE 89

To a stirred suspension of 5.28 g of sodium hydroxide in 100 ml of dimethylformamide under a nitrogen atmosphere at room temperature is slowly added a solution of 20.9 g of 2,3-dichloro-4-methoxythiophene in 100 ml of dimethylformamide The mixture is stirred for one hour and 19.5 g of 2-bromohexanoic acid in 100 ml of dimethylformamide is added over a period of 5–10 minutes. The reaction mixture is stirred for 3 hours at room temperature, poured onto 1 kg of ice water and basified to pH 10 with 50% sodium hydroxide solution. The resulting solution is extracted with one 100 ml-portion of chloroform. The aqueous layer is filtered through celite. The filtrate is acidified to pH 2-3 with concentrated hydrochloric acid. The aqueous solution is extracted with 3×150 ml-portions of dichloromethane. The organic layers are washed with 2×100 ml-portions of water and a 100 ml-portion of saturated sodium chloride solution. The organic layer is dried over anhydrous magnesium, filtered, and the solvent removed in vacuo to give 19.5 g of α-[(2,3-dichloro-4-methoxy)phenylthio]hexanoic acid as a white powder. The powder is recrystallized from hexane-acetone to give white crystal.

ANALYSIS: Calculated for $C_{13}H_{16}Cl_2O_3S$: 48.32%C, 4.95%H. Found: 48.14%C, 4.64%H.

EXAMPLE 90

A mixture of 1.62 g of α-[(2,3-dichloro-4-methoxy)phenylthio]hexanoic acid and 8 ml of thionyl chloride in 50 ml dichloromethane is refluxed for 30 minutes. The cooled solution is concentrated in vacuo to dryness at 60°, leaving the acid chloride as a yellow solid. The residue is dissolved in 100 ml dichloromethane, cooled to −70° and the solution is treated with 0.73 g of aluminum chloride in small portions. The cooling bath is removed after the addition is complete and the reaction mixture is stirred for 1½-2 hours. The mixture is decomposed with water and the aqueous solution is extracted with 3×100 ml portions of dichloromethane. The organic layers are combined, dried over anhydrous magnesium sulfate, filtered, and the filtrate is concentrated under reduced pressure to give a dark oil. The oil is dissolved in 100 ml of 100% ethanol and stirred under a nitrogen atmosphere. To this mixture is slowly added 1.0 g of sodium borohydride. Stirring is continued until the disappearance of the ketone intermediate, 2-n-butyl-6,7-dichloro-5-methoxybenzo[b]thiophen-3(2H)-one, is shown by a thin layer chromatography. The reaction mixture is quenched with 100 g ice-water and extracted with 3×100 ml-portions of diethyl ether. The organic layers are combined and washed with 1×100 ml-portions of water. The organic layer is dried, filtered, and the solvent removed in vacuo. The residue is chromatographed on 60 g of silica gel using dichloromethane as the eluant to give 0.76 g of 2-n-butyl-6,7-dichloro-2,3-dihydro-3-hydroxy-5-methoxybenzo[b]thiophene as an oily epimeric mixture. Upon standing, crystals form from the isolated oil. Recrystallization from ether-hexane gives an isomer which melts at 95°–96°.

ANALYSIS: Calculated for $C_{13}H_{16}Cl_2O_2S$: 51.01%C, 4.90%H. Found: 50.90%C, 5.21%H.

EXAMPLE 91

To a solution of 5.0 g of 2-n-butyl-6,7-dichloro-2,3-dichloro-3-hydroxy-5-methoxybenzo[b]thiophene in 25 ml of glacial acetic acid is added 6.5 ml of boron trifluoride etherate, with stirring. The mixture is heated on a steam bath until dissolution occurs and is stirred at room temperature for one hour. A mixture of 20 ml of 10% sodium hydroxide solution and 50 mg of ice is added followed by 50% sodium hydroxide solution to pH 7. The mixture is extracted with 3×100 ml-portions of ether. The ether extracts are washed with water, dried and concentrated to give an oil. The oil is chromatographed on 100 g silica gel column using a 9:1 hexane dichloromethane system as the eluant. Evaporation of the eluant gives 2.3 g of 6,7-dichloro-2-n-butyl-5-methoxybenzo[b]thiophene or an oil.

ANALYSIS: Calculated for $C_{13}H_{14}Cl_2OS$: 54.01%C, 4.84%H. Found: 54.27%C, 4.93%H.

EXAMPLE 92

A solution of 1.63 g of 2,3-dichloro-4-methoxythiophenol in 50 ml of sieve-dried dimethylformamide is added to 0.36 g of sodium hydride with stirring under a nitrogen atmosphere. After about 30 minutes, 1.72 g of α-bromocyclohexylacetic acid in 50 ml dimethylformamide is added and the resulting mixture stirred at room temperature for about 30 minutes. The reaction mixture is quenched with 100 g of ice, 50 ml of water and filtered. The filtrate is acidified with conc. hydrochloric acid and extracted with 3×100 ml-portion of dichloromethane. The extracts were washed with water and concentrated in vacuo to give a solid. Recrystallization from ether-pentane gives 1.7 g of α-[(2,3-dichloro-4-methoxy)phenylthio]-α-cyclohexylacetic acid as white crystals, mp 144°–145°.

ANALYSIS: Calculated for $C_{14}H_{18}Cl_2O_3S$: 51.60%C, 5.16%H. Found: 51.53%C, 5.19%H.

EXAMPLE 93

To 40 g of α-[(2,3-dichloro-4-methoxy)phenylthio]-α-cyclohexylacetic acid in 500 ml of dichloromethane is added 60 ml of thionyl chloride and 4 drops of sieve-dried dimethylformamide. The mixture is stirred under reflux for 2 hours under an atmosphere of nitrogen and evaporated under reduced pressure to give the acid chloride as a powder. The powder is dissolved in 350 ml of dichloromethane, the solution is cooled to −72° and 16.1 g of aluminum chloride is added in portions. Upon completion of the addition, the reaction temperature is allowed to rise to −7°, and after 5 to 10 minutes, ice-water is added, the mixture is extracted exhaustively with ether. The combined ether extracts are dried and evaporated. The residue is dissolved in 800 ml in absolute ethanol and 6.66 g of sodium borohydride is added portion wise, with stirring at room temperature. After the addition is complete, 800 ml of ice-water is added and the solution is extracted with three 400 ml portions of diethyl ether. The organic extracts are washed with water, sodium bicarbonate solution, saturated sodium chloride solution, dried over anhydrous magnesium sulfate, filtered and evaporated. Recrystallization of the residue from ether-pentane gives 22 g of 6,7-dichloro-2-cyclohexyl-2,3-dihydro-3-hydroxy-5-methoxybenzo[b]thiophene as crystals, mp 166.5°–167.0° C.

Analysis: Calculated for $C_{15}H_{18}Cl_2O_2S$: 54.41%C, 5.43%H. Found: 54.06%C, 5.39%H.

EXAMPLE 94

To 1 g of sodium hydride in 20 ml of dry dimethylformamide is added 4 g of 2,3-dichloro-4-methoxythiophenol in 20 ml of dry dimethylformamide. After the reaction mixture becomes homogeneous, 3.44 g of 2-bromovaleric acid in 10 ml of dry dimethylformamide is slowly added. The reaction mixture is stirred for one hour, basified with 50% sodium hydroxide solution and filtered. The filtrate is acidified with conc hydrochloric acid and allowed to stand overnight. The solid precipitate is collected, air-dried and recrystallized from ether-pentane to give 5.0 g of α-(2,3-dichloro-4-methoxy)phenylthio-n-valeric acid as white crystals, mp 120°.

Analysis: Calculated for $C_{12}H_{14}Cl_2O_3S$: 46.63%C, 4.85%H. Found: 46.48%C, 4.48%H.

EXAMPLE 95

A mixture of 14.7 g of 2-cyclohexyl-6,7-dichloro-2,3-dihydro-3-hydroxy-5-methoxybenzo[b]thiophene, 90 ml of glacial acetic acid and 21 ml of boron trifluoride etherate is warmed on a steam bath until it becomes homogeneous and then stirred for one hour. To the reaction mixture is added 100 ml of cold 10% sodium hydroxide solution. The mixture is further basified with 50% sodium hydroxide solution and extracted with three 230 ml-portions of ether. The organic extracts are dried over anhydrous magnesium sulfate, filtered and evaporated. Recrystallization of the residue from ether-hexane gives 9.0 g of 6,7-dichloro-2-cyclohexyl-5-methoxybenzo[b]thiophene as off-white crystals, mp 60°.

Analysis: Calculated for $C_{15}H_{16}Cl_2OS$: 57.15%C, 5.07%H. Found: 6.89%C, 4.96%H.

EXAMPLE 96

To a solution of 5.0 g of 6,7-dichloro-5-methoxybenzo[b]thiophene in 30 ml of dry tetrahydrofuran and 10 ml dry ethyl ether under nitrogen at −20° is added 11.7 ml of 2.2M n-butyllithium, while the temperature is maintained at −20°. After stirring for 2 hours at this temperature, the reaction mixture is added dropwise through a transfer needle to a stirred solution of 22 ml of freshly distilled acetic anhydride in 40 ml of dry tetrahydrofuran at −20°. Five minutes after the addition, the reaction mixture is poured onto 100 ml 10% hydrochloric acid. The mixture is extracted twice with dichloromethane, the organic layers are collected and dried and the solvent is removed to give a solid. The solid is washed with ethyl ether to give 1.5 g of 2-acetyl-6,7-dichloro-5-methoxybenzo[b]thiophene as a fluffy solid. Recrystallization of the residue obtained by evaporation of the filtrate from ethyl ether-hexane gives an additional 0.6 g of 2-acetyl-6,7-dichloro-5-methoxybenzo[b]thiophene.

ANALYSIS: Calculated for $C_{11}H_8Cl_2O_2S$: 48.05%C, 2.91%H. Found: 48.11%C, 2.90%H.

EXAMPLE 97

A mixture of 9.5 g of 2-acetyl-6,7-dichloro-5-methoxybenzo[b]thiophene and 95 g of pyridine hydrochloride is heated at 185°–200° for four and one-half hours and allowed to cool. While still fluid in nature, the reaction mixture is poured onto ice and the resulting aqueous mixture is extracted three times with ethyl acetate. The organic fractions are combined, washed one time with water, two times with 2N hydrochloric acid, dried over anhydrous magnesium sulfate and evaporated. The residue is recrystallized from acetone-hexane to give 5.1 g of 2-acetyl-6,7-dichloro-5-hydroxybenzo[b]thiophene, mp 199°–201°.

ANALYSIS: Calculated for $C_{10}H_6Cl_2O_2S$: 46.00%C, 2.29%H. Found: 46.29%C, 2.43%H.

EXAMPLE 98

A solution of 8.7 g of 6,7-dichloro-5-hydroxybenzo[b]thiophene in 50 ml of anhydrous tetrahydrofuran is placed in a 250 ml 3-necked flask and cooled to −25°. To the solution under nitrogen, is added dropwise 42 ml of a solution of 2.5M n-butyllithium at a rate such that the temperature did not rise above −10°. After total addition, the mixture is stirred at 0°–5° for 3 hrs. To the mixture is added 14 ml of anhydrous dimethylformamide over a period of 20 mins. The reaction mixture is allowed to warm to room temperature and stirred for 1 hr. Quenching with 400 ml of 2N hydrochloric acid, followed by extraction with ethyl acetate, gives a precipitate. Recrystallization from acetone-hexane affords 6.5 g of 6,7-dichloro-2-formyl-5-hydroxy-benzo[b]thiophene, mp 197°–198°.

ANALYSIS: Calculated for $C_9H_4Cl_2O_2S$: 43.74%C, 1.63%H. Found: 43.95%C, 1.65%H.

EXAMPLE 99

To a solution of 9.0 g of 2-acetyl-6,7-dichloro-5-hydroxybenzo[b]thiophene and 200 ml of 2-butanone is added a solution of 6.62 g of ethyl bromoacetate in 50 ml of 2-butanone, 5.2 g of potassium carbonate and 2.2 ml of dimethylformamide. The reaction mixture is heated under reflux for 2 hrs, allowed to cool and filtered. The filtrate is extracted with ether (3 times). The layers are separated and the organic phase is washed with water, saturated sodium chloride solution, dried and filtered. The filtrate is evaporated. The residue is dissolved in dichloromethane and chromatographed on alumina, using dichloromethane as the eluant. Evaporation of the eluant gives 5.1 g of ethyl[(6,7-dichloro-2-acetylbenzo[b]thien-5-yl)oxy]acetate.

EXAMPLE 100

To a solution of 6.0 g of 6,7-dichloro-2-formyl-5-hydroxybenzo[b]thiophene and 300 ml of 90% ethanol is added portionwise 1.5 g of sodium borohydride. The reaction mixture is stirred at room temperature for 20 min. Saturated sodium chloride solution is added and the mixture is extracted three times with ethyl acetate:ether (1:1). The combined organic extracts are washed with saturated sodium chloride solution, dried over anhydrous magnesium sulfate and evaporated to give 4.5 g of 6,7-dichloro-5-hydroxy-2-hydroxymethylbenzo[b]thiophene, mp 167°–169°.

ANALYSIS: Calculated for $C_9H_6Cl_2O_2S$: 43.39%C, 2.43%H. Found: 43.51%C, 2.18%H.

EXAMPLE 101

A solution of 1.24 g of 6,7-dichloro-5-hydroxy-2-hydroxymethylbenzo[b]thiophene, 0.9 g of ethyl bromoacetate, 0.6 g of potassium carbonate, 25 ml of 2-butanone and 0.5 ml of dimethylformamide is stirred under reflux for 2 hrs. The aqueous layer is extracted twice with 50 ml portions of dichloromethane. The combined organic extracts, are washed with brine, dried over anhydrous magnesium sulfate, filtered and concentrated to give a clear oil which crystallizes on standing. Recrystallization of the crude product from acetone-hexane gives 1.8 g of ethyl[(6,7-dichloro-2-hydroxymethylbenzo[b]thien-5-yl)oxy]acetate mp 117°–118.5°.

ANALYSIS: Calculated for $C_{13}H_{12}Cl_2O_4S$: 46.58%C, 3.61%H. Found: 46.33%C, 3.56%H.

EXAMPLE 102

A suspension of 6.05 g of ethyl[(6,7-dichloro-2-hydroxymethylbenzo[b]thien-5-yl)oxy]acetate in 40 ml of 95% ethanol and 56 ml of 3N hydrochloric acid is stirred under reflux for 1 hr. The cooled mixture is diluted with 200 ml of water and made acidic with concentrated hydrochloric acid until pH=2. The precipitate is extracted into ethyl acetate (3×200 ml) and the combined organic extracts are washed with brine, dried over anhydrous magnesium sulfate, filtered and concentrated. Recrystallization of the residue from acetone-hexane gives 0.5 g of [(6,7-dichloro-2-hydroxymethylbenzo[b]thien-5-yl)oxy]acetic acid, mp 187.5°–118.5°.

ANALYSIS: Calculated for $C_{11}H_8Cl_2O_4S$: 43.01%C, 2.63%H. Found: 43.40%C, 2.68%H.

EXAMPLE 103

To 5.1 g of ethyl[(6,7-dichloro-2-acetylbenzo[b]thien-5-yl)oxy]acetate in 200 ml of 95% ethanol is added 150 ml of a 6N sodium hydroxide solution and the mixture is refluxed at 100° for 45 mins. The solvent is removed in vacuo to give a white slurry to which is added 250 ml of a 6N hydrochloric acid and 200 ml ethyl ether. The mixture is stirred for 2 hrs, filtered and the filter cake is distributed between 6N hydrochloric acid and ethyl ether. The organic layers are separated and the aqueous layers are extracted with ethyl ether. The combined organic extracts are washed, dried over anhydrous magnesium sulfate, filtered and the solvent is evaporated to give a solid. Recrystallization from acetone-hexane gives 2.2 g of [(2-acetyl-6,7-dichlorobenzo[b]thien-5-yl)oxy]acetic acid, mp 203°–205°.

ANALYSIS: Calculated for $C_{12}H_8Cl_2O_4S$: 45.17%C, 2.51%H. Found: 45.12%C, 2.68%H.

EXAMPLE 104

To a solution of 6,7-dichloro-5-hydroxybenzo[b]thiophene in 28 ml of dried tetrahydrofuran at −28° is added 21 ml of 2.5M n-butyllithium, maintaining the temperature below −18°. Following the addition, the carbon tetrachloride-dry ice bath is replaced with an ice-water bath and the mixture is stirred at 0°–5° for about 4 hrs. A solution of 3.3 ml of acetone in 10 ml tetrahydrofuran is added dropwise. After stirring for one hr, the solution is poured onto 100 ml of water and acidified to pH=5–6 with glacial acetic acid. The acidic solution is extracted with ethyl acetate, washed, dried over anhydrous magnesium sulfate, filtered and the solvent is removed to give 3.84 g of 6,7-dichloro-5- hydroxy-α,α-dimethylbenzo[b]thiophene-2-methanol, mp 171°–173°.

ANALYSIS: Calculated for $C_{11}H_{10}Cl_2O_2S$: 47.68%C, 3.61%H. Found: 47.83%C, 3.60%H.

EXAMPLE 105

To a mixture of 6,7-dichloro-5-hydroxy-α,α-dimethylbenzo[b]thiophene-2-methanol in 250 ml of 2-butanone is added a solution of 7.7 g of t-butyl bromoacetate in 50 ml 2-butanone and the resultant mixture is placed in a preheated oil-bath at 95°. To the mixture is added 6.7 g of potassium carbonate and 3 ml of dimethylformamide and the reaction mixture is refluxed at 95° for 2½ hrs. The cooled mixture is filtered and 100 ml of water is added. The layers are separated and the aqueous phase is extracted two times with ethyl ether. The organic extracts are washed, dried over anhydrous magnesium sulfate, filtered and concentrated to give a solid. Recrystallization from ethyl ether and pentane gives 11.5 g of t-butyl[[6,7-dichloro-2-(1-hydroxy-1-methylethyl)benzo[b]thien-5-yl]oxy]acetate, mp 137°–138°.

ANALYSIS: Calculated for $C_{17}H_{20}Cl_2O_4S$: 52.20%C, 5.11%H. Found: 51.95%C, 5.09%H.

EXAMPLE 106

To 8.5 g of t-butyl[[6,7-dichloro-2-(1-hydroxy-1-methylethyl)benzo[b]thien-5-yl]oxy]acetate in 200 ml of ethanol is added 150 ml of a 6N sodium hydroxide solution and the mixture is refluxed at 100° for 30 mins. The cooled mixture is concentrated in vacuo to a white slurry which is diluted with 200 ml of ice water and 200 ml of ethyl ether. With stirring and efficient cooling, the mixture is acidified with 6N hydrochloric acid. The acidic mixture is extracted with ethyl ether and the ether extracts are washed, dried over anhydrous magnesium sulfate, filtered and the solvent is removed. Recrystallization of the residue from acetone and pentane gives 6.8 g of [[6,7-dichloro-2-(1-hydroxy-1-methylethyl)benzo[b]thien-5-yl]oxy]acetic acid, mp 194°–196°.

ANALYSIS: Calculated for $C_{13}H_{12}C_{20}O_4S$: 46.57%C, 3.58%H. Found: 46.33%C, 3.60%H.

EXAMPLE 107

A solution of 7.0 g of 6,7-dichloro-5-hydroxybenzo[b]thiophene in 50 ml of dry tetrahydrofuran is cooled to −30°, using a dry ice-carbon tetrachloride bath and to the mixture is added dropwise, 35 ml of 2.2M n-butyllithium in hexane while the temperature is maintained below −20°. Following the addition, the bath is replaced with an ice-water bath and the reaction is stirred for 4 hrs at a temperature of 0°–5°. To the mixture is added dropwise solution of 3 ml of freshly distilled propionaldehyde in 5 ml of tetrahydrofuran. The bath is removed. The reaction mixture is stirred for 20 minutes and poured onto cold 10% hydrochloric acid. The mixture is extracted 3 times with ethyl ether. The combined ether extracts are washed, dried and the solvent is removed to give a solid. Recrystallization from ethyl ether and hexane gives 5.9 g of 6,7-dichloro-5-hydroxy-α-ethylbenzo[b]thiophene-2-methanol, mp 145°–145.5°.

ANALYSIS: Calculated for $C_{11}H_{10}Cl_2O_2S$: 47.68%C, 3.61%H. Found: 47.47%C, 3.54%H.

EXAMPLE 108

To a mixture of 6,7-dichloro-5-hydroxy-α-ethylbenzo[b]thiophene-2-methanol and 200 ml of 2-butanone is added a mixture of 7.35 g of ethyl bromoacetate in 100 ml of 2-butanone, followed by 7.4 g of potassium carbonate and 3.3 ml of sieve-dried dimethylformamide. The reaction mixture is stirred at 95°–100° for 3 hrs, allowed to cool and filtered. To the filtrate is added 100 ml of water and the mixture is extracted with ethyl ether. The organic layers are washed, dried over anhydrous magnesium sulfate, filtered and the solvent removed to give an oil which solidifies on cooling. Recrystallization from ethyl ether and hexane gives 10 g of ethyl[(6,7-dichloro-2-(1-hydroxypropyl)benzo[b]thien-5-yl]oxy]acetate, mp 69°–70°.

ANALYSIS: Calculated for $C_{15}H_{16}Cl_2O_4S$: 49.60%C, 4.41%H. Found: 49.46%C, 4.40%H.

EXAMPLE 109

To 9.5 g of ethyl[[6,7-dichloro-2-(1-hydroxypropyl)benzo[b]thien-5-yl]oxy]acetate in 210 ml of ethanol is added 180 ml of 6N sodium hydroxide solution and the mixture is stirred at 100° for 30 mins. The cooled mixture is concentrated in vacuo to give a white slurry which is diluted with 400 ml of ice water and 300 ml of ethyl ether. With stirring and efficient cooling, the mixture is acidified with 6N hydrochloric acid. The acidic mixture is extracted with ethyl ether. The ether extracts are washed, dried over anhydrous magnesium sulfate and evaporated to dryness. Recrystallization of the residue from ethyl ether and hexane gives 7.5 g of [[6,7-dichloro-2-(1-hydroxypropyl)benzo[b]thien-5-yl]oxy]acetic acid, mp 156°–158°.

ANALYSIS: Calculated for $C_{13}H_{12}Cl_2O_4S$: 46.60%C, 3.58%H. Found: 46.32%C, 3.55%H.

EXAMPLE 110

A mixture of 5.0 g of 6,7-dichloro-2-n-butyl-5-methoxybenzo[b]thiophene and 50 g of pyridine hydrochloride, under nitrogen, is heated with stirring in a 195° oil-bath for 5 hrs. After the reaction mixture has cooled, 1000 ml of water is added and the aqueous mixture is extracted with three 250-ml portions of ether. The organic layers are combined, washed with one 200-ml portion of 2N hydrochloric acid, two 250-ml portions of water, dried over anhydrous magnesium sulfate and filtered. The solvent is removed to give an oil. Crystallization with pentane and cooling gives 3.3 g of 2-n-butyl-6,7-dichloro-5-hydroxybenzo[b]thiophene, mp 35°.

ANALYSIS: Calculated for $C_{12}H_{17}Cl_2OS$: 52.39%C, 4.36%H. Found: 52.24%C, 4.30%H.

EXAMPLE 111

A mixture of 2-n-butyl-6,7-dichloro-5-hydroxybenzo[b]thiophene, 3.6 g of ethyl bromoacetate, 3.2 g of potassium carbonate and 4 ml dimethylformamide in 50 ml of 2-butanone is refluxed for 20 hrs. The cooled mixture is poured into 100 ml water and 100 ml ether. The layers are separated and the aqueous layer is extracted with two 100-ml portions of ether. The organic layers are combined, dried over anhydrous magnesium sulfate, filtered and the solvant is removed. Recrystallization from ether-hexane gives 4.1 g of ethyl[(2-n-butyl-6,7-dichlorobenzo[b]thien-5-yl)oxy]acetate, mp 72°–73°.

ANALYSIS: Calculated for $C_{16}H_{18}Cl_2O_3S$: 53.21%C, 4.98%H. Found: 53.37%C, 4.98%H.

EXAMPLE 112

A mixture of ethyl[(2-n-butyl-6,7-dichloro-5-hydroxybenzo[b]thiophene, 75 ml 20% sodium hydroxide solution and 75 ml 95% ethanol is stirred under reflux for 2 hrs. After cooling, the solvent is removed. The residue is acidified with 100 ml of 6N hydrochloric acid (pH=2) and stirred at room temperature for 2 hrs. The solid is collected, air-dried overnight and dissolved in ether. The ether solution is dried over anhydrous magnesium sulfate, filtered and the solvent is removed. Recrystallization of the residue from acetone-hexane gives 2.2 g of [2-n-butyl-(6,7-dichlorobenzo[b]thien-5-yl)oxy]acetic acid, mp 152°–153°.

ANALYSIS: Calculated for $C_{14}H_{14}Cl_2O_3S$: 50.48%C, 4.20% H. Found: 50.44%C, 4.24%H.

EXAMPLE 113

A mixture of 4.0 g of [(2-n-butyl-6,7-dichlorobenzo[b]thien-5-yl)oxy]acetic acid in 20 ml of glacial acetic acid containing 5 ml of 30% hydrogen peroxide is refluxed for 2 hrs. The cooled mixture is filtered and the crystalline product is air dried. Recrystallization from acetone-hexane gives 4.0 g of [(2-n-butyl-6,7-dichlorobenzo[b]thien-5-yl)oxy]acetic acid 1,1-dioxide mp, 246°–248°.

ANALYSIS: Calculated for $C_{14}H_{14}Cl_2O_5S$: 46.05%C, 3.83%H. Found: 45.91%C, 3.79%H.

EXAMPLE 114

A mixture of 5.0 of 6,7-dichloro-2-cyclohexyl-5-methoxybenzo[b]thiophene and 50 g of pyridine hydrochloride is stirred at 195° for 5 hrs. The cooled mixture is diluted with 250 ml of water and the resulting aqueous mixture is extracted with 3×250 ml ether. The organic layers are combined, washed with 150 ml of 2N hydrochloric acid, 2×100 ml of water, dried over anhydrous magnesium sulfate and filtered. The solvent is removed and the residue is chromatographed on a silical gel column using hexane and then 1:1 ether-hexane as eluting solvents. Evaporation of the eluents gives 3.2 g of 6,7-dichloro-2-cyclohexyl-5-hydroxybenzo[b]thiophene. Crystallization from pentane gives the analytical sample, mp 59°–60°.

ANALYSIS: Calculated for $C_{14}H_{14}Cl_2OS$: 55.84%C, 4.65%H. Found: 56.01%C, 4.90%H.

EXAMPLE 115

To a mixture of 6,7-dichloro-2-cyclohexyl-5-hydroxybenzo[b]thiophene and 110 ml of 2-butanone is added 11.5 g of ethyl bromoacetate in 60 ml of 2-butanone, followed by 10 ml dimethylformamide and 9.5 g of potassium carbonate. The reaction mixture is stirred under nitrogen at 90°–95° for 3 hrs, allowed to cool and filtered. The filtrate is poured into a mixture of 100 ml water and 100 ml ether. The layers are separated and the aqueous layer is extracted with 200 ml of ether. The organic layers are combined dried over anhydrous magnesium sulfate, filtered and the solvent is removed to give a solid which is recrystallized in ether-hexane to give 14.8 g of ethyl [(6,7-dichloro-2-cyclohexylbenzo[b]thien-5-yl)oxy]acetate, mp 73°–75°.

ANALYSIS: Calculated for $C_{18}H_{20}Cl_2O_3S$: 55.84%C, 5.17%H. Found: 56.08%C, 5.14%H.

EXAMPLE 116

A mixture of 11.8 g of ethyl[(6,7-dichloro-2-cyclohexylbenzo[b]thien-5-yl)oxy]acetate, 250 ml of 20% sodium hydroxide and 250 ml of 95% ethanol is refluxed for 2 hrs. and allowed to cool. The solvent is removed. The residue is stirred in 350 ml of 6N hydrochloric acid for 2 hrs. The mixture is filtered and the solid is air-dried, taken up in ether and redried over anhydrous magnesium sulfate and filtered. Recrystallization of the residue from acetone-hexane gives 9.0 g of [(6,7-dichloro-2-cyclohexylbenzo[b]thien-5-yl)oxy]acetic acid, mp 167°–167.5°.

ANALYSIS: Calculated for $C_{16}H_{16}Cl_2O_3S$: 53.51%C, 4.45% H. Found: 53.64%C, 4.52%H.

EXAMPLE 117

To a mixture of 4.0 g of [(6,7-dichloro-2-cyclohexylbenzo[b]thien-5-yl)oxy]acetic acid and 20 ml of glacial acetic acid is added 5 ml of hydrogen peroxide. The mixture is refluxed for 2 hrs. The cooled mixture is filtered and the solid is taken up on 100 ml of ether. The ether solution is washed, dried and the solvent is removed. The residue is recrystallized from acetone-hexane to give 3.1 g of [(6,7-dichloro-2-cyclohexylbenzo[b]thien-5-yl)oxy]acetic acid 1,1-dioxide, mp 35°–236°.

ANALYSIS: Calculated for $C_{16}H_{16}Cl_2O_5S$: 49.13%C, 4.09%H. Found: 49.01%C, 4.16%H.

EXAMPLE 118

A mixture of [(6,7-dichloro-2-cyclopentylbenzo[b]thien-5-yl)oxy]acetic acid in 30 ml of glacial acetic acid containing 7 ml of 30% hydrogen peroxide is refluxed for 2 hrs. The cooled reaction mixture is diluted with 200 ml of water and extracted 3 times with ethyl acetate. The combined organic solution is washed with water (3×100 ml), dried over anhydrous magnesium sulfate filtered and concentrated. Recrystallization of the residue from acetone-hexane affords 2.1 g of [(6,7-dichloro-2-cyclopentylbenzo[b]thien-5-yl)oxy]acetic acid 1,1-dioxide, mp 239°–240°.

ANALYSIS: Calculated for $C_{15}H_{14}Cl_2O_5S$: 47.75%C, 3.74%H. Found: 48.04%C, 3.66%H.

EXAMPLE 119

A suspension of 13.0 g of [(6,7-dichloro-2-phenylbenzo[b]thien-5-yl)oxy]acetic acid in 125 ml of glacial acetic acid containing 20 ml of hydrogen peroxide is refluxed for 2 hrs. The cooled mixture is diluted with water and filtered. The solid is washed with water, air-dried and recrystallized from acetone-hexane to give 10.6 g of [(6,7-dichloro-2-phenybenzo[b]thien-5-yl)oxy]acetic acid 1,1-dioxide, mp 262°–263°.

ANALYSIS: Calculated for $C_{16}H_{10}Cl_2O_5S$: 49.88%C, 2.62%H. Found: 49.95%C, 2.63%H.

EXAMPLE 120

To 4.2 g of sodium hydroxide (99%) in 100 ml of dimethylformamide (dried) is added dropwise, in a nitrogen atmosphere, 35 g of 2,3-dichloro-4-methoxythiophenol in 100 ml of dimethylformamide (dried). After 30 mins, 23.5 g of α-chloro-o-xylene in 50 ml of dimethylformamide (dried) is added dropwise. The reaction mixture is stirred for one additional hour, 1000 ml of ice water is added and the mixture is filtered. The filter cake is taken up in 200 ml of dichloromethane and 50 ml of water and the layers are separated. The organic layer is washed, dried over anhydrous magnesium sulfate and the solvent is removed to give a solid. Recrystallization from hot dichloromethane yields 34.5 g of 2,3-dichloro-4-methoxy 2′-methylbenzyl sulfide, mp 126°–127°.

ANALYSIS: Calculated for $C_{15}H_{14}Cl_2OS$: 57.54%C, 4.47%H. Found: 57.55%C, 4.56% H.

EXAMPLE 121

To a solution of 15 g of 2,3-dichloro-4-methoxy 2'-methylbenzyl sulfide in 140 ml of 99% anhydrous tetrahydrofuran at −72°, under nitrogen, is added dropwise 22.1 ml of 2.6M n-butyllithium in hexane maintaining the temperature below −60 °. After the addition is complete, the mixture is stirred for 1 hr. at −60° and 9.6 ml of sieve-dried methyl formate is added. After 5 to 10 mins, the reaction mixture is poured onto 400 ml of 10% hydrochloric acid. The aqueous solution is extracted with two 200 ml-portions of ethyl ether. The ether extracts are dried, filtered and concentrated to an oil. The oil is mixed with 240 g of polyphosphoric acid, the mixture is immersed in a preheated oil and stirred at 125°–135° for 30 mins. The solution is poured into 400 ml of water, extracted with three 250-ml portions of dichloromethane and the organic extracts are washed, dried, filtered and the solvent is removed. Recrystallization of the residue from dichloromethane-hexane gives 4.8 g of 6,7-dichloro-5-methoxy-2-(2'-methylphenyl)benzo[b]thiophene, mp 156°–157°.

ANALYSIS: Calculated for $C_{16}H_{12}Cl_2OS$: 59.47%C, 3.71%H. Found: 59.28%C, 3.80%H.

EXAMPLE 122

A mixture of 4.0 g of 6,7-dichloro-5-methoxy-2-(2'-methylphenyl)benzo[b]thiophene and 40 g of pyridine hydrochloride is heated at 200°–205° for 3 hrs. To the cooled mixture is added 250 ml of water and the aqueous mixture is extracted with three 200 ml-portions of ethyl ether. The organic layers are combined, washed dried over anhydrous magnesium sulfate, filtered and the solvent is removed. Recrystallization of the residue from ether-pentane gives 2.8 g of 6,7-dichloro-5-hydroxy-2-(2'-methylphenyl)benzo[b]thiophene, mp 106°–107°.

ANALYSIS: Calculated for $C_{15}H_{10}Cl_2OS$: 58.28%C, 3.23%H. Found: 58.47%C, 3.34%H.

EXAMPLE 123

To a mixture of 6,7-dichloro-5-hydroxy-2-(2'-methylphenyl)benzo[b]thiophene and 110 ml of 2-butanone is added a mixture of 11.5 g of ethyl bromoacetate in 60 ml of 2-butanone followed by 9.4 g of potassium carbonate and 5 ml of dimethylformamide. The reaction mixture is stirred at 90°–95° for 4 hrs, allowed to cool and filtered. To the filtrate is added 100 ml of water and the mixture is extracted with two 200 ml-portions of ethyl ether. The combined organic layers are washed, dried over anhydrous magnesium sulfate, filtered and the solvent is removed. Recrystallization from ether-hexane gives 15.5 g of ethyl [(6,7-dichloro-2-(2'-methylphenyl)benzo[b]thien-5-yl)oxy]acetate, mp 93°–95°.

ANALYSIS: Calculated for $C_{19}H_{16}Cl_2O_3S$: 57.75%C, 4.05%H. Found: 57.95%C, 4.11%H.

EXAMPLE 124

A mixture of ethyl[(6,7-dichloro-2-(2'-methylphenyl)benzo[b]thien-5-yl)oxy]acetate, 280 ml of sodium hydroxide solution and 280 ml of 95% ethanol is stirred under reflux for 2 hrs. After cooling, the solvent is removed. To the residue 300 ml of 6N hydrochloric acid is added and the mixture is stirred at room temperature for 2.5 hrs. The solid is collected, taken up in ether and the ether solution is dried over anhydrous magnesium sulfate, filtered and the solvent is removed. Recrystallization from ether-pentane gives 12.2 g of [(6,7-dichloro-2-(2'-methylphenyl)benzo[b]thiophene-5-yl)oxy]acetic acid, mp 189°–190°.

ANALYSIS: Calculated for $C_{17}H_{12}Cl_2O_3S$: 55.61%C, 3.72%H. Found: 55.43%C, 3.19%H.

EXAMPLE 125

To 6.2 g of [(6,7-dichloro-2-(2'-methylphenyl)benzo[b]thien-5-yl)oxy]acetic acid is added 50 ml of glacial acetic acid, followed by the slow addition of 8 ml of 30% hydrogen peroxide. The mixture is heated under reflux for 2 hrs and allowed to cool. To the reaction mixture is added 200 ml of dichloromethane and 100 ml of water. The layers are separated and the aqueous layer is extracted with dichloromethane. The organic layers are combined, washed, dried over anhydrous magnesium sulfate, filtered and the solvent is removed. Recrystallization of the residue from hot dichloromethane-hexane gives 5.9 g of [(6,7-dichloro-2-(2'-methylphenyl)benzo[b]thien-5-yl)oxy]acetic acid 1,1-dioxide, mp 198°–200°.

ANALYSIS: Calculated for $C_{17}H_{12}Cl_2O_5S$: 51.16%C, 3.01%H. Found: 50.97%C, 3.04%H.

EXAMPLE 126

A mixture of 7.5 g of [(6,7-dichloro-2-ethylbenzo[b]thien-5-yl)oxy]acetic acid in 50 ml of glacial acetic acid is heated under reflux and 10 ml of 30% hydrogen peroxide is added dropwise. After 60 min, the mixture is diluted with 300 g of ice-water. The precipitate is collectd, air-dried and recrystallized to give 7.3 g of [(6,7-dichloro-2-ethylbenzo[b]thien-5-yl)oxy]acetic acid 1,1-dioxide, mp 232°–233°.

ANALYSIS: Calculated for $C_{12}H_{10}Cl_2O_5S$: 42.74%C, 2.99%H. Found: 42.76%C, 3.04%H.

EXAMPLE 127

A mixture of [(6,7-dichloro-2-(2'-fluorophenyl)benzo[b]thien-5-yl)oxy]acetic acid in 25 ml of glacial acetic acid is heated under reflux and 30 g of 30% hydrogen peroxide is added dropwise. After 30 mins, the cooled mixture is diluted with 200 ml of ice-water, and the precipitate is collected. The air-dried crude product is recrystallized from acetone-hexane to give 1.2 g of [7-chloro-3-(2'-fluorophenyl)benzo[b]thien-6-yl)oxy]acetic acid 1,1-dioxide, mp 210°–212°.

ANALYSIS: Calculated for $C_{16}H_{10}ClFO_5S$: 52.11%C, 2.73%H. Found: 51.94%C, 2.84%H.

EXAMPLE 128

To 1.27 g of 99% sodium hydride in 20 ml of sieve-dried dimethylformamide under a nitrogen atmosphere is added dropwise a mixture of 10 g of 2,3-dichloro-4-methoxythiophenol in 20 ml of dimethylformamide. The reaction mixture is stirred for one hr and a mixture of α,2-dichlorotoluene in 10 ml of dimethylformamide is added dropwise. The mixture is stirred until the starting material is consumed as evidenced by thin-layer chromotography. The reaction is quenched with 200 g of ice followed by 400 ml of water. The aqueous mixture is extracted with three 100-ml portions of dichloromethane, and the organic extracts are washed, dried over anhydrous magnesium sulfate and the solvent is removed. Recrystallization from acetone-hexane gives 11 g of (2,3-dichloro-4-methoxyphenyl) 2'-chlorobenzyl sulfide, mp 117°–118°.

ANALYSIS: Calculated for $C_{14}H_{11}Cl_3OS$: 50.33%C, 3.29%H. Found: 50.05%C, 3.32%H.

EXAMPLE 129

To a solution of (2,3-dichloro-4-methoxyphenyl) 2'-chlorobenzyl sulfide and 100 ml of 99% anhydrous tetrahydrofuran at −70°l under nitrogen, is added dropwise 18 ml of 2.2M n-butyllithium in hexane, maintaining the temperature below 31 60°. After the addition is complete, the mixture is stirred for one hr and 9.6 ml of sieve-dried methyl formate is added at −60°. The mixture is stirred for about 25 mins, poured into 400 ml of a cooled 10% hydrochloric acid and extracted with ethyl ether. The ether extracts are washed, dried, filtered and the solvent is removed to give a tan solid. The solid is mixed with 150 g of a polyphosphoric acid and heated 125°–130°. The mixture is poured onto 500 g of ice. The aqueous mixture is extracted with three 250-ml portions of dichloromethane. The organic extracts are washed, dried over anhydrous magnesium sulfate, filtered and the solvent is removed. Recrystallization of the residue from acetone-hexane gives 4.1 g of 6,7-dichloro-2-(2'-chlorophenyl)-5-methoxybenzo[b]thiophene, mp 170°–171°.

ANALYSIS: Calculated for $C_{15}H_9Cl_3OS$: 52.37%C, 2.62%H. Found: 52.37%C, 2.63%H.

EXAMPLE 130

A mixture of 26.8 g of 6,7-dichloro-2-(2'-chlorophenyl)-5-methoxybenzo[b]thiophene and 260 g of pyridine hydrochloride is heated at 190°–200° for 4.5 hrs. To the cooled mixture is added 800 ml of water and the aqueous mixture is extracted with three 400-ml portions of ethyl ether. The organic layers are collected, washed with 400 ml of 2N hydrochloric acid and with 200 ml of water. The organic layer is dried over anhydrous magnesium sulfate, decolorized (charcoal) overnight and the solvent is removed. Recrystallization from acetone-hexane gives 18.6 g of 6,7-dichloro-2-(2'-chlorophenyl)-5-hydroxybenzo[b]thiophene, mp 174°–175°.

ANALYSIS: Calculated for $C_{14}H_7Cl_3OS$: 51.02%C, 2.12%H. Found: 50.92%C, 2.13%H.

EXAMPLE 131

To a mixture of 6,7-dichloro-2-(2'-chlorophenyl)-5-hydroxybenzo[b]thiophene in 100 ml of 2-butanone is added a mixture of 10 g of ethyl bromoacetate in 40 ml of 2-butanone, 10 ml of dimethylformamide and 8.3 g of potassium carbonate. The mixture is refluxed for 2 hrs. The cooled mixture is filtered and 100 ml of water is added to the filtrate. The aqueous mixture is extracted with two 200-ml portions of ether. The ether extracts are washed, dried over anhydrous magnesium sulfate, filtered and concentrated. Recrystallization of the crude product from dichloromethane-hexane gives 16.7 of ethyl [6,7-dichloro-2-(2'-chlorophenyl)benzo[b]thien-5-yl)oxy]acetate, mp 108°–109°.

ANALYSIS: Calculated for $C_{18}H_{13}Cl_3O_3S$: 52.01%C, 3.13%H. Found: 52.09C, 3.16%H.

EXAMPLE 132

To 14.6 g of ethyl[(6,7-dichloro-2-(2'-chlorophenyl)-benzo[b]thien-5-yl)oxy]acetate in 300 ml of 95% ethanol is added 300 ml of sodium hydroxide solution. The mixture is stirred under reflux for 2 hrs and allowed to cool. The volume of solvent is reduced in vacuo. The mixture is acidified with 600 ml of 6N hydrochloric acid. (The addition of 250 ml of ethyl acetate increased the solubility) and extracted with ethyl acetate/ethyl ether. The organic extracts are washed, dried over anhydrous magnesium sulfate and filtered. Removal of the solvent gives a solid. Recrystallization of the solid from acetone-hexane gives 10.1 of [6,7-dichloro-2-(2'-chlorophenyl)benzo[b]thien-5-yl)oxy]acetic acid, mp 205°–207°.

ANALYSIS: Calculated for $C_{16}H_9Cl_3O_3S$: 49.58%C, 2.32%H. Found: 49.60%C, 2.48%H.

EXAMPLE 133

To 7.1 g of [(6,7-dichloro-2-(2'-chlorophenyl)benzo[b]thien-5-yl)oxy]acetic acid is added 100 ml of glacial acetic acid and, with stirring, 12.2 ml of 30% hydrogen peroxide is added dropwise. The mixture is stirred under reflux for 2 hrs and cooled. The solution is poured into 150 ml of water and extracted with three 200-ml portion of ethyl acetate-ether. The organic extracts are washed, dried, filtered and the solvent is removed to give an oil. The oil is taken up with dichloromethane and hexane is added to induce crystallization. Recrystallization from acetone-hexane gives 5.1 g of [(6,7-dichloro-2-(2'-chlorophenyl)benzo[b]thien-5-yl)oxy]acetic acid 1,1-dioxide, mp 227°–229°.

ANALYSIS: Calculated for $C_{16}H_9Cl_3O_5S$: 45.78%C, 2.14%H. Found: 46.02%C, 2.16%H.

EXAMPLE 134

To a mixture of 3.15 g of 99% sodium hydride in 100 ml of dimethylformamide is added dropwise a solution of 25 g of 2,3-dichloro-4-methoxyhiophenol in 100 ml dimethylformamide. The reaction mixture is stirred for 15 mins, following the addition. A solution of 36 g of 3-bromo-2-butanone in 50 ml of dimethylformamide is added dropwise and stirring is continued for 10 min. The reaction mixture is poured into 200 g of ice and allowed to stand overnight. The solid precipitate is collected by filtration and redissolved in dichloromethane. The dichloromethane solution is washed and dried. The solvent is removed to give an oil which crystallizes with the addition of hexane. The solid is chromatographed on an alumina column with 1:1 dichloromethane-hexane as the eluting solvent to give 22.2 g of 3-[(2,3-dichloro-4-methoxy)phenylthio]butan-2-one, mp 70°–71°.

ANALYSIS: Calculated for $C_{11}H_{12}Cl_2O_2S$: 47.34%C, 4.30%H. Found: 47.30%C, 4.31%H.

EXAMPLE 135

To a stirred mixture of 40 g of polyphosphoric acid and 8 g of phosphorous pentoxide at 140° C. is added 6.0 g of finely powdered 3-[(2,3-dichloro-4-methoxy)-phenylthio]butan-2-one. The reaction mixture is stirred for 20 mins at 140° and allowed to cool. While still warm, the mixture is poured into 500 g of ice and then extracted with three 50-ml portions of dichloromethane. The organic layers are combined, washed, dried over anhydrous magnesium sulfate and a decolorizing agent (charcoal) overnight and filtered. The solvent is removed to give 4.5 g of a solid. Recrystallization from dichloromethane-hexane gives 4.1 g of 6,7-dichloro-5-methoxy-2,3-dimethylbenzo[b]thiophene, mp 159°–160°.

ANALYSIS: Calculated for $C_{11}H_{10}Cl_2OS$: 50.60%C, 3.83%H. Found: 50.86%C, 3.88%H.

EXAMPLE 136

A mixture of 31 g of 6,7-dichloro-5-methoxy-2,3-dimethylphenylbenzo[b]thiophene and 310 g of pyridine hydrochloride is heated at 190°–210° for 5 hrs. and allowed to cool. The mixture, while still warm, is poured onto 500 ml of ice water and extracted with ethyl ether. The organic layers are combined, washed, dried over anhydrous magnesium sulfate, filtered and the solvent is removed to give a solid. Trituration with hexane gives 26.7 g of 6,7-dichloro-5-hydroxy-2,3-dimethylbenzo[b]-thiophene, mp 143°–144°.

ANALYSIS: Calculated for $C_{10}H_3Cl_2OS$: 48.61%C, 3.24%H. Found: 48.63%C, 3.30%H.

EXAMPLE 137

To a mixture of 22.4 g of 6,7-dichloro-5-hydroxy-2,3-dimethylbenzo[b]thiophene is added a mixture of 18.23 g of ethyl bromoacetate in 100 ml of 2-butanone, followed by 15 g of potassium carbonate and 7.5 ml of sieve-dried dimethylformamide. The reaction mixture is stirred at 95°–100° for 2½ hrs, allowed to cool and filtered. To the filtrate is added 100 ml of water and the mixture is extracted with ethyl ether. The organic layers are separated, washed, dried over anhydrous magnesium sulfate, filtered and the solvent is removed to give a solid. The solid is recrystallized from acetone-hexane to give 25.8 g of ethyl[(6,7-dichloro-2,3-dimethylbenzo[b]thien-5-yl)oxy]acetate, mp 102°–104°.

ANALYSIS: Calculated for $C_{14}H_{14}Cl_2O_3S$: 50.48%C, 4.20%H. Found: 50.43%C, 4.27%H.

EXAMPLE 138

To a mixture of 22.0 g of ethyl[(6,7-dichloro-2,3-dimethylbenzo[b[thien-5-yl)oxy]acetate and 600 ml of 95% ethanol is added 600 ml of 20% sodium hydroxide solution and the mixture is refluxed for 2 hrs. Most of the solvent is removed in vacuo to give a white slurry to which is added 600 ml of a 6N hydrochloric acid. After stirring for about 3 hrs, the mixture is filtered. The solid is taken up in 1:1-ethyl acetate-ethyl ether. The organic layers are washed, dried and filtered and the solvent is removed to give a solid. Recrystallization from acetone-hexane gives 17.1 g of [(6,7-dichloro-2,3-dimethylbenzo[b]thien-5-yl)oxy]acetic acid, mp 218°–219°.

ANALYSIS: Calculated for $C_{12}H_{10}Cl_2O_3S$: 47.24%C, 3.28%H. Found: 47.20%C, 3.30%H.

EXAMPLE 139

A mixture of 12.1 g of [(6,7-dichloro-2,3-dimethylbenzo[b]thien-5-yl)oxy]acetic acid, 120 ml of glacial acetic acid and 19 ml of 30% hydrogen peroxide is refluxed at 95°–100° for 2½ hrs. To the cooled mixture is added 200 ml of water and the mixture is extracted with ethyl acetate. The organic layers are separated, washed, dried over anhydrous magnesium sulfate, filtered and the solvent is removed to give a solid. Recrystallization from ethyl acetate-hexane gives 8.1 g of [(6,7-dichloro-2,3-dimethylbenzo[b]thien-5-yl)oxy]acetic acid 1,1-dioxide, mp 245°–246°.

ANALYSIS: Calculated for $C_{12}H_{10}Cl_2O_5S$: 42.76%C, 2.97%H. Found: 42.68%C, 3.05%H.

EXAMPLE 140

To 4.8 g of 99% sodium hydride in 100 ml of dimethylformamide is added dropwise a solution of 38 g of 2,3-dichloro-4-methoxythiophenol in 100 ml of dimethylformamide and the mixture is stirred for one half an hour. To the mixture is added dropwise a solution of 29.5 g of 2,6-difluorobenzyl chloride in 50 ml of dimethylformamide and the reaction mixture is stirred for 1 hr. The reaction mixture is poured into one liter of ice water. After standing for 1 hr, the precipitate is collected and taken up in ether. The ether solution is washed, dried over anhydrous magnesium sulfate and the solvent is removed to give a solid. The solid is chromatographed on a hexane packed alumina column with 1:1-dichloromethane:hexane as the eluting solvent. The solvent is removed to give 37 g of (2,3-dichloro-4-methoxyphenyl)2',6'-difluorophenyl sulfide, mp 101°–103°.

ANALYSIS: Calculated for $C_{14}H_{10}Cl_2F_2OS$: 50.18%C, 2.98%H. Found: 50.35%C, 3.08%H.

EXAMPLE 141

To 15 g of (2,3-dichloro-4-methoxyphenyl)2',6'-difluorobenzyl sulfide in 140 ml of dry tetrahydrofuran at −75° is added dropwise 25 ml of 2.2M n-butyllithium over a period of 20 mins, maintaining the temperature below 65°. After stirring at this temperature for 1 hr, 10 ml of dried methyl formate is added dropwise, maintaining the temperature below −60°. The reaction mixture is the poured into 100 ml of 10N hydrochloric acid. The mixture is extracted with ethyl ether. The ether extract is washed, dried over anhydrous magnesium sulfate, filtered and the solvent is removed to give an oil. To the oil is added 200 g of polyphosphoric acid and the mixture is heated at 130°–135°, with stirring for 30 mins. The mixture is allowed to cool and to the mixture is added 400 ml of ice water. The aqueous solution is extracted with ethyl ether. The ether extract is washed, dried over anhydrous magnesium sulfate, filtered and the solvent is removed to give an oil. Crystallization occurs by the addition of hexane. Recrystallization of the crude produdt from acetone-hexane gives 1.8 g of 6,7-dichloro-2-(2',6'-difluorophenyl)-5-methoxybenzo[b]thiophene, mp 173°–174°.

ANALYSIS: Calculated for $C_{15}H_8Cl_2F_2OS$: 52.20%C, 2.32%H. Found: 51.90%C, 2.30%H.

EXAMPLE 141A

To 15 g of (2,3-dichloro-4-methoxyphenyl)-(2',6'-difluorobenzyl)sulfide in 140 ml of dry tetrahydrofuran at −75° is added dropwise 25 ml of 2.2M n-butyllithium over a period of 20 mins, maintaining the temperature below −65°. After stirring at this temperature for 1 hr, 10 ml of dried methyl formate is added dropwise, maintaining the temperature below −60°. The reaction mixture is poured onto 100 ml of 10N hydrochloric acid. The mixture is extracted with ethyl ether. The ether extract is dried over anhydrous magnesium sulfate, filtered and the solvent is removed to give an oil. The oil is heated to 120° and 240 g of warm polyphosphoric acid is added. The reaction mixture is warmed at 130° for 20 mins. The mixture is allowed to cool and to the mixture is added 400 ml of ice water. The aqueous solution is extracted with ethyl ether. The ether extract is washed, dried over anhydrous magnesium sulfate, filtered and the solvent is removed to give an oil. Crystallization from hexane, followed by recrystallization from acetone-hexane, gives 7 g of 6,7-dichloro-2-(2',6'-difluorophenyl)-5-methoxybenzo[b]thiophene.

EXAMPLE 142

A mixture of 4.5 g of 6,7-dichloro-2-(2',6'-difluorophenyl)-5-methoxybenzo[b]thiophene and 45 g of pyridine hydrochloride is stirred at 190°–195° for 5 hrs and allowed to cool. While still fluid, the reaction mixture is poured onto 200 g of ice and stirred until thoroughly mixed. The aqueous mixture is extracted with three 200-ml portions of dichloromethane and the organic layers are combined, washed, dried over anhydrous magnesium sulfate and filtered. The solvent is removed to give a solid. The solid is recrystallized from ethyl ether-hexane to give 3.1 g of 6,7-dichloro-2-(2',6'-difluorophenyl)-5-hydroxybenzo[b]thiophene, mp 161°–162°.

ANALYSIS: Calculated for $C_{14}H_{16}Cl_2OS$: 50.77%C, 1.81%H. Found: 50.95%C, 2.08%H.

EXAMPLE 143

To a mixture of 3.41 g of 6,7-dichloro-2-(2',6'-difluorophenyl)-5-hydroxybenzo[b]thiophene and 50 ml of 2-butanone is added a mixture of 2.07 g of ethyl bromoacetate and 10 ml of 2-butanone, followed by 1.8 g of potassium carbonate and 2 ml of dimethylformamide. The reaction mixture is stirred at 95°–100° for 2½ hrs, allowed to cool and filtered. To the filtrate is added 100 ml of water and the solution is extracted with ethyl ether. The organic layers are washed, dried over anhydrous magnesium sulfate, filtered and the solvent is removed to give a solid. Recrystallization from ethyl ester-hexane gives 3.2 g of ethyl[(6,7-dichloro-2-(2',6'-difluorophenyl)benzo[b]-thien-5-yl)oxy]acetate, mp 140°–142°.

ANALYSIS: Calculated for $C_{18}H_{12}Cl_2FO_3S$: 51.82%C, 2.88%H. Found: 51.74%C, 2.85%H.

EXAMPLE 144

A mixture of 12 g of ethyl[(6,7-dichloro-2-(2',6'-difluorophenyl)benzo[b]thien-5-yl)oxy]acetate, 300 ml of sodium hydroxide solution and 300 ml of absolute ethanol is refluxed for 2 hrs and then allowed to cool. Most of the solvent is removed to give a white slurry which is stirred in 500 ml of hydrochloric acid for 2½ hours. After this time, 200 ml of a 1:1 ethyl acetate:ethyl ether is added and when solid no longer remains, the reaction mixture is extracted three times with 1:1 ethyl acetate:ethyl ether. The organic extract is washed, dried, filtered and the solvent is removed to give a solid. Recrystallization from ethyl acetate-hexane gives 10.5 g of [(6,7-dichloro-2-(2',6'-difluorophenyl)benzo[b]thien-5-yl)oxy]acetic acid, mp 204°–206°.

ANALYSIS: Calculated for $C_{16}H_8Cl_2F_2O_3S$: 49.37%C, 2.05%H. Found: 49.46%C, 2.14%H.

EXAMPLE 145

To a suspension of 7.0 g of [(6,7-dichloro-2-(2',6'-difluorophenyl)benzo[b]thien-5-yl)oxy]acetic acid and 100 ml of glacial acetic acid is added dropwise 14 ml of 30% hydrogen peroxide and the mixture is refluxed for 2 hrs. To the cooled mixture is added 250 ml of water and the aqueous mixture is extracted with 1:1 ethyl acetate:ethyl ether. The organic extracts are washed, dried, filtered and the solvent is removed to give an oil. Crystallization from acetone-hexane gives 3.7 g of [(6,7-dichloro-2-(2',6'-difluorophenyl)benzo[b]thien-5-yl)oxy]-acetic acid 1,1-dioxide, mp 225°–227°.

ANALYSIS: Calculated for $C_{16}H_8Cl_2F_2O_5S$: 45.63%C, 1.990%H. Found: 45.45%C, 1.87%H.

EXAMPLE 146

To 1.26 g of sodium hydride in 25 ml dimethylformamide (sieve dried) is added dropwise a solution of 10 of 2,3-dichloro-4-methoxythiophenol in 25 ml dimethylformamide. After the addition is complete, the reaction mixture is stirred for 25 mins and a solution of 10 g of 2,4-difluorobenzyl bromide in 25 ml dimethylformamide is added dropwise. After this addition is complete, the mixture is stirred for 10 mins and cautiously poured onto ice-water. The aqueous mixture is extracted with ethyl ether. The ether extracts are washed, dried over anhydrous magnesium sulfate, filtered and the solvent is removed to give an oil which crystallizes with cooling and trituration with hexane. Two recrystallizations with ethyl acetate-hexane give 5.1 g of (2,3-dichloro-4-methoxyphenyl)2,4-difluorobenzyl sulfide, mp 86°–88°.

ANALYSIS: Calculated for $C_{14}H_{10}Cl_2F_2OS$: 50.18%C, 2.98%H.
Found: 50.41%C, 3.00%H.

EXAMPLE 147

A mixture of 3.27 g of 6,7-dichloro-5-methoxy-2-(2'-(fluorophenyl)benzo[b]thiophene in 30 ml of glacial acetic acid containing 5.5 ml of 30% hydrogen peroxide is heated at reflux for 2 hrs. The mixture is diluted with 200 g of ice-water and filtered. The air-dried solid is recrystallized from acetone to give 2.8 g of 6,7-dichloro-2-(2'-fluorophenyl)-5-methoxybenzo[b]thiophene 1,1-dioxide, mp 267°–268°.

ANALYSIS: Calculated for $C_{15}H_9Cl_2FO_3S$: 50.15%C, 2.53%H. Found: 50.45%C, 2.43%H.

EXAMPLE 148

To 1 g of sodium hydride (99%) in 22 ml of dry dimethylformamide is added 4 g of 2,3-dichloro-4-methoxythiophenol in 20 ml of dimethylformamide. When the reaction mixture becomes clear, 3.44 g of 2-bromo-n-valeric acid in 10 ml of dimethylformamide is added slowly. The mixture is stirred for 1 hr, basified with 50% sodium hydroxide, filtered and the filtrate acidified with concentrated hydrochloric acid. The resulting cloudy mixture is allowed to stand overnight and the product is cooled and air-dried. Recrystallization from ether-pentane gives 5.0 g of α-(2,3-dichloro-4-methoxy)phenylthio-n-valeric acid, mp 120°.

ANALYSIS: Calculated for $C_{12}H_{14}Cl_2O_3S$: 46.33%C, 4.k5%C. Found: 46.48%C, 4.48%H.

EXAMPLE 149

A mixture of 96 g of α-(2,3-dichloro-4-methoxy)phenylthio-n-valeric acid in 500 ml of dichloromethane, 90 ml of thionyl chloride and 6 drops of dimethylformamide is stirred at 50°–60° for 2 hrs. The solution is taken up in one liter of dichloromethane and cooled to −78° with dry ice/acetone. To the solution is added slowly 44.58 g of aluminum chloride and the dry ice-acetone bath is removed and replaced with a salt water-ice bath whereupon the reaction temperature rises to −10°. After the reaction temperature rises to 0°, the bath is removed and the reaction mixture is quenched with 800 ml of ice-water. The mixture is extracted with three 500-ml portions of ethyl ether. The organic layers are collected, washed, dried over anhydrous magnesium sulfate, filtered and the solvent is removed to give an oil. The oil is taken up in 1300 ml of ethanol and stirred while 20 g of sodium borohydride is slowly added in small portions. After about 15 mins, the reaction mixture is quenched with 400 ml of a 10% sodium hydroxide solution and then extracted with four 400-ml portions of ethyl ether. (The use of a saturated salt water solution aids in the preparation). The organic layers are collected, washed, dried over anhydrous magnesium sulfate, filtered and the solvent is removed to give an oil. High pressure liquid chromatography of the oil, using a 70% dichloromethane:30% hexane solvent system gives 48 g of a mixture of epimeric 6,7-dichloro-2,3-dihydro-3-hydroxy-5-methoxy-2-n-propylbenzo[b]thiophene as a gum. Crystallization of the gum with ether-hexane gives 6,7-dichloro-2,3-dihydro-3-hydroxy-5-methoxy-2-n-propylbenzo[b]thiophene, mp 119°–120°.

ANALYSIS: Calculated for $C_{12}H_{14}Cl_2O_2S$: 49.17%C, 4.78%H. Found: 49.06%C, 4.67%H.

EXAMPLE 150

To a mixture of 44 g of 6,7-dichloro-2,3-dihydro-3-hydroxy-5-methoxy-2-n-propylbenzo[b]thiophene in 275 ml of glacial acetic acid is added 65 ml of boron trifluoride etherate and the mixture is warmed on a steam bath until it becomes clear. The solution is stired for 10 mins and then quenched with a mixture of 500 g of ice and 200 ml of a 10% sodium hydroxide solution. The mixture is neutralized with 50% sodium hydroxide solution and then extracted with two 300-ml portions of ethyl ether. The organic layers are combined, washed with 100 ml of a saturated sodium bicarbonate solution, 100 ml of water, dried over anhydrous magnesium sulfate, filtered and the solvent is removed to give an oil. Chromatography of the oil on an alumina column using 9:1-hexane:ethyl ether as eluting solvent gives 31 g of 6,7-dichloro-5-methoxy-2-n-propylbenzo[b]thiophene as an oil.

ANALYSIS: Calculated for $C_{12}H_{12}Cl_2OS$: 52.39%C, 4.36%H. Found: 52.46%C, 4.40%H.

EXAMPLE 151

A mixture of 29 g of 6,7-dichloro-5-methoxy-2-n-propylbenzo[b]thiophene and 280 g of pyridine hydrochloride is heated at 190° for 5 hrs and allowed to cool. The reaction mixture is poured into 300 ml of water and extracted with three 33-ml portions of ether. The ether extracts are washed with 500 ml of 2N hydrochloric acid, water, dried over anhydrous magnesium sulfate-charcoal, filtered and evaporated to give an oil. Crystallization of the oil with hexane followed by recrystallization from hexane give 15.5 g of 6,7-dichloro-5-hydroxy-2-n-propylbenzo[b]thiophene, mp 50°–51°.

ANALYSIS: Calculated for $C_{11}H_{10}Cl_2OS$: 50.60%C, 3.83%H. Found: 50.63%C, 3.85%H.

EXAMPLE 152

A mixture of 11.5 g of 6,7-dichloro-5-hydroxy-2-n-propylbenzo[b]thiophene, 8.82 g of ethyl bromoacetate, 7.52 g of potassium carbonate, 135 ml of 2-butanone and 9 ml of dimethylformamide is stirred for 3 days. The reaction mixture is filtered and 100 ml of water and 100 ml of ether are added. The layers are separated and the aqueous layer is extracted 2 times with 100-ml portions of ether. The combined organic layers are dried, filtered and the filtrate is evaporated to give an oil which crystallizes from hexane. Recrystallization from ether-hexane gives 9 g of ethyl[(6,7-dichloro-2-n-propylbenzo[b]thien-5-yl)oxy]acetate, mp 62°–63°.

ANALYSIS: Calculated for $C_{15}H_{16}Cl_2O_3S$: 51.90%C, 4.61%H. Found 51.83%C, 4.76%H.

EXAMPLE 153

To 8.0 g of ethyl[(6,7-dichloro-2-n-propylbenzo[b]thien-5-yl)oxy]acetate is added 175 ml of 95% ethanol and 175 ml of 20% sodium hydroxide solution and the mixture is stirred for 2 hrs under reflux. The solvent is removed in vacuo, leaving a white residue which is acidified with 300 ml of 6N hydrochloric acid and stirred at room temperature for 2½ hrs. The solid is collected, air dried overnight, taken up in dichloromethane, redried over anhydrous magnesium sulfate, filtered and the solvent is removed to give 7.0 g of a solid. Recrystallization from acetone-hexane gives 6.8 g of [(6,7-dichloro-2-n-propylbenzo[b]thien-5-yl)oxy]acetic acid, mp 165°–166°.

ANALYSIS: Calculated for $C_{13}H_{12}Cl_2O_3S$: 48.93%C, 3.76%H. Found: 49.12%C, 3.86%H.

EXAMPLE 154

To a mixture of 3.7 g of [(6,7-dichloro-2-n-propylbenzo[b]thien-5-yl)oxy]acetic acid and 35 ml of glacial acetic acid is added dropwise 5.5 ml of 30% hydrogen peroxide. The reaction mixture is heated under reflux for 2 hrs. The cooled mixture is filtered and the solid is air dried overnight, taken up in ethyl aetate, redried over anhydrous magnesium sulfate, filtered and the solvent is removed to give a solid. Recrystallization from acetone-hexane gives 2.5 g of [(6,7-dichloro-2-n-propylbenzo[b]thien-5-yl)oxy]acetic acid 1,1-dioxide, mp 225°–226°.

ANALYSIS: Calculated for $C_{13}H_{12}Cl_2O_5S$: 44.47%C, 3.42%H. Found: 44.18%C, 3.40%H.

EXAMPLE 155

To a solution of 25 g of 6,7-dichloro-5-hydroxybenzo[b]thiophene in 145 ml of dried tetrahydrofuran at −25° to −30° is added 110 ml of 2.5M n-butyllithium maintaining a temperature below −21°. After the addition, the carbon tetrachloride-dry ice bath is replaced with an ice-water bath and the mixture is stirred at 0°–5° for 4 hrs. A solution of 7.5 ml of freshly distilled acetaldehyde in 10 ml tetrahydrofuran is added dropwise. And additional 2 ml of acetaldehyde is added and the solution is stirred for 1 hr. The solution is poured onto 500 ml of a cold 5% hydrochloric acid solution and the mixture is extracted with ethyl ether. The ether extracts are washed, dried over anhydrous magnesium sulfate, filtered and solvent is removed to give a solid. Recrystallization from ethyl acetate and hexane gives 20 g of 6,7-dichloro-5-hydroxy-α-methylbenzo[b]thiophene-2-methanol, mp 173°–174°.

ANALYSIS: Calculated for $C_{10}H_8Cl_2O_2S$: 45.65%C, 3.04%H. Found: 45.37%C, 3.05%H.

EXAMPLE 156

To a solution of 17 g of 6,7-dichloro-5-hydroxy-α-methylbenzo[b]thiophene-2-methanol in 250 ml of 2-butanone is added a solution of 11.8 g of ethyl bromoacetate in 50 ml 2-butanone and the mixture is heated at 95°. To the mixture is added 12 g of potassium carbonate and 5.3 ml of dimethylformamide and the reaction mixture is refluxed at 100° for 2½ hrs. The cooled mixture is filtered and 100 ml of water is added. The aqueous phase is extracted two times with ethyl ether. The ether extracts are washed, dried over anhydrous magnesium sulfate, filtered and concentrated to give a solid. Recrystallization from acetone and hexane gives 19.5 g of ethyl[(6,7-dichloro-2-(1-hydroxyethyl)benzo[b]thien-5-yl)oxy]acetate, mp 101°–103°.

ANALYSIS: Calculated for $C_{14}H_{14}Cl_2O_4S$: 48.16%C, 4.01%H. Found: 48.22%C, 4.02%H.

EXAMPLE 157

To 16 g of ethyl[(6,7-dichloro-2-(1-hydroxyethyl)-benzo[b]thien-5-yl)oxy]acetate in 300 ml 95% ethanol is added 300 ml of a 6N sodium hydroxide and the mixture is refluxed at 100° for 30 mins. The cooled mixture is concentrated to a white slurry which is diluted with 200 ml of ice-water and 200 ml of ethyl ether. With stirring and efficient cooling, the mixture is acidified with 6N hydrochloric acid. The acidic mixture is extracted with ethyl ether. The ether extracts are washed, dried over anhydrous magnesium sulfate, filtered and the solvent is removed. Recrystallization of the crude product from acetone and hexane gives 11.4 g of [(6,7-dichloro-2-(1-hydroxyethyl)benzo[b]thien-5-yl)oxy]acetic acid, mp 173°–175°.

ANALYSIS: Calculated for $C_{12}H_{10}Cl_2O_4S$: 44.89%C, 3.11%H. Found: 44.74%C, 3.13%H.

EXAMPLE 158

A solution of 3.4 g of [(6,7-dichloro-2-(1-hydroxypropyl)benzo[b]thien-5-yl)oxy]acetic acid in 50 ml of glacial acetic acid is heated gently to 45°. The warm solution is allowed to cool to 35° and a solution of 2.1 g of potassium dichromate, 8 ml water and 3.2 ml of concentrated sulphuric acid is added dropwise. An ice bath is used during the addition to keep the temperature below 38°. The reaction mixture is stirred for 2 hrs at room temperature and poured into 200 ml of water. The reaction mixture is extracted with ethyl acetate (three times) and the organic extracts are washed and dried over anhydrous magnesium sulfate and filtered. The solvent is removed to give a solid which is triturated with ethyl ether to yield a powder. Recrystallization from ethyl acetate and hexane yields 2.51 g of 6,7-dichloro-[2-(1-oxopropyl)benzo[b]thien-5-yl)oxy]acetic acid. mp 223°–224°.

ANALYSIS: Calculated for $C_{13}H_{10}Cl_2O_4S$: 46.88%C, 3.00%H. Found: 46.84%C, 3.03%H.

EXAMPLE 159

To 30.25 g of 50% sodium hydride in 100 ml of sieve-dried dimethylformamide is added 60 g of 2,3-dichloro-4-methoxythiophenol in 150 ml of dimethylformamide. The reaction mixture is stirred for 30 mins and a solution of 56 g of α-bromo-α-methylvaleric acid in 100 ml of dimethylformamide is added dropwise. The mixture is stirred 1 hr. The mixture is poured onto ice and 2 liters of water and filtered. The filtrate is acidified and extracted 3 times with ether. The other extracts are washed, dried and the solvent is removed to give an oily residue, which crystallizes on standing. Recrystallization from acetone and pentane gives 44 g of α-(2,3-dichloro-4-methoxyphenylthio)-α-methyl-n-valeric acid, mp 120°–121°.

ANALYSIS: Calculated for $C_{13}H_{16}Cl_2O_3S$: 48.33%C, 4.95%H. Found: 48.56%C, 4.98%H.

EXAMPLE 160

To 47 g of α-(2,3-dichloro-4-methoxyphenylthio)-α-methyl-n-valeric acid in 500 ml of dichloromethane is added 15.4 ml of thionyl chloride and 1 ml of dimethylformamide. The reaction mixture is heated under reflux for 40 mins and then concentrated under reduced pressure to an oil. The oil is dissolved in dichloromethane and pentane is added to the cloud point. The mixture is cooled in a dry ice-acetone bath. The precipitate is collected and washed with pentane to give 40 g of the acid chloride. An additional 6 g of the acid chloride is recovered from the filtrate.

To 40 g of the acid chloride in 500 ml of dichloromethane cooled to −70° by means of a dry ice-acetone bath is added 21.2 g of aluminum chloride. The dry ice-acetone bath is replaced by a dry ice-carbon tetrachloride bath. After 1 hr, the reaction mixture is poured onto ice and the slurry is extracted with dichloromethane. The organic extracts are washed, dried, filtered and the filtrate is evaporated to afford 41 g of 6,7-dichloro-2-isobutyl-5-methoxybenzo[b]thiophene-3(2H)-one of an oily solid.

The thiophene-2(2H)-one is partially dissolved in 500 ml of ethanol and 5 g of sodium borohydride is added with stirring. The reaction mixture is stirred for 30 mins, poured onto 1 liter of ice-water and extracted with ether. The ether extracts are washed with water, sodium bicarbonate solution, sodium chloride solution, dried and filtered. The filtrate is evaporated to an oil which crystallizes with ether-hexane to afford 25 g of 6,7-dichloro-2,3-dihydro-3-hydroxy-2-isobutyl-5-methoxybenzo[b]thiophene.

EXAMPLE 161

A mixture of 18 g of 6,7-dichloro-2,3-dihydro-2-isobutyl-5-methoxybenzo[b]thiophene, 90 ml of glacial acetic acid and 25 ml of boron trifluoride etherate is heated on a steam bath until dissolution occurs and for an additional 30 mins, with stirring. The reaction mixture is poured onto ice and the mixture is basified with 25% sodium hydroxide solution and extracted with ether. The ether extracts are washed with water, sodium bicarbonate solution, water, dried and filtered. Evaporation of the filtrate affords an oil which crystallies on cooling in a dry ice-acetone bath. Chromatography of the crystalline material on alumina using dichloromethane as the eluent affords 14.5 g of 6,7-dichloro-5-methoxy-2-isobutylbenzo[b]thiophene, mp 40°–41°.

ANALYSIS: Calculated for $C_{13}H_{14}Cl_2OS$: 54.02%C, 4.84%H. Found: 53.78%C, 4.78%H.

EXAMPLE 162

A mixture of 12 g of 6,7-dichloro-5-methoxy-2-isobutylbenzo[b]thiophene and 130 g of pyridine hydrochloride is heated at 190°–200° for 4 hrs. The cooled mixture is poured onto ice and extracted with ether. The ether extracts are washed with 10% hydrochloric acid, water, dried over anhydrous magnesium sulfate-charcoal and filtered. Evaporation of the filtrate affords an oil. Chromatography of the oil on silica gel gives 8.0 g of 6,7-dichloro-5-hydroxy-2-isobutylbenzo[b]thiophene, mp 58°–59°.

ANALYSIS: Calculated for $C_{12}H_{12}Cl_2OS$: 52.40%C, 4.36%H. Found: 52.48%C, 4.41%H.

EXAMPLE 163

To a mixture of 10 g of 6,7-dichloro-5-hydroxy-2-isobutylbenzo[b]thiophene and 200 ml of 2-butanone is added a mixture of 6.9 g of ethyl bromoacetate in 50 ml of 2-butanone and by 6.6 g of potassium carbonate and 3.4 ml sieve-dried dimethylformamide. The reaction mixture is stirred at 95°–100° for 2 hrs, allowed to cool and filtered. To the filtrate is added 100 ml of water and 100 ml of ether. The organic layers are combined, washed, dried over anhydrous magnesium sulfate, filtered and the solvent is removed to give a solid. Recrystallization from ethyl ether and hexane gives 12 g of ethyl[(6,7-dichloro-2-isobutylbenzo[b]-thien-5-yl)oxy]acetate, mp 75°–76°.

ANALYSIS: Calculated for $C_{16}H_{18}Cl_2O_3S$: 53.22%C, 4.98%H. Found: 53.41%C, 5.00%H.

EXAMPLE 164

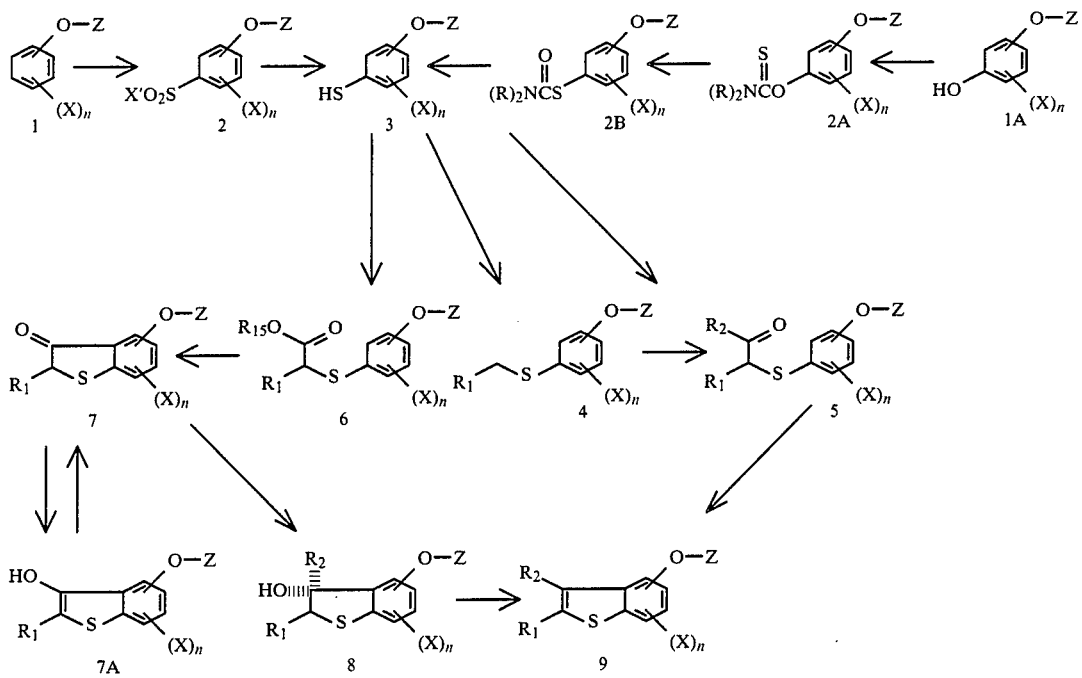

REACTION SCHEME I

To 9.6 g of ethyl[(6,7-dichloro-2-isobutylbenzo[b]thien-5-yl)oxy]acetate in 75 ml of 95% ethanol is added 175 ml of a 6N sodium hydroxide solution and the mixture is refluxed at 100° for 30 mins. The cooled mixture is concentrated in vacuo to give a slurry which is diluted with 500 ml of water and 500 ml of diethyl ether. With stirring and cooling, the mixture is acidified with 6N hydrochloric acid. The acidic mixture is extracted with diethyl ether. The ether extracts are washed, dried over anhydrous magnesium sulfate, filtered and the solvent is removed. Recrystallization of the solid from diethyl ether and hexane gives 8.3 g of [(6,7-dichloro-2-isobutylbenzo[b]thien-5-yl)oxy]acetic acid, mp 164°–165°.

ANALYSIS: Calculated for $C_{14}H_{14}Cl_2O_3S$: 50.48%C, 4.20%H. Found: 50.41%C, 4.23%H.

EXAMPLE 165

To 5 g of [(6,7-dichloro-2-isobutylbenzo[b]thien-5-yl)oxy]acetic acid and 100 ml of glacial acetic acid is added 14 ml of 30% hydrogen peroxide with stirring. The reaction mixture is stirred at 90° for 1 hr and allowed to cool. The solution is poured into 500 ml of water and the mixture is extracted with diethyl ether. The ether extracts are washed, dried over anhydrous magnesium sulfate, filtered and the solvent concentrate is removed to give a solid. Recrystallization from acetone-hexane gives 4.6 g of [(6,7-dichloro-2-isobutylbenzo[b]thien-5-yl)oxy]acetic acid 1,1-dioxide, mp 233°–235°.

ANALYSIS: Calculated for $C_{14}H_{14}Cl_2O_5S$: 46.05%C, 3.83%H. Found: 45.78%C, 3.85%H.

Wherein $R_1$, $R_2$, X and n are as hereinbefore defined, X' is chloro or fluoro, R and Z are lower alkyl and $R_{15}$ is hydrogen or lower alkyl.

REACTION SCHEME II

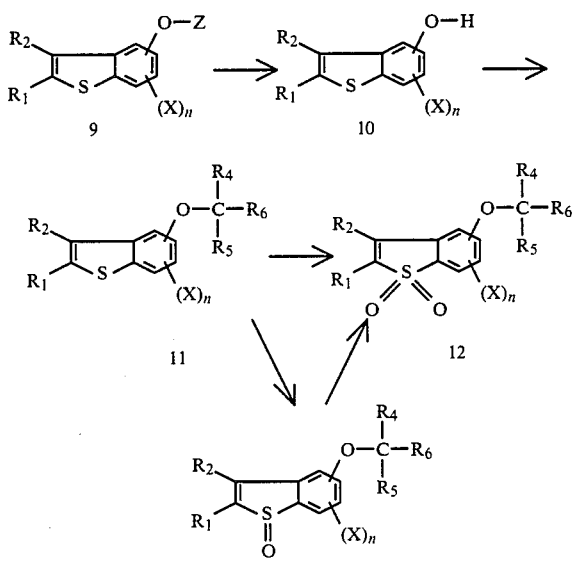

Wherein $R_1$, $R_2$, $R_4$, $R_5$, $R_6$, X, Z and n are as herein before defined.

REACTION SCHEME III

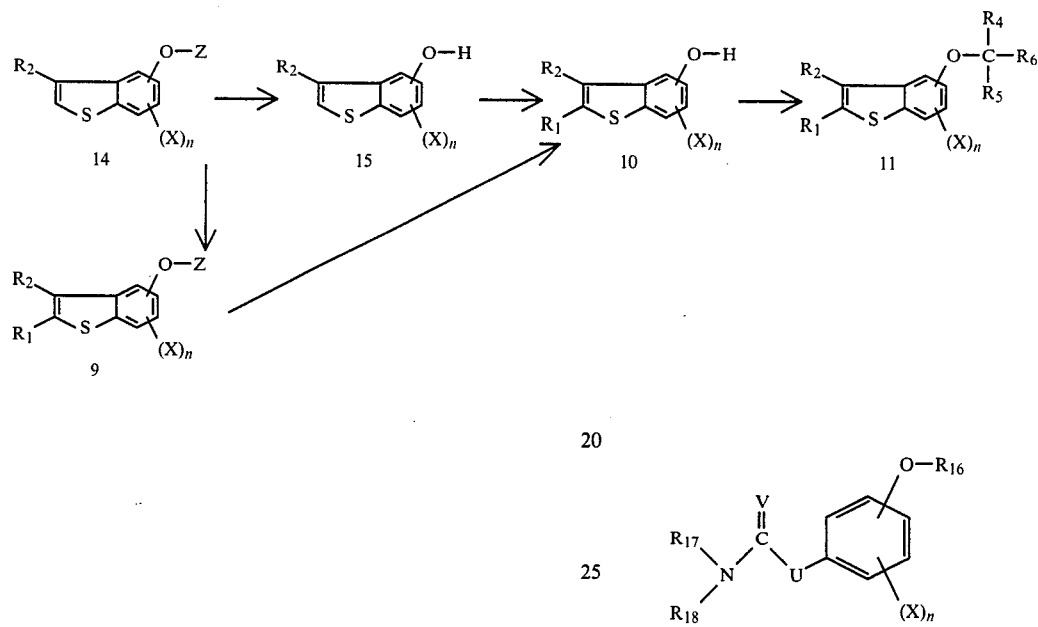

Wherein $R_1$, $R_2$, $R_4$, $R_5$, $R_6$, $X$, $Z$ and $n$ are as hereinbefore defined.

We claim:

1. A compound of the formula wherein $R_{16}$, $R_{17}$ and $R_{18}$ are each independently lower alkyl; U and V are oxygen or sulfur with the proviso that V is sulfur when U is oxygen and V is oxygen when U is sulfur; X is halogen; and n is 1 or 2.

2. The compound of claim 1 wherein X is chloro and n is 1.

3. The compound of claim 1 which is dimethylcarbamothioic acid O-[2-chloro-3-methoxyphenyl]ester.

4. The compound of claim 1 which is dimethylcarbamothioic acid S-[2-chloro-3-methoxyphenyl]ester.

* * * * *